(12) United States Patent
Black et al.

(10) Patent No.: US 10,720,084 B2
(45) Date of Patent: Jul. 21, 2020

(54) HYSTERECTOMY MODEL

(71) Applicant: Applied Medical Resources Corporation, Rancho Santa Margarita, CA (US)

(72) Inventors: Katie Black, Rancho Santa Margarita, CA (US); Gregory K. Hofstetter, Rancho Santa Margarita, CA (US); Natasha Felsinger, Rancho Santa Margarita, CA (US); Tracy Breslin, Rancho Santa Margarita, CA (US); Serene Wachli, Rancho Santa Margarita, CA (US); Sean Kenneday, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 307 days.

(21) Appl. No.: 15/705,861

(22) Filed: Sep. 15, 2017

(65) Prior Publication Data

US 2018/0005549 A1 Jan. 4, 2018

Related U.S. Application Data

(63) Continuation of application No. PCT/US2016/055148, filed on Oct. 3, 2016.
(Continued)

(51) Int. Cl.
*G09B 23/28* (2006.01)
*G09B 23/34* (2006.01)
(Continued)

(52) U.S. Cl.
CPC .............. *G09B 23/34* (2013.01); *G09B 9/00* (2013.01); *G09B 23/285* (2013.01); *G09B 23/32* (2013.01);
(Continued)

(58) Field of Classification Search
USPC ......................... 434/262, 267, 268, 272, 273
See application file for complete search history.

(56) References Cited

U.S. PATENT DOCUMENTS 184,573 A 11/1876 Becker
2,127,774 A 8/1938 Jacobs
(Continued)

FOREIGN PATENT DOCUMENTS

CN 2421706 Y 2/2001
CN 2751372 Y 1/2006
(Continued)

OTHER PUBLICATIONS

The International Bureau of WIPO, International Preliminary Report on Patentability for International Application No. PCT/US2016/055148, entitled "Hysterectomy Model," dated Apr. 12, 2018, 12 pgs.
(Continued)

*Primary Examiner* — Kurt Fernstrom
(74) *Attorney, Agent, or Firm* — Thomas Nguyen; Patrick Ikehara

(57) ABSTRACT

A surgical simulator for surgical training is provided. The simulator includes a frame defining an enclosure and a simulated tissue model located inside the enclosure. The simulated tissue model is adapted for practicing a number of surgical procedures including but not limited to transanal excisions and transvaginal hysterectomies. The simulated tissue model includes one more components and is interchangeably connected to the frame with fasteners configured to pass through apertures in the frame to suspend the simulated tissue model within the frame. The enclosure of the frame is increasingly laterally constricted along the longitudinal axis to progressively increase the confinement of the components of the simulated tissue model.

18 Claims, 41 Drawing Sheets

Related U.S. Application Data

(60) Provisional application No. 62/236,756, filed on Oct. 2, 2015, provisional application No. 62/254,477, filed on Nov. 12, 2015.

(51) Int. Cl.
    *G09B 9/00* (2006.01)
    *G09B 23/32* (2006.01)
    *A61B 17/42* (2006.01)

(52) U.S. Cl.
    CPC ....... *A61B 17/42* (2013.01); *A61B 2017/4216* (2013.01)

(56) References Cited

U.S. PATENT DOCUMENTS

| | | |
|---|---|---|
| 2,284,888 A | 6/1942 | Arneil, Jr. |
| 2,324,702 A | 7/1943 | Hoffman et al. |
| 2,345,489 A | 3/1944 | Lord |
| 2,495,568 A | 1/1950 | Coel |
| 3,766,666 A | 10/1973 | Stroop |
| 3,775,865 A | 12/1973 | Rowan |
| 3,789,518 A | 2/1974 | Chase |
| 3,921,311 A | 11/1975 | Beasley et al. |
| 3,991,490 A | 11/1976 | Markman |
| 4,001,951 A | 1/1977 | Fasse |
| 4,001,952 A | 1/1977 | Kleppinger |
| 4,321,047 A | 3/1982 | Landis |
| 4,323,350 A | 4/1982 | Bowden, Jr. |
| 4,332,569 A | 6/1982 | Burbank |
| 4,371,345 A | 2/1983 | Palmer et al. |
| 4,386,917 A | 6/1983 | Forrest |
| 4,459,113 A | 7/1984 | Boscaro Gatti et al. |
| 4,481,001 A | 11/1984 | Graham et al. |
| 4,596,528 A | 6/1986 | Lewis et al. |
| 4,726,772 A | 2/1988 | Amplatz |
| 4,737,109 A | 4/1988 | Abramson |
| 4,789,340 A | 12/1988 | Zikria |
| 4,832,978 A | 5/1989 | Lesser |
| 4,867,686 A | 9/1989 | Goldstein |
| 4,907,973 A | 3/1990 | Hon |
| 4,938,696 A | 7/1990 | Foster et al. |
| 4,940,412 A | 7/1990 | Blumenthal |
| 5,061,187 A | 10/1991 | Jerath |
| 5,083,962 A | 1/1992 | Pracas |
| 5,104,328 A | 4/1992 | Lounsbury |
| 5,149,270 A | 9/1992 | McKeown |
| 5,180,308 A | 1/1993 | Garito et al. |
| 5,230,630 A | 7/1993 | Burgett |
| 5,273,435 A | 12/1993 | Jacobson |
| 5,295,694 A | 3/1994 | Levin |
| 5,310,348 A | 5/1994 | Miller |
| 5,318,448 A | 6/1994 | Garito et al. |
| 5,320,537 A | 6/1994 | Watson |
| 5,358,408 A | 10/1994 | Medina |
| 5,368,487 A | 11/1994 | Medina |
| 5,380,207 A | 1/1995 | Siepser |
| 5,403,191 A | 4/1995 | Tuason |
| 5,425,644 A | 6/1995 | Szinicz |
| 5,425,731 A | 6/1995 | Daniel et al. |
| 5,472,345 A | 12/1995 | Eggert |
| 5,518,406 A | 5/1996 | Waters |
| 5,518,407 A | 5/1996 | Greenfield et al. |
| 5,520,633 A | 5/1996 | Costin |
| 5,541,304 A | 7/1996 | Thompson |
| 5,620,326 A | 4/1997 | Younker |
| 5,720,742 A | 2/1998 | Zacharias |
| 5,722,836 A | 3/1998 | Younker |
| 5,727,948 A | 3/1998 | Jordan |
| 5,743,730 A | 4/1998 | Clester et al. |
| 5,762,458 A | 6/1998 | Wang et al. |
| 5,769,640 A | 6/1998 | Jacobus et al. |
| 5,775,916 A | 7/1998 | Cooper et al. |
| 5,785,531 A | 7/1998 | Leung |
| 5,800,178 A | 9/1998 | Gillio |
| 5,803,746 A | 9/1998 | Barrie et al. |
| 5,807,378 A | 9/1998 | Jensen et al. |
| 5,810,880 A | 9/1998 | Jensen et al. |
| 5,814,038 A | 9/1998 | Jensen et al. |
| 5,850,033 A | 12/1998 | Mirzeabasov et al. |
| 5,855,583 A | 1/1999 | Wang et al. |
| 5,873,732 A | 2/1999 | Hasson |
| 5,873,863 A | 2/1999 | Komlosi |
| 5,908,302 A | 6/1999 | Goldfarb |
| 5,947,743 A | 9/1999 | Hasson |
| 5,951,301 A | 9/1999 | Younker |
| 6,080,181 A | 6/2000 | Jensen et al. |
| 6,083,008 A | 7/2000 | Yamada et al. |
| 6,113,395 A | 9/2000 | Hon |
| 6,234,804 B1 | 5/2001 | Yong |
| 6,336,812 B1 | 1/2002 | Cooper et al. |
| 6,398,557 B1 | 6/2002 | Hoballah |
| 6,413,264 B1 | 7/2002 | Jensen et al. |
| 6,474,993 B1 | 11/2002 | Grund et al. |
| 6,485,308 B1 | 11/2002 | Goldstein |
| 6,488,507 B1 | 12/2002 | Stoloff et al. |
| 6,497,902 B1 | 12/2002 | Ma |
| 6,511,325 B1 | 1/2003 | Lalka et al. |
| 6,517,354 B1 | 2/2003 | Levy |
| 6,568,941 B1 | 5/2003 | Goldstein |
| 6,620,174 B2 | 9/2003 | Jensen et al. |
| 6,654,000 B2 | 11/2003 | Rosenberg |
| 6,659,776 B1 | 12/2003 | Aumann et al. |
| 6,773,263 B2 | 8/2004 | Nicholls et al. |
| 6,780,016 B1 | 8/2004 | Toly |
| 6,817,973 B2 | 11/2004 | Merril et al. |
| 6,820,025 B2 | 11/2004 | Bachmann et al. |
| 6,854,976 B1 | 2/2005 | Suhr |
| 6,857,878 B1 | 2/2005 | Chosack et al. |
| 6,863,536 B1 | 3/2005 | Fisher et al. |
| 6,866,514 B2 | 3/2005 | Von Roeschlaub et al. |
| 6,887,082 B2 | 5/2005 | Shun |
| 6,929,481 B1 | 8/2005 | Alexander et al. |
| 6,939,138 B2 | 9/2005 | Chosack et al. |
| 6,950,025 B1 | 9/2005 | Nguyen |
| 6,960,617 B2 | 11/2005 | Omidian et al. |
| 6,997,719 B2 | 2/2006 | Wellman et al. |
| 7,008,232 B2 | 3/2006 | Brassel |
| 7,018,327 B1 | 3/2006 | Conti |
| 7,025,064 B2 | 4/2006 | Wang et al. |
| 7,056,123 B2 | 6/2006 | Gregorio et al. |
| 7,080,984 B1 | 7/2006 | Cohen |
| 7,118,582 B1 | 10/2006 | Wang et al. |
| 7,255,565 B2 | 8/2007 | Keegan |
| 7,269,532 B2 | 9/2007 | David et al. |
| 7,272,766 B2 | 9/2007 | Sakezles |
| 7,300,450 B2 | 11/2007 | Vleugels et al. |
| 7,364,582 B2 | 4/2008 | Lee |
| 7,404,716 B2 | 7/2008 | Gregorio et al. |
| 7,419,376 B2 | 9/2008 | Sarvazyan et al. |
| 7,427,199 B2 | 9/2008 | Sakezles |
| 7,431,189 B2 | 10/2008 | Shelton, IV et al. |
| 7,441,684 B2 | 10/2008 | Shelton, IV et al. |
| 7,465,168 B2 | 12/2008 | Allen et al. |
| 7,467,075 B2 | 12/2008 | Humphries et al. |
| 7,544,062 B1 | 6/2009 | Hauschild et al. |
| 7,549,866 B2 | 6/2009 | Cohen et al. |
| 7,553,159 B1 | 6/2009 | Arnal et al. |
| 7,575,434 B2 | 8/2009 | Palakodeti |
| 7,594,815 B2 | 9/2009 | Toly |
| 7,621,749 B2 | 11/2009 | Munday |
| 7,646,901 B2 | 1/2010 | Murphy et al. |
| 7,648,367 B1 | 1/2010 | Makower et al. |
| 7,648,513 B2 | 1/2010 | Green et al. |
| 7,651,332 B2 | 1/2010 | Dupuis et al. |
| 7,677,897 B2 | 3/2010 | Sakezles |
| 7,775,916 B1 | 8/2010 | Mahoney |
| 7,780,451 B2 | 8/2010 | Willobee et al. |
| 7,802,990 B2 | 9/2010 | Korndorffer et al. |
| 7,803,151 B2 | 9/2010 | Whitman |
| 7,806,696 B2 | 10/2010 | Alexander et al. |
| 7,819,799 B2 | 10/2010 | Merril et al. |
| 7,833,018 B2 | 11/2010 | Alexander et al. |
| 7,837,473 B2 | 11/2010 | Koh |

(56) References Cited

U.S. PATENT DOCUMENTS

| | | |
|---|---|---|
| 7,850,454 B2 | 12/2010 | Toly |
| 7,850,456 B2 | 12/2010 | Chosack et al. |
| 7,854,612 B2 | 12/2010 | Frassica et al. |
| 7,857,626 B2 | 12/2010 | Toly |
| 7,866,983 B2 | 1/2011 | Hemphill et al. |
| 7,931,470 B2 | 4/2011 | Alexander et al. |
| 7,931,471 B2 | 4/2011 | Senagore et al. |
| 7,988,992 B2 | 8/2011 | Omidian et al. |
| 7,993,140 B2 | 8/2011 | Sakezles |
| 7,997,903 B2 | 8/2011 | Hasson et al. |
| 8,007,281 B2 | 8/2011 | Toly |
| 8,007,282 B2 | 8/2011 | Gregorio et al. |
| 8,016,818 B2 | 9/2011 | Ellis et al. |
| 8,021,162 B2 | 9/2011 | Sui |
| 8,048,088 B2 | 11/2011 | Green et al. |
| 8,083,691 B2 | 12/2011 | Goldenberg et al. |
| 8,116,847 B2 | 2/2012 | Gattani et al. |
| 8,137,110 B2 | 3/2012 | Sakezles |
| 8,157,145 B2 | 4/2012 | Shelton, IV et al. |
| 8,197,464 B2 | 6/2012 | Krever et al. |
| 8,205,779 B2 | 6/2012 | Ma et al. |
| 8,221,129 B2 | 7/2012 | Parry et al. |
| 8,297,982 B2 | 10/2012 | Park et al. |
| 8,308,817 B2 | 11/2012 | Egilsson et al. |
| 8,323,028 B2 | 12/2012 | Matanhelia |
| 8,323,029 B2 | 12/2012 | Toly |
| 8,328,560 B2 | 12/2012 | Niblock et al. |
| 8,342,851 B1 | 1/2013 | Speeg et al. |
| 8,403,674 B2 | 3/2013 | Feygin et al. |
| 8,403,675 B2 | 3/2013 | Stoianovici et al. |
| 8,403,676 B2 | 3/2013 | Frassica et al. |
| 8,408,920 B2 | 4/2013 | Speller |
| 8,425,234 B2 | 4/2013 | Sakezles |
| 8,439,687 B1 | 5/2013 | Morriss et al. |
| 8,442,621 B2 | 5/2013 | Gorek et al. |
| 8,454,368 B2 | 6/2013 | Ault et al. |
| 8,459,094 B2 | 6/2013 | Yanni |
| 8,459,520 B2 | 6/2013 | Giordano et al. |
| 8,460,002 B2 | 6/2013 | Wang et al. |
| 8,469,715 B2 | 6/2013 | Ambrozio |
| 8,469,716 B2 | 6/2013 | Fedotov et al. |
| 8,480,407 B2 | 7/2013 | Campbell et al. |
| 8,480,408 B2 | 7/2013 | Ishii et al. |
| 8,491,309 B2 | 7/2013 | Parry et al. |
| 8,500,753 B2 | 8/2013 | Green et al. |
| 8,512,044 B2 | 8/2013 | Sakezles |
| 8,517,243 B2 | 8/2013 | Giordano et al. |
| 8,521,252 B2 | 8/2013 | Diez |
| 8,535,062 B2 | 9/2013 | Nguyen |
| 8,544,711 B2 | 10/2013 | Ma et al. |
| 8,556,635 B2 | 10/2013 | Toly |
| 8,608,483 B2 | 12/2013 | Trotta et al. |
| 8,613,621 B2 | 12/2013 | Henderickson et al. |
| 8,636,520 B2 | 1/2014 | Iwasaki et al. |
| D699,297 S | 2/2014 | Bahsoun et al. |
| 8,641,423 B2 | 2/2014 | Gumkowski |
| 8,647,125 B2 | 2/2014 | Johns et al. |
| 8,678,831 B2 | 3/2014 | Trotta et al. |
| 8,679,279 B2 | 3/2014 | Thompson et al. |
| 8,696,363 B2 | 4/2014 | Gray et al. |
| 8,708,213 B2 | 4/2014 | Shelton, IV et al. |
| 8,708,707 B2 | 4/2014 | Hendrickson et al. |
| 8,764,449 B2 | 7/2014 | Rios et al. |
| 8,764,452 B2 | 7/2014 | Pravong et al. |
| 8,800,839 B2 | 8/2014 | Beetel |
| 8,801,437 B2 | 8/2014 | Mousques |
| 8,801,438 B2 | 8/2014 | Sakezles |
| 8,807,414 B2 | 8/2014 | Ross et al. |
| 8,808,004 B2 | 8/2014 | Misawa et al. |
| 8,808,311 B2 | 8/2014 | Heinrich et al. |
| 8,814,573 B2 | 8/2014 | Nguyen |
| 8,827,988 B2 | 9/2014 | Belson et al. |
| 8,840,628 B2 | 9/2014 | Green et al. |
| 8,870,576 B2 | 10/2014 | Millon et al. |
| 8,888,498 B2 | 11/2014 | Bisaillon et al. |
| 8,893,946 B2 | 11/2014 | Boudreaux et al. |
| 8,911,238 B2 | 12/2014 | Forsythe |
| 8,915,742 B2 | 12/2014 | Hendrickson et al. |
| 8,945,095 B2 | 2/2015 | Blumenkranz et al. |
| 8,961,190 B2 | 2/2015 | Hart et al. |
| 8,966,954 B2 | 3/2015 | Ni et al. |
| 8,968,003 B2 | 3/2015 | Hendrickson et al. |
| 9,008,989 B2 | 4/2015 | Wilson et al. |
| 9,017,080 B1 | 4/2015 | Placik |
| 9,026,247 B2 | 5/2015 | White |
| 9,050,201 B2 | 6/2015 | Egilsson et al. |
| 9,056,126 B2 | 6/2015 | Hersel et al. |
| 9,070,306 B2 | 6/2015 | Rappel et al. |
| 9,087,458 B2 | 7/2015 | Shim et al. |
| 9,117,377 B2 | 8/2015 | Shim et al. |
| 9,119,572 B2 | 9/2015 | Gorek et al. |
| 9,123,261 B2 | 9/2015 | Lowe |
| 9,129,054 B2 | 9/2015 | Nawana et al. |
| 9,196,176 B2 | 11/2015 | Hager et al. |
| 9,226,799 B2 | 1/2016 | Lightcap et al. |
| 9,257,055 B2 | 2/2016 | Endo et al. |
| 9,265,587 B2 | 2/2016 | Vancamberg et al. |
| 9,295,468 B2 | 3/2016 | Heinrich et al. |
| 9,336,694 B2 | 5/2016 | Shim et al. |
| 9,351,714 B2 | 5/2016 | Ross et al. |
| 9,358,682 B2 | 6/2016 | Ruiz Morales |
| 9,364,224 B2 | 6/2016 | Nicholas et al. |
| 9,364,279 B2 | 6/2016 | Houser et al. |
| 9,370,361 B2 | 6/2016 | Viola et al. |
| 9,373,270 B2 | 6/2016 | Miyazaki |
| 9,439,649 B2 | 9/2016 | Shelton, IV et al. |
| 9,439,733 B2 | 9/2016 | Ha et al. |
| 9,449,532 B2 | 9/2016 | Black et al. |
| 9,468,438 B2 | 10/2016 | Baber et al. |
| 2001/0019818 A1 | 9/2001 | Yong |
| 2002/0168619 A1 | 11/2002 | Provenza |
| 2003/0031993 A1 | 2/2003 | Pugh |
| 2003/0091967 A1 | 5/2003 | Chosack et al. |
| 2003/0176770 A1 | 9/2003 | Merril et al. |
| 2004/0005423 A1 | 1/2004 | Dalton et al. |
| 2004/0126746 A1 | 7/2004 | Toly |
| 2004/0248072 A1 | 12/2004 | Gray et al. |
| 2005/0008997 A1 | 1/2005 | Herman |
| 2005/0026125 A1 | 2/2005 | Toly |
| 2005/0084833 A1 | 4/2005 | Lacey et al. |
| 2005/0131390 A1 | 6/2005 | Heinrich et al. |
| 2005/0142525 A1 | 6/2005 | Cotin et al. |
| 2005/0192595 A1 | 9/2005 | Green et al. |
| 2005/0196739 A1 | 9/2005 | Moriyama |
| 2005/0196740 A1 | 9/2005 | Moriyama |
| 2005/0214727 A1 | 9/2005 | Stoianovici et al. |
| 2006/0046235 A1 | 3/2006 | Alexander et al. |
| 2006/0252019 A1 | 11/2006 | Burkitt et al. |
| 2006/0275741 A1 | 12/2006 | Chewning et al. |
| 2007/0074584 A1 | 4/2007 | Talarico et al. |
| 2007/0077544 A1 | 4/2007 | Lemperle et al. |
| 2007/0078484 A1 | 4/2007 | Talarico et al. |
| 2007/0148626 A1 | 6/2007 | Ikeda |
| 2007/0166682 A1 | 7/2007 | Yarin et al. |
| 2007/0197895 A1 | 8/2007 | Nycz et al. |
| 2007/0225734 A1 | 9/2007 | Bell et al. |
| 2007/0275359 A1 | 11/2007 | Rotnes et al. |
| 2008/0032272 A1 | 2/2008 | Palakodeti |
| 2008/0032273 A1 | 2/2008 | Macnamara et al. |
| 2008/0052034 A1 | 2/2008 | David et al. |
| 2008/0064017 A1 | 3/2008 | Grundmeyer, III |
| 2008/0076101 A1 | 3/2008 | Hyde et al. |
| 2008/0097501 A1 | 4/2008 | Blier |
| 2008/0108869 A1 | 5/2008 | Sanders et al. |
| 2008/0187895 A1 | 8/2008 | Sakezles |
| 2008/0188948 A1 | 8/2008 | Flatt |
| 2008/0299529 A1 | 12/2008 | Schaller |
| 2009/0068627 A1 | 3/2009 | Toly |
| 2009/0142739 A1 | 6/2009 | Wang et al. |
| 2009/0142741 A1 | 6/2009 | Ault et al. |
| 2009/0143642 A1 | 6/2009 | Takahashi et al. |
| 2009/0176196 A1 | 7/2009 | Niblock et al. |
| 2009/0187079 A1 | 7/2009 | Albrecht et al. |
| 2009/0246747 A1 | 10/2009 | Buckman, Jr. |

(56) References Cited

U.S. PATENT DOCUMENTS

| | | |
|---|---|---|
| 2009/0298034 A1 | 12/2009 | Parry et al. |
| 2009/0314550 A1 | 12/2009 | Layton |
| 2010/0047752 A1 | 2/2010 | Chan et al. |
| 2010/0094312 A1 | 4/2010 | Ruiz Morales et al. |
| 2010/0099067 A1 | 4/2010 | Agro |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2010/0167254 A1 | 7/2010 | Nguyen |
| 2010/0196867 A1 | 8/2010 | Geerligs et al. |
| 2010/0204713 A1 | 8/2010 | Ruiz Morales |
| 2010/0209899 A1 | 8/2010 | Park |
| 2010/0258611 A1 | 10/2010 | Smith et al. |
| 2010/0273136 A1 | 10/2010 | Kandasami et al. |
| 2010/0279263 A1 | 11/2010 | Duryea |
| 2010/0324541 A1 | 12/2010 | Whitman |
| 2011/0046637 A1 | 2/2011 | Patel et al. |
| 2011/0046659 A1 | 2/2011 | Ramstein et al. |
| 2011/0087238 A1 | 4/2011 | Wang et al. |
| 2011/0091855 A1 | 4/2011 | Miyazaki |
| 2011/0137337 A1 | 6/2011 | van den Dool et al. |
| 2011/0200976 A1 | 8/2011 | Hou et al. |
| 2011/0207104 A1 | 8/2011 | Trotta |
| 2011/0218550 A1 | 9/2011 | Ma |
| 2011/0244436 A1 | 10/2011 | Campo |
| 2011/0269109 A2 | 11/2011 | Miyazaki |
| 2011/0281251 A1 | 11/2011 | Mousques |
| 2011/0301620 A1 | 12/2011 | Di Betta et al. |
| 2012/0015337 A1 | 1/2012 | Hendrickson et al. |
| 2012/0015339 A1 | 1/2012 | Hendrickson et al. |
| 2012/0016362 A1 | 1/2012 | Heinrich et al. |
| 2012/0028231 A1 | 2/2012 | Misawa et al. |
| 2012/0045743 A1 | 2/2012 | Okano et al. |
| 2012/0065632 A1 | 3/2012 | Shadduck |
| 2012/0082970 A1 | 4/2012 | Pravong et al. |
| 2012/0100217 A1 | 4/2012 | Green et al. |
| 2012/0115117 A1 | 5/2012 | Marshall |
| 2012/0115118 A1 | 5/2012 | Marshall |
| 2012/0116391 A1 | 5/2012 | Houser et al. |
| 2012/0148994 A1 | 6/2012 | Hori et al. |
| 2012/0164616 A1 | 6/2012 | Endo et al. |
| 2012/0165866 A1 | 6/2012 | Kaiser et al. |
| 2012/0172873 A1 | 7/2012 | Artale et al. |
| 2012/0179072 A1 | 7/2012 | Kegreiss |
| 2012/0202180 A1 | 8/2012 | Stock et al. |
| 2012/0264096 A1 | 10/2012 | Taylor et al. |
| 2012/0264097 A1 | 10/2012 | Newcott et al. |
| 2012/0282583 A1 | 11/2012 | Thaler et al. |
| 2012/0282584 A1 | 11/2012 | Millon et al. |
| 2012/0283707 A1 | 11/2012 | Giordano et al. |
| 2012/0288839 A1 | 11/2012 | Crabtree |
| 2012/0308977 A1 | 12/2012 | Tortola |
| 2013/0087597 A1 | 4/2013 | Shelton, IV et al. |
| 2013/0101973 A1 | 4/2013 | Hoke et al. |
| 2013/0105552 A1 | 5/2013 | Weir et al. |
| 2013/0116668 A1 | 5/2013 | Shelton, IV et al. |
| 2013/0157240 A1 | 6/2013 | Hart et al. |
| 2013/0171288 A1 | 7/2013 | Harders |
| 2013/0177890 A1 | 7/2013 | Sakezles |
| 2013/0192741 A1 | 8/2013 | Trotta et al. |
| 2013/0218166 A1 | 8/2013 | Elmore |
| 2013/0224709 A1 | 8/2013 | Riojas et al. |
| 2013/0245681 A1 | 9/2013 | Straehnz et al. |
| 2013/0253480 A1 | 9/2013 | Kimball et al. |
| 2013/0267876 A1 | 10/2013 | Leckenby et al. |
| 2013/0282038 A1 | 10/2013 | Dannaher et al. |
| 2013/0288216 A1 | 10/2013 | Parry, Jr. et al. |
| 2013/0302771 A1 | 11/2013 | Alderete |
| 2013/0324991 A1 | 12/2013 | Clem et al. |
| 2013/0324999 A1 | 12/2013 | Price et al. |
| 2014/0011172 A1 | 1/2014 | Lowe |
| 2014/0017651 A1 | 1/2014 | Sugimoto et al. |
| 2014/0030682 A1 | 1/2014 | Thilenius |
| 2014/0038151 A1 | 2/2014 | Hart |
| 2014/0051049 A1 | 2/2014 | Jarc et al. |
| 2014/0072941 A1 | 3/2014 | Hendrickson et al. |
| 2014/0087345 A1 | 3/2014 | Breslin et al. |
| 2014/0087346 A1 | 3/2014 | Breslin et al. |
| 2014/0087347 A1 | 3/2014 | Tracy et al. |
| 2014/0087348 A1 | 3/2014 | Tracy et al. |
| 2014/0088413 A1 | 3/2014 | Von Bucsh et al. |
| 2014/0093852 A1 | 4/2014 | Poulsen et al. |
| 2014/0093854 A1 | 4/2014 | Poulsen et al. |
| 2014/0099858 A1 | 4/2014 | Hernandez |
| 2014/0106328 A1 | 4/2014 | Loor |
| 2014/0107471 A1 | 4/2014 | Haider et al. |
| 2014/0156002 A1 | 6/2014 | Thompson et al. |
| 2014/0162016 A1 | 6/2014 | Matsui et al. |
| 2014/0170623 A1 | 6/2014 | Jarstad et al. |
| 2014/0186809 A1 | 7/2014 | Hendrickson et al. |
| 2014/0200561 A1 | 7/2014 | Ingmanson et al. |
| 2014/0212861 A1 | 7/2014 | Romano |
| 2014/0220527 A1 | 8/2014 | Li et al. |
| 2014/0220530 A1 | 8/2014 | Merkle et al. |
| 2014/0220532 A1 | 8/2014 | Ghez et al. |
| 2014/0242564 A1 | 8/2014 | Pravong et al. |
| 2014/0246479 A1 | 9/2014 | Baber et al. |
| 2014/0248596 A1* | 9/2014 | Hart ............... G09B 23/30 434/272 |
| 2014/0263538 A1 | 9/2014 | Leimbach et al. |
| 2014/0272878 A1 | 9/2014 | Shim et al. |
| 2014/0272879 A1 | 9/2014 | Shim et al. |
| 2014/0275795 A1 | 9/2014 | Little et al. |
| 2014/0275981 A1 | 9/2014 | Selover et al. |
| 2014/0277017 A1 | 9/2014 | Leimbach et al. |
| 2014/0303643 A1 | 10/2014 | Ha et al. |
| 2014/0303646 A1 | 10/2014 | Morgan et al. |
| 2014/0303660 A1 | 10/2014 | Boyden et al. |
| 2014/0308643 A1 | 10/2014 | Trotta et al. |
| 2014/0342334 A1 | 11/2014 | Black et al. |
| 2014/0349266 A1 | 11/2014 | Choi |
| 2014/0350530 A1 | 11/2014 | Ross et al. |
| 2014/0357977 A1 | 12/2014 | Zhou |
| 2014/0370477 A1 | 12/2014 | Black et al. |
| 2014/0371761 A1 | 12/2014 | Juanpera |
| 2014/0378995 A1 | 12/2014 | Kumar et al. |
| 2015/0031008 A1 | 1/2015 | Black et al. |
| 2015/0037773 A1 | 2/2015 | Quirarte Catano |
| 2015/0038613 A1 | 2/2015 | Sun et al. |
| 2015/0076207 A1 | 3/2015 | Boudreaux et al. |
| 2015/0086955 A1 | 3/2015 | Poniatowski et al. |
| 2015/0132732 A1 | 5/2015 | Hart et al. |
| 2015/0132733 A1 | 5/2015 | Garvik et al. |
| 2015/0135832 A1 | 5/2015 | Blumenkranz et al. |
| 2015/0148660 A1 | 5/2015 | Weiss et al. |
| 2015/0164598 A1 | 6/2015 | Blumenkranz et al. |
| 2015/0187229 A1 | 7/2015 | Wachli et al. |
| 2015/0194075 A1 | 7/2015 | Rappel et al. |
| 2015/0202299 A1 | 7/2015 | Burdick et al. |
| 2015/0209035 A1 | 7/2015 | Zemlock |
| 2015/0209059 A1 | 7/2015 | Trees et al. |
| 2015/0209573 A1 | 7/2015 | Hibner et al. |
| 2015/0228206 A1 | 8/2015 | Shim et al. |
| 2015/0262511 A1 | 9/2015 | Lin et al. |
| 2015/0265431 A1 | 9/2015 | Egilsson et al. |
| 2015/0272571 A1 | 10/2015 | Leimbach et al. |
| 2015/0272574 A1 | 10/2015 | Leimbach et al. |
| 2015/0272580 A1 | 10/2015 | Leimbach et al. |
| 2015/0272581 A1 | 10/2015 | Leimbach et al. |
| 2015/0272583 A1 | 10/2015 | Leimbach et al. |
| 2015/0272604 A1 | 10/2015 | Chowaniec et al. |
| 2015/0332609 A1 | 11/2015 | Alexander |
| 2015/0358426 A1 | 12/2015 | Kimball et al. |
| 2015/0371560 A1 | 12/2015 | Lowe |
| 2015/0374378 A1 | 12/2015 | Giordano et al. |
| 2015/0374449 A1 | 12/2015 | Chowaniec et al. |
| 2016/0000437 A1 | 1/2016 | Giordano et al. |
| 2016/0022374 A1 | 1/2016 | Haider et al. |
| 2016/0030240 A1 | 2/2016 | Gonenc et al. |
| 2016/0031091 A1 | 2/2016 | Popovic et al. |
| 2016/0066909 A1 | 3/2016 | Baber et al. |
| 2016/0070436 A1 | 3/2016 | Thomas et al. |
| 2016/0073928 A1 | 3/2016 | Soper et al. |

(56) References Cited

U.S. PATENT DOCUMENTS

| | | |
|---|---|---|
| 2016/0074103 A1 | 3/2016 | Sartor |
| 2016/0098933 A1 | 4/2016 | Reiley et al. |
| 2016/0104394 A1 | 4/2016 | Miyazaki |
| 2016/0117956 A1 | 4/2016 | Larsson et al. |
| 2016/0133158 A1 | 5/2016 | Sui et al. |
| 2016/0140876 A1 | 5/2016 | Jabbour et al. |
| 2016/0199059 A1 | 7/2016 | Shelton, IV et al. |
| 2016/0220150 A1 | 8/2016 | Sharonov |
| 2016/0220314 A1 | 8/2016 | Huelman et al. |
| 2016/0225288 A1 | 8/2016 | East et al. |
| 2016/0232819 A1 | 8/2016 | Hofstetter et al. |
| 2016/0235494 A1 | 8/2016 | Shelton, IV et al. |
| 2016/0256187 A1 | 9/2016 | Shelton, IV et al. |
| 2016/0256229 A1 | 9/2016 | Morgan et al. |
| 2016/0262736 A1 | 9/2016 | Ross et al. |
| 2016/0262745 A1 | 9/2016 | Morgan et al. |
| 2016/0293055 A1 | 10/2016 | Hofstetter |
| 2016/0296144 A1 | 10/2016 | Gaddam et al. |

FOREIGN PATENT DOCUMENTS

| | | |
|---|---|---|
| CN | 2909427 Y | 6/2007 |
| CN | 101313842 A | 12/2008 |
| CN | 201364679 Y | 12/2009 |
| CN | 201955979 U | 8/2011 |
| CN | 202443680 U | 9/2012 |
| CN | 202563792 U | 11/2012 |
| CN | 202601055 U | 12/2012 |
| CN | 202694651 U | 1/2013 |
| CN | 103050040 A | 4/2013 |
| CN | 203013103 U | 6/2013 |
| CN | 203038549 U | 7/2013 |
| CN | 203338651 U | 12/2013 |
| CN | 203397593 U | 1/2014 |
| CN | 203562128 U | 4/2014 |
| CN | 103886797 A | 6/2014 |
| DE | 9102218 U1 | 5/1991 |
| DE | 41 05 892 A1 | 8/1992 |
| DE | 44 14 832 A1 | 11/1995 |
| DE | 19716341 A1 | 9/2000 |
| EP | 1 024 173 A1 | 8/2000 |
| EP | 2 218 570 A1 | 8/2010 |
| FR | 2 691 826 A1 | 12/1993 |
| FR | 2 917 876 A1 | 12/2008 |
| GB | 2488994 A | 9/2012 |
| JP | 10 211160 A | 8/1998 |
| JP | 2001005378 A | 1/2001 |
| JP | 2009236963 A | 10/2009 |
| JP | 3162161 U | 8/2010 |
| JP | 2013127496 A | 6/2013 |
| MX | PA 02004422 A | 11/2003 |
| PT | 106230 | 9/2013 |
| WO | WO 1994/06109 A1 | 3/1994 |
| WO | WO 1996/042076 A1 | 12/1996 |
| WO | WO 1998/58358 A1 | 12/1998 |
| WO | WO 1999/01074 A1 | 1/1999 |
| WO | WO 2000/36577 A1 | 6/2000 |
| WO | WO 2002/38039 A2 | 5/2002 |
| WO | WO 2002/038039 A3 | 5/2002 |
| WO | WO 2004/032095 A1 | 4/2004 |
| WO | WO 2004/082486 A1 | 9/2004 |
| WO | WO 2005/071639 A1 | 8/2005 |
| WO | WO 2006/083963 A2 | 8/2006 |
| WO | WO 2007/068360 A1 | 6/2007 |
| WO | WO 2008/021720 A2 | 2/2008 |
| WO | WO 2009/000939 A1 | 12/2008 |
| WO | WO 2009/089614 A1 | 7/2009 |
| WO | WO 2010/094730 A1 | 8/2010 |
| WO | WO 2011/035410 A1 | 3/2011 |
| WO | WO 2011/046606 A1 | 4/2011 |
| WO | WO 2011/151304 A1 | 12/2011 |
| WO | WO 2012/149606 A1 | 11/2012 |
| WO | WO 2012/168287 A1 | 12/2012 |
| WO | WO 2012/175993 A1 | 12/2012 |
| WO | WO 2013/048978 A1 | 4/2013 |
| WO | WO 2013/103956 A1 | 7/2013 |
| WO | WO 2014/022815 A1 | 2/2014 |
| WO | WO 2014/093669 A1 | 6/2014 |
| WO | WO 2015/148817 A1 | 10/2015 |
| WO | WO 2016/183412 A1 | 11/2016 |
| WO | WO 2016/201085 A1 | 12/2016 |

OTHER PUBLICATIONS

3D-MED Corporation, "Validated Training Course for Laparoscopic Skills", https://www.3-dmed.com/sites/default/files/product-additional/product-spec/Validated%20Training%20Course%20for%20Laparoscopic%20Skills.docx_.3.pdf , printed Aug. 23, 2016, pp. 1-6.

The International Bureau of WIPO, International Preliminary Report on Patentability for International Application No. PCT/US2016/0032292, entitled "Synthetic Tissue Structures for Electrosurgical Training and Simulation," dated Nov. 23, 2017, 8 pgs.

The International Bureau of WIPO, International Preliminary Report on Patentability for International Application No. PCT/US2016/034591, entitled "Surgical Training Model for Laparoscopic Procedures," dated Dec. 7, 2017, 14 pgs.

The International Bureau of WIPO, International Preliminary Report on Patentability for International Application No. PCT/US2016/036664, entitled "Hysterectomy Model," dated Dec. 21, 2017, 10 pgs.

Society of Laparoendoscopic Surgeons, "Future Technology Session: The Edge of Innovation in Surgery, Space, and Business," http://www.laparoscopytoday.com/endourology/page/2/ , Figure 1B: http://laparoscopy.blogs.com/laparoscopy_today/images/6-1/6-1VlaovicPicB.jpg , Sep. 5-8, 2007, 10 pgs.

European Patent Office, International Search Report for International Application No. PCT/US2011/053859 A3, dated Apr. 5, 2012, entitled "Portable Laparoscopic Trainer," 8 pgs.

European Patent Office, The International Search Report and Written Opinion for International Application No. PCT/US2012/60997, entitled "Simulated Tissue Structure for Surgical Training," dated Mar. 7, 2013, 8 pgs.

European Patent Office, The International Search Report and Written Opinion for International Application No. PCT/US2012/070971, entitled "Advanced Surgical Simulation," dated Mar. 18, 2013, 10 pgs.

Human Patient Simulator, Medical Education Technologies, Inc., http://www.meti.com (1999) all, printed Apr. 12, 2013, 24 pgs.

The International Bureau of WIPO, International Preliminary Report on Patentability and Written Opinion for International Application No. PCT/US2011/053859, entitled "Portable Laparoscopic Trainer," dated Apr. 2, 2013, 9 pgs.

European Patent Office, The International Search Report and Written Opinion for International Application No. PCT/US2013/062363, entitled "Surgical Training Model for Laparoscopic Procedures," dated Jan. 22, 2014, 11 pgs.

European Patent Office, The International Search Report and Written Opinion for International Application No. PCT/US2013/061949, entitled "Surgical Training Model for Laparoscopic Procedures," dated Feb. 17, 2014, 7 pgs.

Anonymous: Realsim Systems—LTS2000, Sep. 4, 2005, pp. 1-2, XP055096193, Retrieved from the Internet: URL:https://web.archive.org/web/2005090403;3030/http://www.realsimsystems.com/exersizes.htm (retrieved on Jan. 14, 2014).

European Patent Office, The International Search Report and Written Opinion for International Application No. PCT/US2013/062269, entitled "Surgical Training Model for Transluminal Procedures," dated Feb. 17, 2014, 8 pgs.

European Patent Office, The International Search Report and Written Opinion for International Application No. PCT/US2013/061557, entitled "Surgical Training Model for Laparoscopic Procedures," dated Feb. 10, 2014, 9 pgs.

European Patent Office, The International Search Report and Written Opinion for International Application No. PCT/US2013/061728, entitled "Surgical Training Model for Laparoscopic Procedures," dated Oct. 18, 2013, 9 pgs.

(56) References Cited

OTHER PUBLICATIONS

Limps and Things, EP Guildford MATTU Hernia Trainer, http://limbsandthings.com/us/products/tep-guildford-mattu-hernia-trainer/, printed May 29, 2014, 11 pgs.
Simulab, Hernia Model, http://www.simulab.com/product/surgery/open/hernia model, printed printed May 29, 2014, 4 pgs.
McGill Laparoscopic Inguinal Hernia Simulator, Novel Low-Cost Simulator for Laparoscopic Inguinal Hernia Repair, Feb. 8, 2011, 1 pg.
University of Wisconsin-Madison Biomedical Engineering, Inguinal Hernia Model, http://bmedesicin.engr.wisc.edu/projects/s10/hernia_model/, printed May 29, 2014, 62 pgs.
The International Bureau of WIPO, International Preliminary Report on Patentability for International Application No. PCT/US2012/070971, entitled "Advanced Surgical Simulation," dated Jun. 24, 2014, 7 pgs.
European Patent Office, The International Search Report and Written Opinion of the International Searching Authority for International Application No. PCT/US2014/038195, entitled "Hernia Model", dated Oct. 15, 2014, 20 pgs.
European Patent Office, The International Search Report and Written Opinion of the International Searching Authority for International Application No. PCT/US2014/048027, entitled "First Entry Model", dated Oct. 17, 2014, 10 pgs.
The International Bureau of WIPO, International Preliminary Report on Patentability for International Application No. PCT/US2012/060997, entitled "Simulated Tissue Structure for Surgical Training" dated Apr. 22, 2014, 6 pgs.
European Patent Office, The International Search Report and Written Opinion for International Application No. PCT/US2014/019840, entitled "Advanced Surgical Simulation Constructions and Methods," dated Jul. 4, 2014, 8 pgs.
Kurashima, et al, "A tool for training and evaluation of Laparoscopic inguinal hernia repair; the Global Operative Assessment of Laparoscopic Skills-Groin Hernia" American Journal of Surgery, Paul Hoeber, New York, NY, US vol. 201, No. 1, Jan. 1, 2011, pp. 54-61 XP027558745.
European Patent Office, The International Search Report and Written Opinion for International Application No. PCT/US2014/042998, entitled "Gallbladder Model," dated Jan. 7, 2015, 20 pgs.
The International Bureau of WIPO, International Preliminary Report on Patentability, for PCT application No. PCT/US2013/053497, entitled Simulated Stapling and Energy Based Ligation for Surgical Training, dated Feb. 12, 2015, 6 pgs.
The International Bureau of WIPO, International Preliminary Report on Patentability for International Application No. PCT/US2013/062363, entitled "Surgical Training Model for Laparoscopic Procedures," dated Apr. 9, 2015, 9 pgs.
The International Bureau of WIPO, International Preliminary Report on Patentability for International Application No. PCT/US2013/062269, entitled "Surgical Training Model for Laparoscopic Procedures," dated Apr. 9, 2015, 6 pgs.
The International Bureau of WIPO, International Preliminary Report on Patentability for International Application No. PCT/US2013/061557, entitled "Surgical Training Model for Laparoscopic Procedures," dated Apr. 9, 2015, 6 pgs.
The International Bureau of WIPO, International Preliminary Report on Patentability for International Application No. PCT/US2013/061728, entitled "Surgical Training Model for Laparoscopic Procedures," dated Apr. 9, 2015, 7 pgs.
The International Bureau of WIPO, International Preliminary Report on Patentability for International Application No. PCT/US2013/061949, entitled "Surgical Training Model for Laparoscopic Procedures," dated Apr. 9, 2015, 6 pgs.
The International Bureau of WIPO, International Preliminary Report on Patentability for International Application No. PCT/US2014/019840, entitled "Simulated Tissue Structure for Surgical Training," dated Sep. 11, 2015, 8 pgs.
European Patent Office, The International Search Report and Written Opinion for International Application No. PCT/US2015/020574, entitled "Advanced First Entry Model for Surgical Simulation," dated Jun. 1, 2015, 12 pgs.
European Patent Office, The International Search Report and Written Opinion for International Application No. PCT/US2015/022774, entitled "Simulated Dissectible Tissue," dated Jun. 11, 2015, 13 pgs.
Anonymous: Silicone rubber-from Wikipedia, the free encyclopedia, pp. 1-6, XP055192375, Retrieved from the Internet: URL:http://en.wikipedia.org/w.index.php?title=Silicone_rubber&oldid=596456058 (retrieved on May 29, 2015).
Lamouche, et al., "Review of tissue simulating phantoms with controllable optical, mechanical and structural properties for use in optical coherence tomography," Biomedical Optics Express, Jun. 1, 2012, 18 pgs., vol. 3, No. 6.
The International Bureau of WIPO, International Preliminary Report on Patentability for International Application No. PCT/US2014/038195, entitled "Hernia Model," dated Nov. 26, 2015, 16 pgs.
The International Bureau of WIPO, International Preliminary Report on Patentability for International Application No. PCT/US2014/042998, entitled "Gallbladder Model," dated Dec. 30, 2015, 15 pgs.
European Patent Office, International Search Report and Written Opinion for International Application No. PCT/US2013/053497, titled "Simulated Stapling and Energy Based Ligation for Surgical Training," dated Nov. 5, 2013, 8 pgs.
The International Bureau of WIPO, International Preliminary Report on Patentability for International Application No. PCT/US2014/048027, entitled "First Entry Model," dated Feb. 4, 2016, 8 pgs.
European Patent Office, International Search Report and Written Opinion for International Application No. PCT/US2015/059668, entitled "Simulated Tissue Models and Methods," dated Apr. 26, 2016, 20 pgs.
Australian Patent Office, Patent Examination Report No. 1 for Australian Application No. 2012358851, titled "Advanced Surgical Simulation," dated May 26, 2016, 3 pgs.
Miyazaki Enterprises, "Miya Model Pelvic Surgery Training Model and Video," www.miyazakienterprises, printed Jul. 1, 2016, 1 pg.
European Patent Office, International Search Report and Written Opinion for International Application No. PCT/US2016/032292, entitled "Synthetic Tissue Structures for Electrosurgical Training and Simulation," dated Jul. 14, 2016, 11 pgs.
European Patent Office, International Search Report and Written Opinion for International Application No. PCT/US2016/018697, entitled "Simulated Tissue Structures and Methods," dated Jul. 14, 2016, 21 pgs.
European Patent Office, International Search Report and Written Opinion for International Application No. PCT/US2016/034591, entitled "Surgical Training Model for Laparoscopic Procedures," dated Aug. 8, 2016, 18 pgs.
European Patent Office, The International Search Report and Written Opinion of the International Searching Authority for International Application No. PCT/US2016/036664, entitled "Hysterectomy Model", dated Aug. 19, 2016, 15 pgs.
The International Bureau of WIPO, International Preliminary Report on Patentability for International Application No. PCT/US2015/020574, entitled "Advanced First Entry Model for Surgical Simulation," dated Sep. 22, 2016, 9 pgs.
European Patent Office, The International Search Report and Written Opinion of the International Searching Authority for International Application No. PCT/US2016/0043277 titled "Appendectomy Model", dated Oct. 4, 2016, 12 pgs.
The International Bureau of WIPO, International Preliminary Report on Patentability for International Application No. PCT/US2015/022774, titled "Simulated Dissectible Tissue," dated Oct. 6, 2016, 9 pgs.
European Patent Office, The International Search Report and Written Opinion of the International Searching Authority for International Application No. PCT/US2016/041852 titled "Simulated Dissectible Tissue", dated Oct. 13, 2016, 12 pgs.
European Patent Office, Invitation to Pay Additional Fees for International Application No. PCT/US2016/062669, titled "Simulated Dissectible Tissue", dated Feb. 10, 2017, 8 pgs.
European Patent Office, The International Search Report and Written Opinion of the International Searching Authority for Interna-

(56) References Cited

OTHER PUBLICATIONS tional Application No. PCT/US2016/055148 titled "Hysterectomy Model", dated Feb. 28, 2017, 12 pgs.
European Patent Office, The International Search Report and Written Opinion of the International Searching Authority for International Application No. PCT/US2016/062669 titled "Simulated Dissectible Tissue", dated Apr. 5, 2017, 19 pgs.
European Patent Office, Examination Report for European Application No. 14733949.3 titled "Gallbladder Model," dated Dec. 21, 2016, 6 pgs.
European Patent Office, The International Search Report and Written Opinion of the International Searching Authority for International Application No. PCT/US2017/020389 titled "Simulated Tissue Cartridge", dated May 24, 2017, 13 pgs.
The International Bureau of WIPO, International Preliminary Report on Patentability for International Application No. PCT/US2015/059668, entitled "Simulated Tissue Models and Methods," dated May 26, 2017, 16 pgs.
The International Bureau of WIPO, International Preliminary Report on Patentability for International Application No. PCT/US2016/018697, entitled "Simulated Tissue Structures and Methods," dated Aug. 31, 2017, 14 pgs.
3D-MED Corporation, "Loops and Wire #1," https://www.3-dmed.com/product/loops-and-wire-1 , printed Aug. 23, 2016, 4 pgs.
Barrier, et al., "A Novel and Inexpensive Vaginal Hysterectomy Simulatory, "Simulation in Healthcare: The Journal of the Society for Simulation in Healthcare, vol. 7, No. 6, Dec. 1, 2012, pp. 374-379.
European Patent Office, The International Search Report and Written Opinion for International Application No. PCT/US2018/018036, entitled "Laparoscopic Training System," dated Jun. 8, 2018, 13 pgs.
European Patent Office, The International Search Report and Written Opinion for International Application No. PCT/US2018/018895, entitled "Synthetic Tissue Structures for Electrosurgical Training and Simulation," dated May 17, 2018, 12 pgs.
The International Bureau of WIPO, International Preliminary Report on Patentability for International Application No. PCT/US2016/062669, entitled "Simulated Dissectible Tissue," dated May 31, 2018, 11 pgs.
The International Bureau of WIPO, International Preliminary Report on Patentability for International Application No. PCT/US2016/041852, entitled "Simulated Dissectible Tissue," dated Jan. 25, 2018, 12 pgs.
European Patent Office, Extended European Search Report for European Patent Application No. EP 17202365.7, titled "Gallbladder Model", dated Jan. 31, 2018, 8 pgs.
The International Bureau of WIPO, International Preliminary Report on Patentability for International Application No. PCT/US2016/043277, entitled "Appendectomy Model," dated Feb. 1, 2018, 9 pgs.
European Patent Office, The International Search Report and Written Opinion for International Application No. PCT/US2017/039113, entitled "Simulated Abdominal Wall," dated Aug. 7, 2017, 13 pgs.

\* cited by examiner

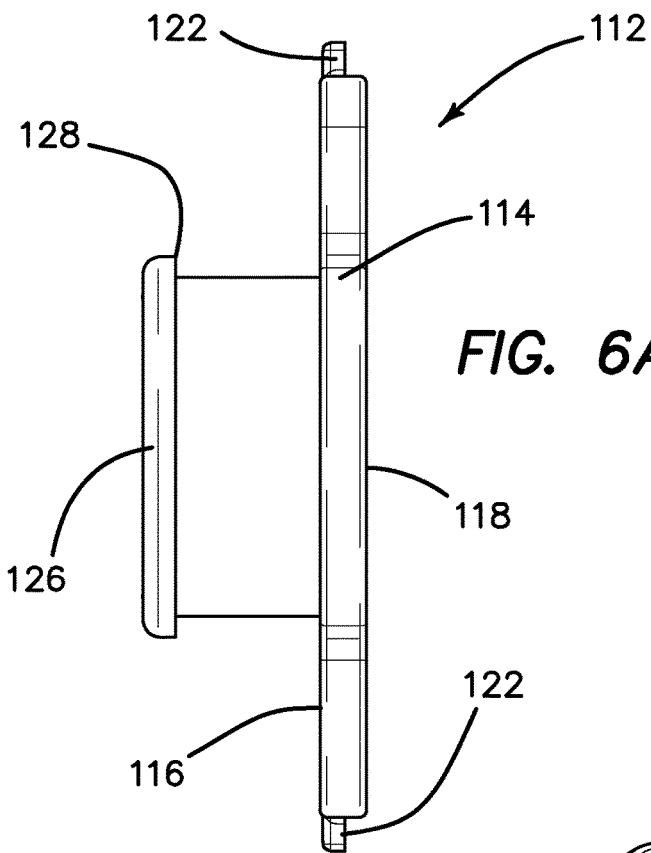
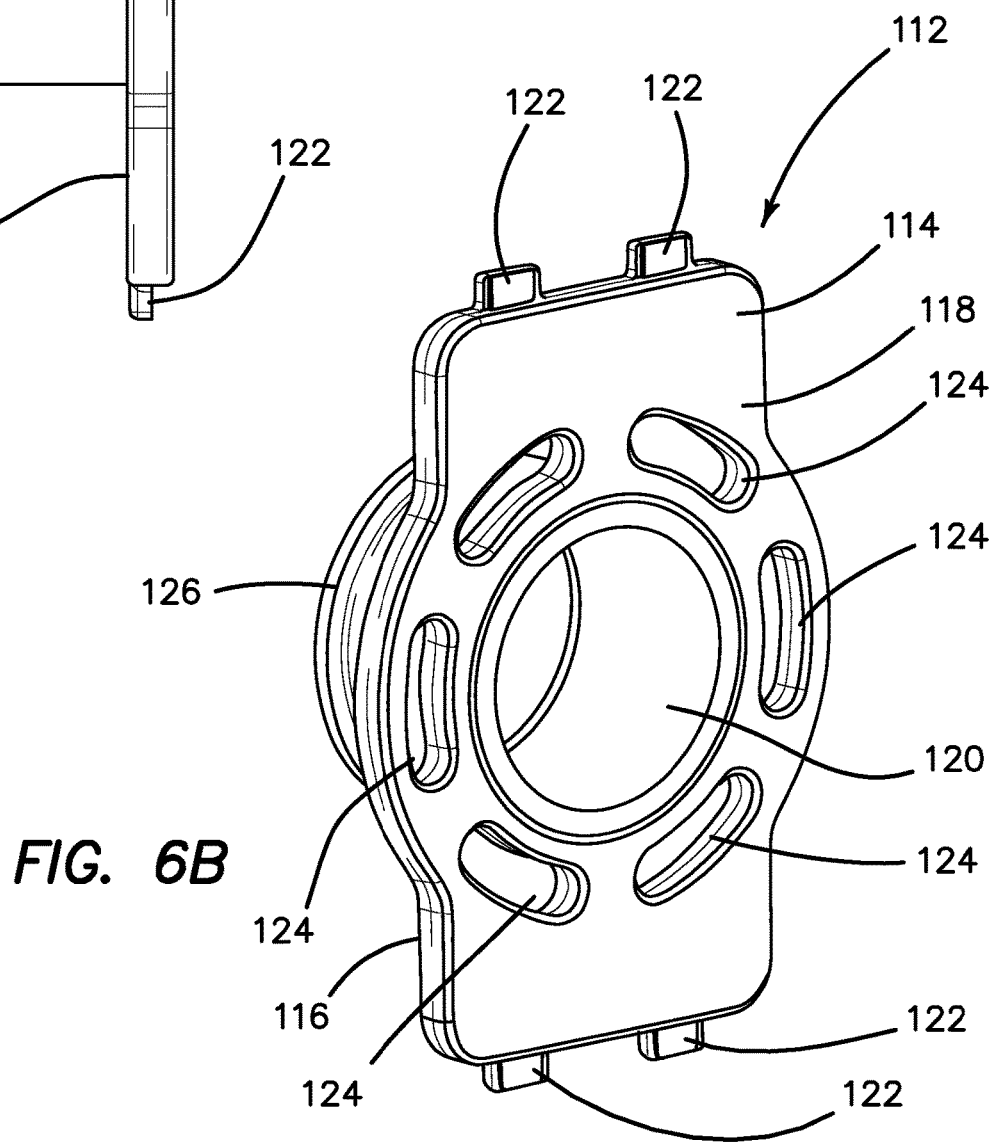

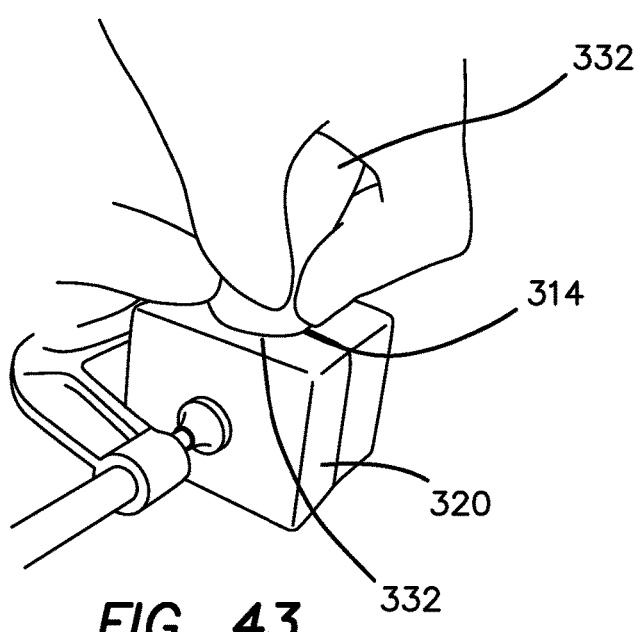
FIG. 43
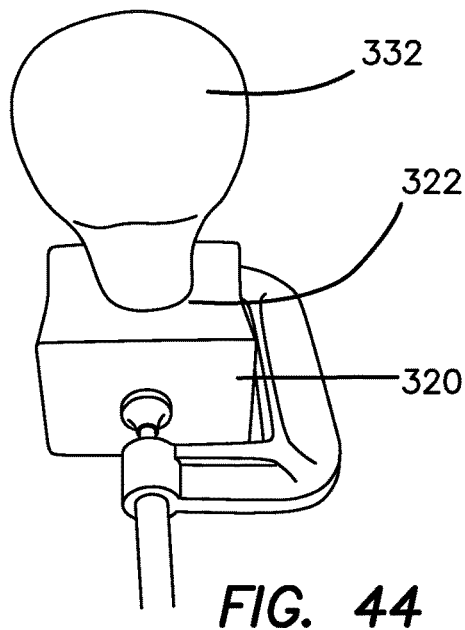
FIG. 44
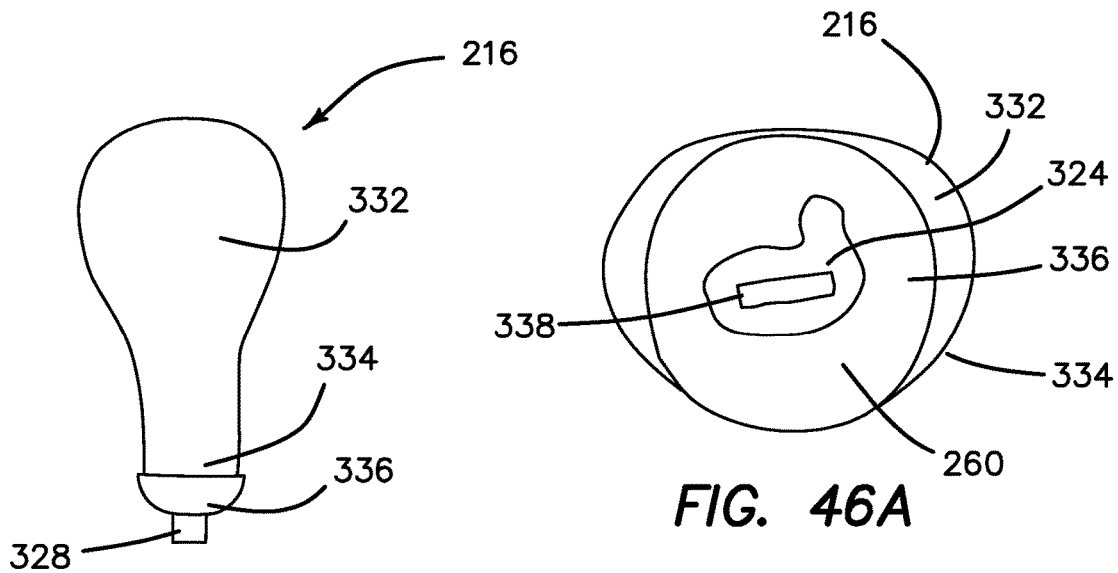
FIG. 45
FIG. 46A
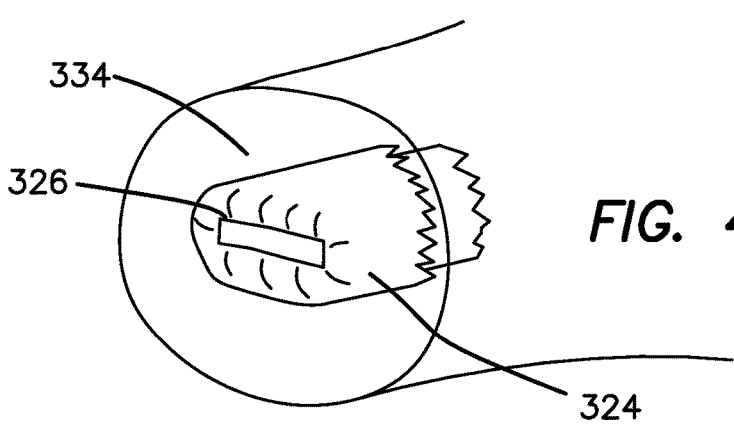
FIG. 46B

HYSTERECTOMY MODEL

CROSS-REFERENCE TO RELATED APPLICATION

This patent application is a continuation of International Patent Application No. PCT/US2016/055148 entitled "Hysterectomy model" filed on Oct. 3, 2016 which claims priority to and benefit of U.S. Provisional Patent Application Ser. No. 62/236,756 entitled "Hysterectomy model" filed on Oct. 2, 2015 and U.S. Provisional Patent Application Ser. No. 62/254,477 entitled "Hysterectomy model" filed on Nov. 12, 2015 incorporated herein by reference in their entirety.

FIELD OF THE INVENTION

This application is generally related to surgical training tools, and in particular, to simulated tissue structures and models for teaching and practicing various surgical techniques and procedures related but not limited to laparoscopic, endoscopic and minimally invasive surgery.

BACKGROUND OF THE INVENTION

Medical students as well as experienced doctors learning new surgical techniques must undergo extensive training before they are qualified to perform surgery on human patients. The training must teach proper techniques employing various medical devices for cutting, penetrating, clamping, grasping, stapling, cauterizing and suturing a variety of tissue types. The range of possibilities that a trainee may encounter is great. For example, different organs and patient anatomies and diseases are presented. The thickness and consistency of the various tissue layers will also vary from one part of the body to the next and from one patient to another. Different procedures demand different skills. Furthermore, the trainee must practice techniques in various anatomical environs that are influenced by factors such as the size and condition of the patient, the adjacent anatomical landscape and the types of targeted tissues and whether they are readily accessible or relatively inaccessible.

Numerous teaching aids, trainers, simulators and model organs are available for one or more aspects of surgical training. However, there is a need for models or simulated tissue elements that are likely to be encountered in and that can be used for practicing endoscopic and laparoscopic, minimally invasive, transluminal surgical procedures. In laparoscopic surgery, a trocar or cannula is inserted to access a body cavity and to create a channel for the insertion of a camera such as a laparoscope. The camera provides a live video feed capturing images that are then displayed to the surgeon on one or more monitors. At least one additional small incision is made through which another trocar/cannula is inserted to create a pathway through which surgical instruments can be passed for performing procedures observed on the monitor. The targeted tissue location such as the abdomen is typically enlarged by delivering carbon dioxide gas to insufflate the body cavity and create a working space large enough to accommodate the scope and instruments used by the surgeon. The insufflation pressure in the tissue cavity is maintained by using specialized trocars. Laparoscopic surgery offers a number of advantages when compared with an open procedure. These advantages include reduced pain, reduced blood and shorter recovery times due to smaller incisions.

Laparoscopic or endoscopic minimally invasive surgery requires an increased level of skill compared to open surgery because the target tissue is not directly observed by the clinician. The target tissue is observed on monitors displaying a portion of the surgical site that is accessed through a small opening. Therefore, clinicians need to practice visually determining tissue planes, three-dimensional depth perception on a two-dimensional viewing screen, hand-to-hand transfer of instruments, suturing, precision cutting and tissue and instrument manipulation. Typically, models simulating a particular anatomy or procedure are placed in a simulated pelvic trainer where the anatomical model is obscured from direct visualization by the practitioner. Ports in the trainer are employed for passing instruments to practice techniques on the anatomical model hidden from direct visualization. Simulated pelvic trainers provide a functional, inexpensive and practical means to train surgeons and residents the basic skills and typical techniques used in laparoscopic surgery such as grasping, manipulating, cutting, tying knots, suturing, stapling, cauterizing as well as how to perform specific surgical procedures that utilized these basic skills. Simulated pelvic trainers are also effective sales tools for demonstrating medical devices required to perform these laparoscopic procedures.

One procedure is a hysterectomy in which the uterus is removed. The hysterectomy may be performed vaginally extracting the uterus through the vaginal canal or abdominally through a small incision in the abdomen. The vaginal hysterectomy is historically hard to train on as the field of view is limited. Unlike laparoscopic procedures, there is no camera that is projecting the surgery onto a screen and unlike open procedures there is not a wide incision that can be viewed by multiple people. As such, the best way to teach a vaginal hysterectomy is through a simulated model. Therefore, there is a need for model for training hysterectomy procedures.

SUMMARY OF THE INVENTION

According to one aspect of the invention, a surgical simulator for surgical training is provided. The surgical simulator includes a frame having an inner surface and an outer surface defining a frame wall therebetween. The inner surface defines a lumen extending along a longitudinal axis of the frame. The lumen includes at least one of a proximal opening and a distal opening. The frame is configured to removably receive at least one artificial tissue structure within the lumen such that the at least one artificial tissue structure is at least partially suspended within the lumen and at least partially encompassed by the frame wall along the lumen. The at least one artificial tissue structure is suspended with fasteners configured to connect the at least one artificial tissue structure to the frame wall. The lumen has a cross-sectional area taken perpendicular to the longitudinal axis that progressively increases from the proximal end to the distal end.

According to another aspect of the invention, a surgical simulator for surgical training is provided. The frame includes an inner surface and an outer surface defining a frame wall therebetween. The inner surface defines a lumen extending along the longitudinal axis. The lumen has at least one of a proximal opening and a distal opening and a top and a bottom. The surgical simulator further includes an artificial uterus and an artificial vaginal canal defining an opening at the proximal end and connected to the artificial uterus at the distal end. The surgical simulator further includes an artificial rectum having a lumen defining a proximal opening.

The surgical simulator further includes an artificial bladder. The surgical simulator further includes an artificial bladder. The surgical simulator further includes a first planar sheet of silicone having a first surface and a second surface defining a substantially uniform thickness therebetween. The surgical simulator further includes a second planar sheet of silicone having a first surface and a second surface. The artificial uterus, artificial vaginal canal, and artificial bladder are connected to the first surface of the first planar sheet and the first planar sheet is connected to the top of the lumen. The artificial uterus and artificial vaginal canal are connected to the artificial rectum by the second planar sheet. The artificial rectum is connected to the bottom of the frame.

According to another aspect of the invention, an artificial uterus for surgical training is provided. The artificial uterus includes a bulbous body at a distal end and a simulated cervix at a proximal end. The simulated cervix is made of silicone and defines an opening at the proximal end. The simulated cervix includes a reinforcement made of mesh material. The mesh material has a plurality of interwoven filaments forming a tubular structure having a first end and a second end. The tubular structure forms a first layer of mesh material and is folded to create a second layer of mesh material. The fold is formed at a proximal end such that the first end and the second end of the tubular structure are distal to the fold. The second layer of mesh material is substantially coaxial with the tubular first layer of mesh material. The folded tubular structure is embedded in silicone of the simulated cervix at the proximal end.

A surgical simulator for surgical training is provided. The simulator includes a frame defining an enclosure and a simulated tissue model located inside the enclosure. The simulated tissue model is adapted for practicing a number of surgical procedures including but not limited to transanal excisions and transvaginal hysterectomies. The simulated tissue model includes one more components and is interchangeably connected to the frame with fasteners configured to pass through apertures in the frame to suspend the simulated tissue model within the frame. The enclosure of the frame is increasingly laterally constricted along the longitudinal axis to progressively increase the confinement of the components of the simulated tissue model.

According to another aspect of the invention, a surgical simulator for surgical training is provided. The surgical simulator includes a rigid frame having an inner surface and an outer surface defining a frame wall therebetween. The inner surface defines a passageway extending along a longitudinal axis. The passageway has at least one of a proximal opening and a distal opening. An artificial tissue structure made of silicone is provided and at least one fastener is connected to the artificial tissue structure. The at least one fastener is configured to removably connect the artificial tissue structure to the frame. The frame includes one or more apertures and the fasteners are configured to pass through the one or more apertures to connect the artificial tissue structure to the frame.

According to another aspect of the invention, a surgical simulator for surgical training is provided. The simulator includes a frame defining an enclosure and a simulated tissue model located inside the enclosure. The simulated tissue model is adapted for practicing a number of surgical procedures including but not limited to transanal excisions, transvaginal hysterectomies, and other laparoscopic, minimally invasive and open procedures. The simulated tissue model includes one more components. The model is interchangeably connected to the frame with fasteners configured to pass through apertures in the frame to suspend the simulated tissue model within the frame. The enclosure of the frame is increasingly laterally constricted along the longitudinal axis to progressively increase the confinement of the components of the simulated tissue model. The increased confinement provides reduced pendulation of the model components.

BRIEF DESCRIPTION OF THE DRAWINGS

FIG. 6A is a side view of a transvaginal adapter according to the present invention.

FIG. 6B is a top perspective view of a transvaginal adapter according to the present invention.

FIG. 43 is a top perspective view of a uterine form being inserted into a well of a cervix mold while being squeezed according to the present invention.

FIG. 44 is a top perspective view of a uterine form inside a well of a cervix mold according to the present invention.

FIG. 45 is a top perspective view of a simulated uterus with a post according to the present invention.

FIG. 46A is a proximal end view of a simulated uterus according to the present invention.

FIG. 46B is a top perspective, sectional view of a proximal end of a simulated uterus according to the present invention.

DETAILED DESCRIPTION OF THE INVENTION

Figure 1:
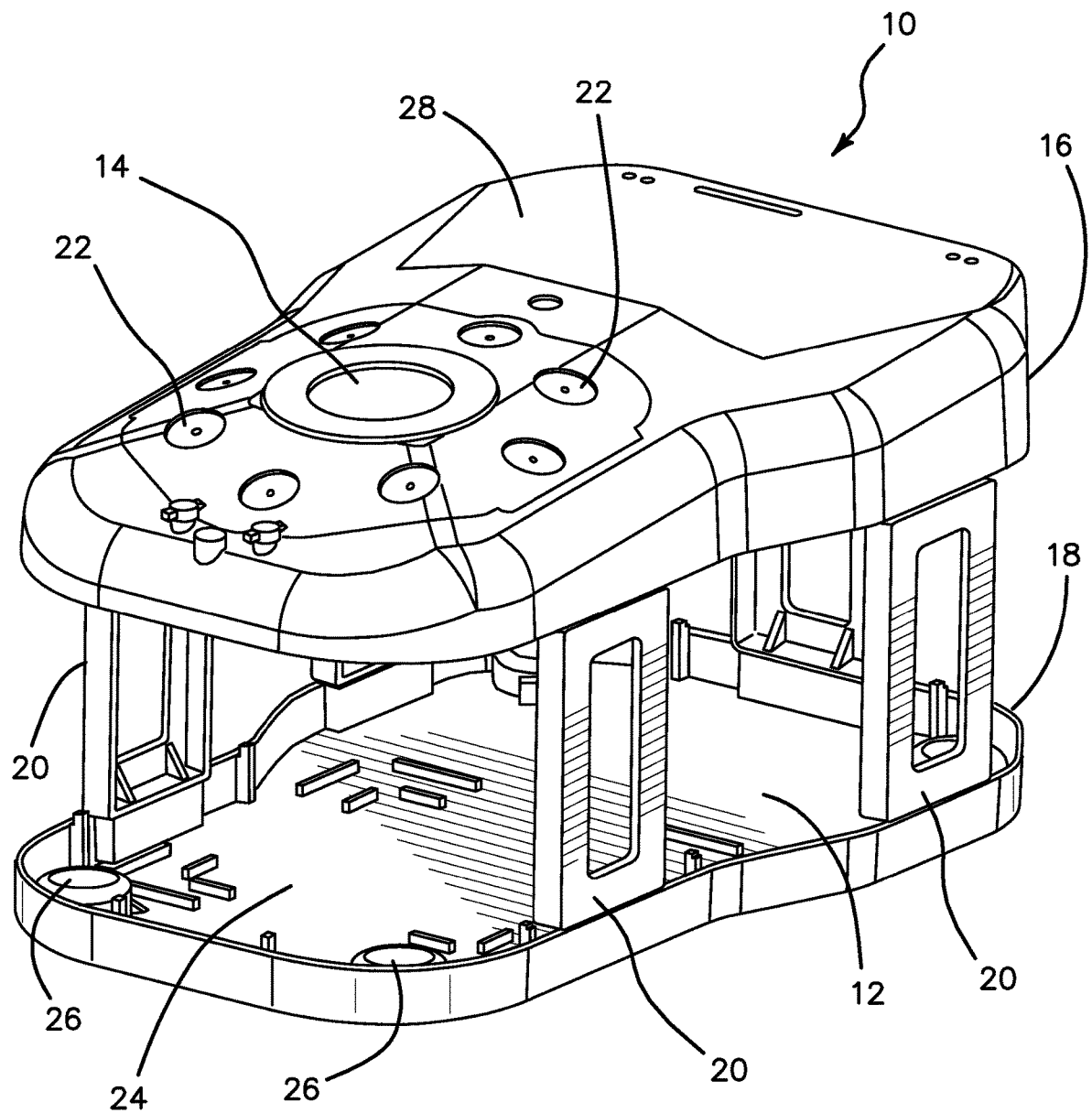
FIG. 1 is a top perspective view of a surgical training device according to the present invention.

A surgical training device 10 that is configured to mimic the torso of a patient such as the abdominal region is shown in FIG. 1. The surgical training device 10 provides a body cavity 12 substantially obscured from the user for receiving simulated or live tissue or model organs or training models of the like described in this invention. The body cavity 12 is accessed via a tissue simulation region 14 that is penetrated by the user employing devices to practice surgical techniques on the tissue or practice model found located in the body cavity 12. Although the body cavity 12 is shown to be accessible through a tissue simulation region, a hand-assisted access device or single-site port device may be alternatively employed to access the body cavity 12. An exemplary surgical training device is described in U.S. patent application Ser. No. 13/248,449 entitled "Portable Laparoscopic Trainer" filed on Sep. 29, 2011 and incorporated herein by reference in its entirety. The surgical training device 10 is particularly well suited for practicing laparoscopic or other minimally invasive surgical procedures.

Still referencing FIG. 1, the surgical training device 10 includes a top cover 16 connected to and spaced apart from a base 18 by at least one leg 20. FIG. 1 shows a plurality of legs 20. The surgical training device 10 is configured to mimic the torso of a patient such as the abdominal region. The top cover 16 is representative of the anterior surface of the patient and the space 12 between the top cover 16 and the base 18 is representative of an interior of the patient or body cavity where organs reside. The surgical trainer 10 is a useful tool for teaching, practicing and demonstrating various surgical procedures and their related instruments in simulation of a patient undergoing a surgical procedure. Surgical instruments are inserted into the cavity 12 through the tissue simulation region 14 as well as through pre-established apertures 22 in the top cover 16. Various tools and techniques may be used to penetrate the top cover 16 to perform mock procedures on simulated organs or practice models placed between the top cover 16 and the base 18. The base 18 includes a model-receiving area 24 or tray for staging or holding a simulated tissue model or live tissue. The model-receiving area 24 of the base 18 includes frame-like elements for holding the model (not shown) in place. To help retain a simulated tissue model or live organs on the base 18, a clip attached to a retractable wire is provided at locations 26. The retractable wire is extended and then clipped to hold the tissue model in position substantially beneath the tissue simulation region 14. Other means for retaining the tissue model include a patch of hook-and-loop type fastening material (VELCRO®) affixed to the base 18 in the model receiving area 24 such that it is removably connectable to a complementary piece of hook-and-loop type fastening material (VELCRO®) affixed to the model.

A video display monitor 28 that is hinged to the top cover 16 is shown in a closed orientation in FIG. 1. The video monitor 28 is connectable to a variety of visual systems for delivering an image to the monitor. For example, a laparoscope inserted through one of the pre-established apertures 22 or a webcam located in the cavity and used to observe the simulated procedure can be connected to the video monitor 28 and/or a mobile computing device to provide an image to the user. Also, audio recording or delivery means may also be provided and integrated with the trainer 10 to provide audio and visual capabilities. Means for connecting a portable memory storage device such as a flash drive, smart phone, digital audio or video player, or other digital mobile device is also provided, to record training procedures and/or play back pre-recorded videos on the monitor for demonstration purposes. Of course, connection means for providing an audio visual output to a screen larger than the monitor is provided. In another variation, the top cover 10 does not include a video display but includes means for connecting with a laptop computer, a mobile digital device or tablet and connecting it by wire or wirelessly to the trainer.

When assembled, the top cover 16 is positioned directly above the base 18 with the legs 20 located substantially around the periphery and interconnected between the top cover 16 and base 18. The top cover 16 and base 18 are substantially the same shape and size and have substantially the same peripheral outline. The internal cavity is partially or entirely obscured from view. In the variation shown in FIG. 1, the legs include openings to allow ambient light to illuminate the internal cavity as much as possible and also to advantageously provide as much weight reduction as possible for convenient portability. The top cover 16 is removable from the legs 20 which in turn are removable or collapsible via hinges or the like with respect to the base 18. Therefore, the unassembled trainer 10 has a reduced height that makes for easier portability. In essence, the surgical trainer 10 provides a simulated body cavity 12 that is obscured from the user. The body cavity 12 is configured to receive at least one surgical model accessible via at least one tissue simulation region 14 and/or apertures 22 in the top cover 16 through which the user may access the models to practice laparoscopic or endoscopic minimally invasive surgical techniques.

Figure 2:
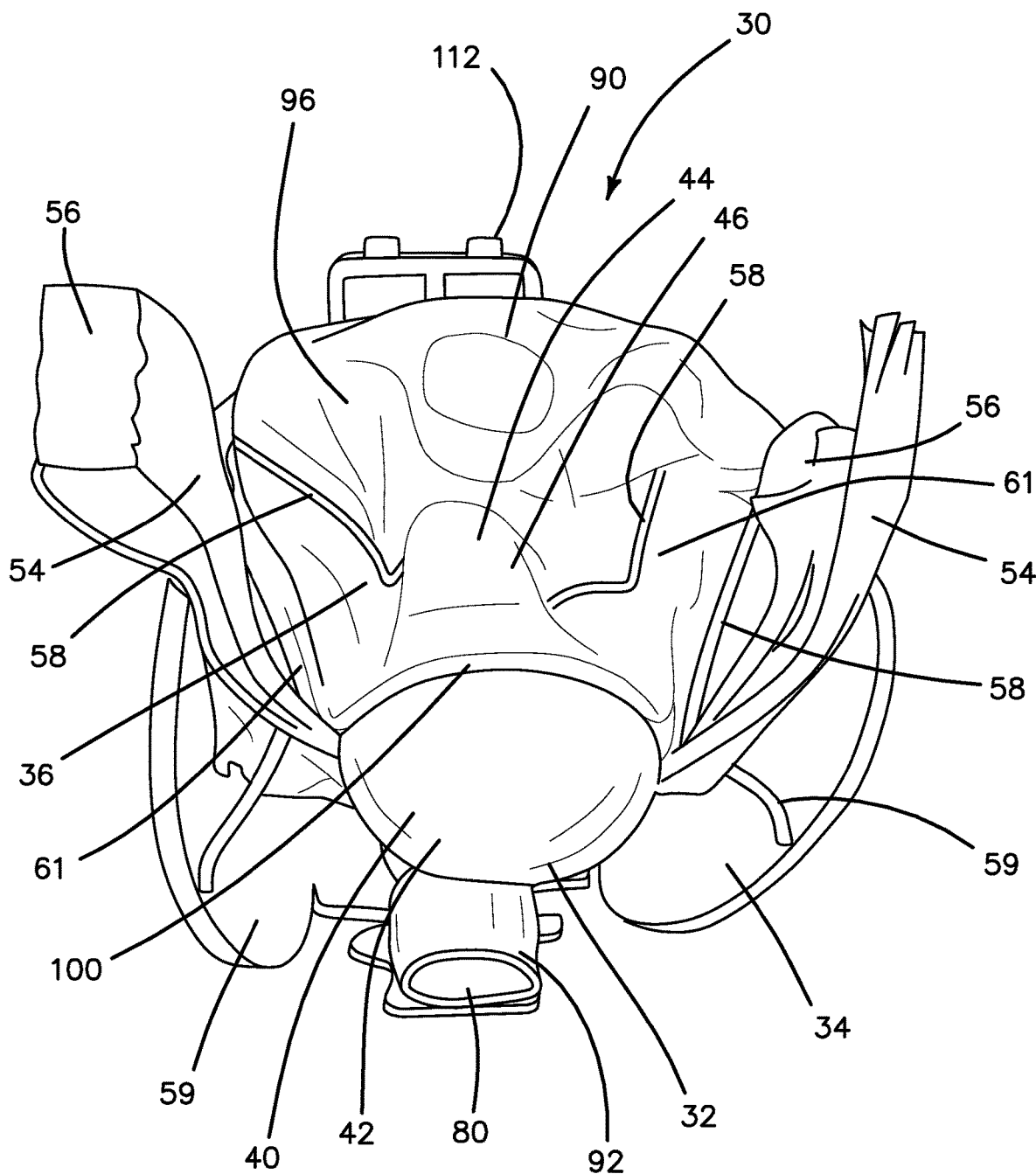
FIG. 2 is an antero-cephalad, top perspective view of a model according to the present invention.
Figure 4A:
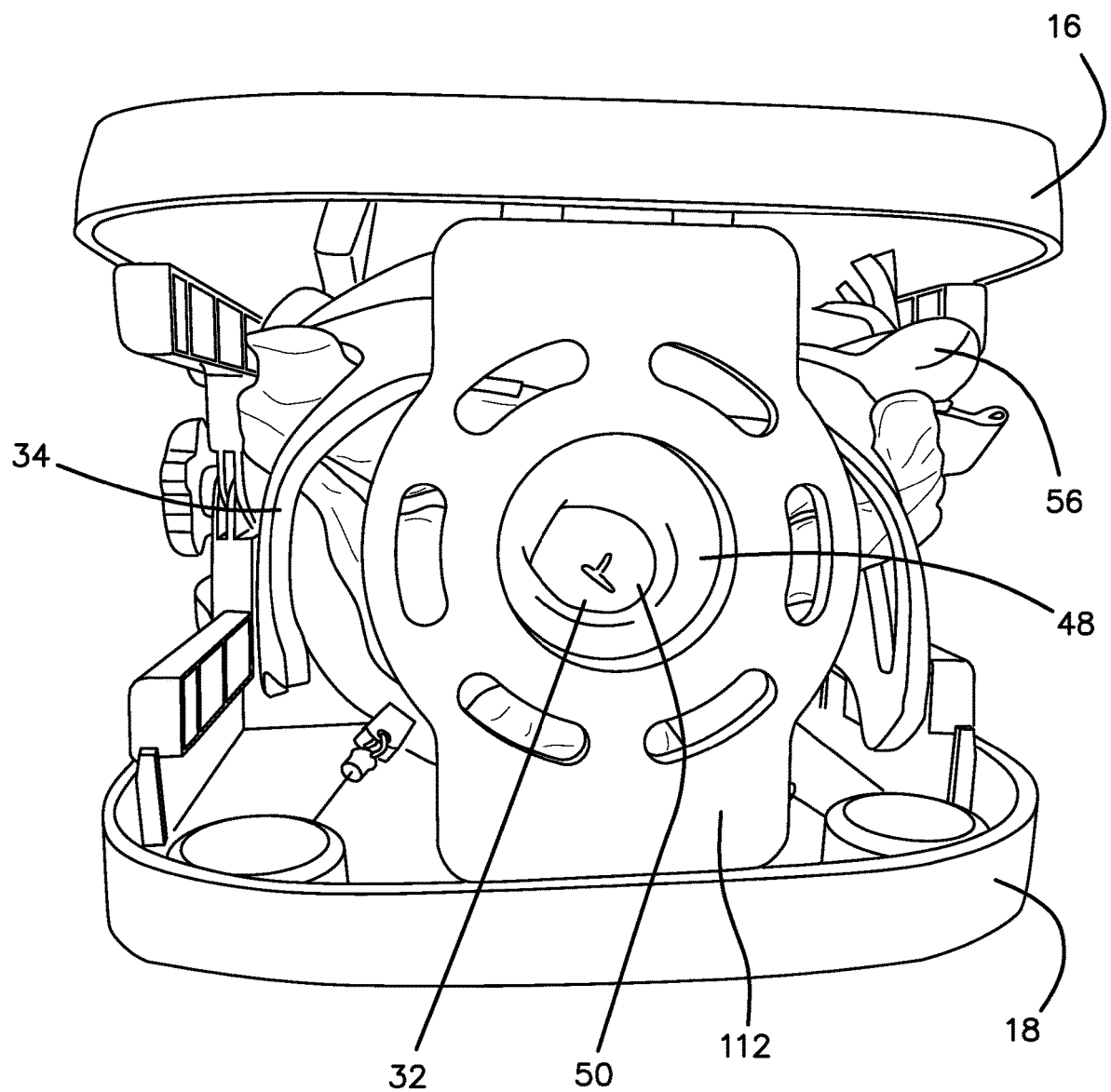
FIG. 4A is a caudal end view of a model inside a surgical training device according to the present invention.
Figure 4B:
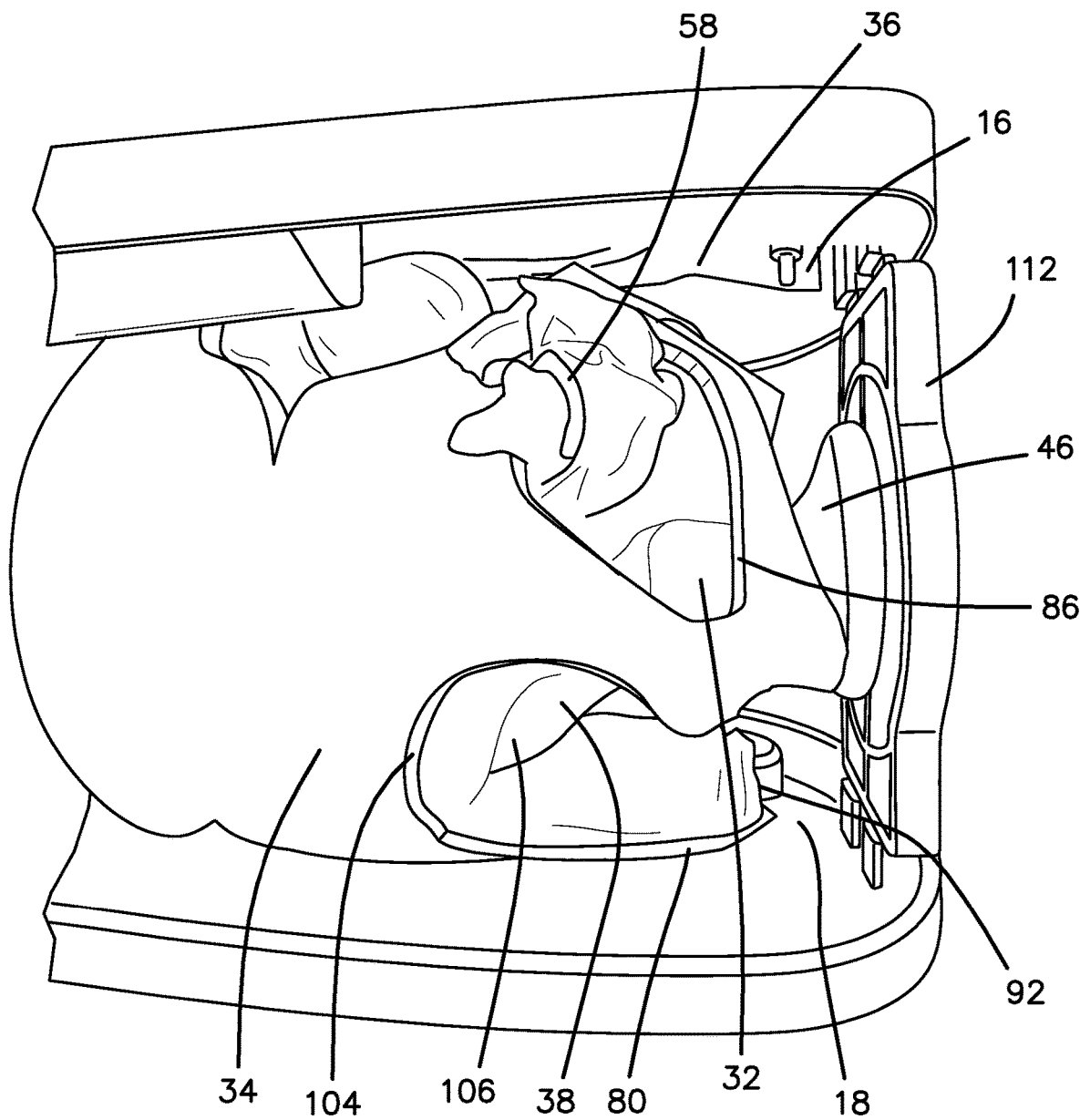
FIG. 4B is a lateral side view of a model inside a surgical training device according to the present invention.
Figure 4C:
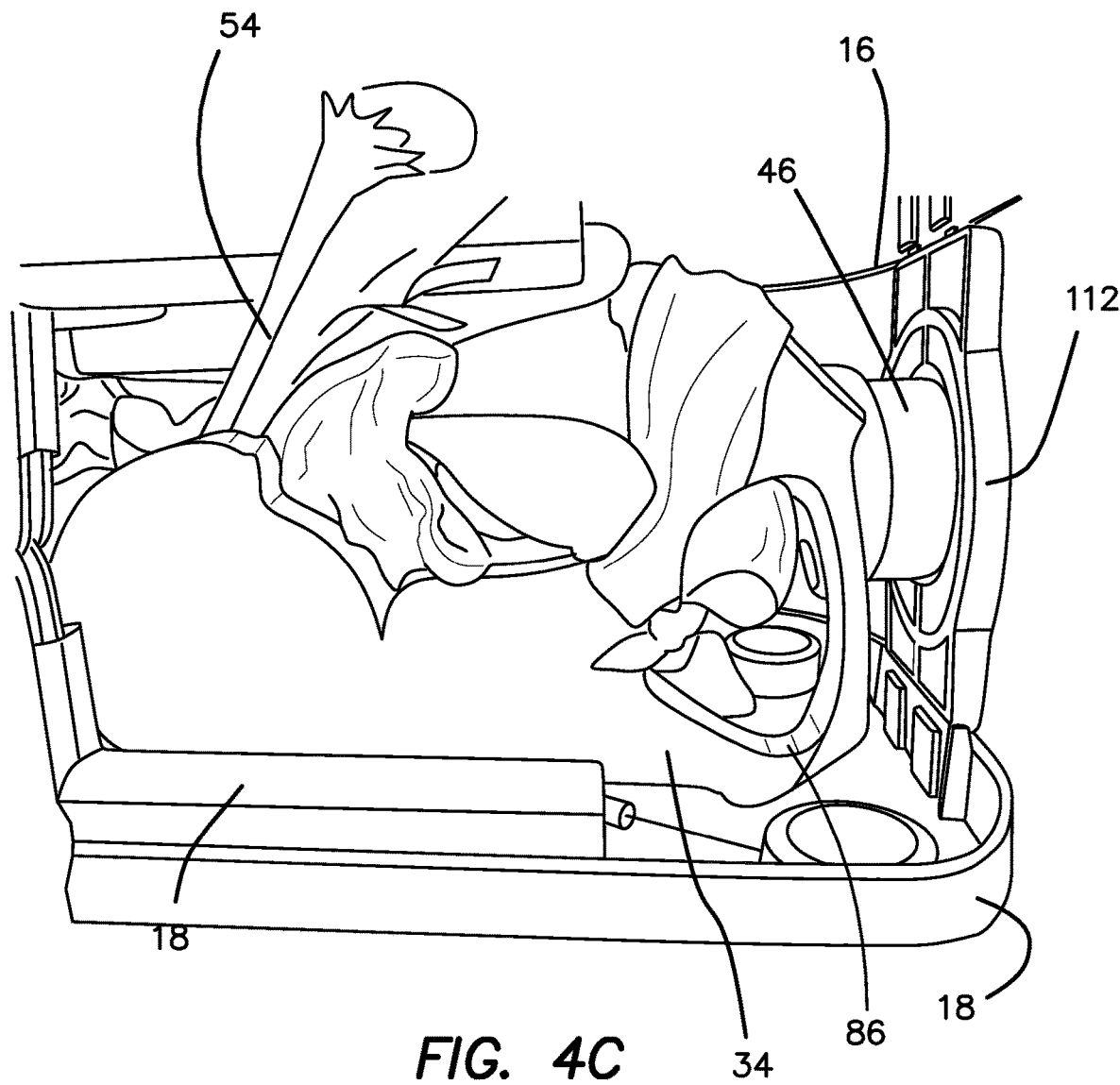
FIG. 4C is a lateral side view of a model inside a surgical training device according to the present invention.

A model 30 for practicing hysterectomies and, in particular, for practicing vaginal hysterectomies according to the present invention is shown in FIG. 2. The model 30 is configured to be placed inside the surgical training device 10 described above or other similar surgical trainer. The model 30 includes a simulated uterus 32 connected to a frame 34 with a first sheet 36 and a second sheet 38. The simulated uterus 32 includes a bulbous portion 40 defining a hollow simulated uterine cavity 42. The bulbous portion 40 is connected to a tubular portion 44 defining a vaginal canal 46 having an opening 48. The simulated uterus 32 further includes a simulated cervix 50 (shown in FIG. 4A) located inside the simulated uterus 32 in a location substantially between the uterine cavity 42 and the vaginal canal 46. The simulated cervix 50 includes a slit 52. The simulated cervix 50 is made of a solid, high durometer silicone.

Figure 4D:
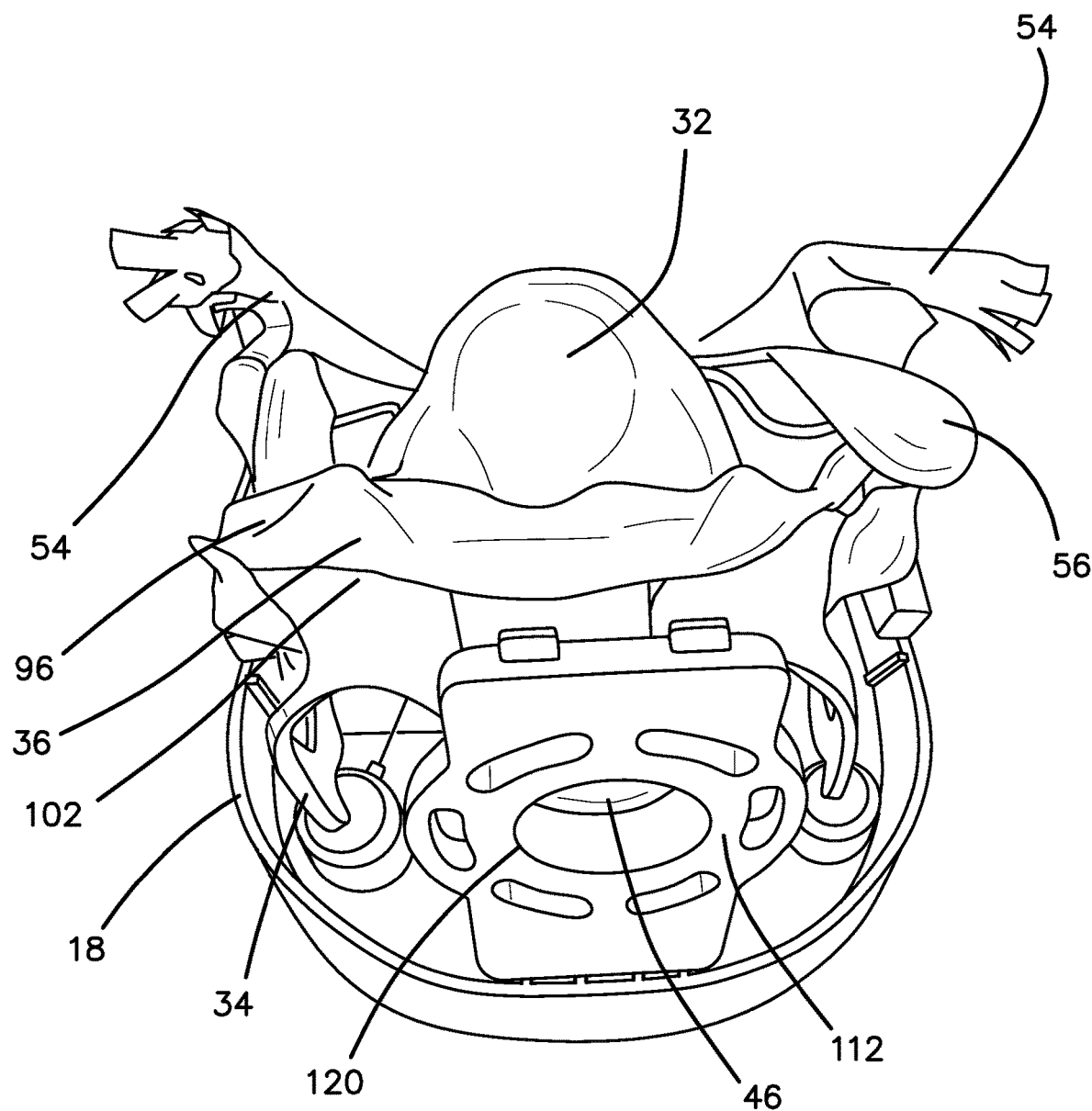
FIG. 4D is an antero-caudal, top perspective view of a model inside a surgical training device according to the present invention.
Figure 4E:
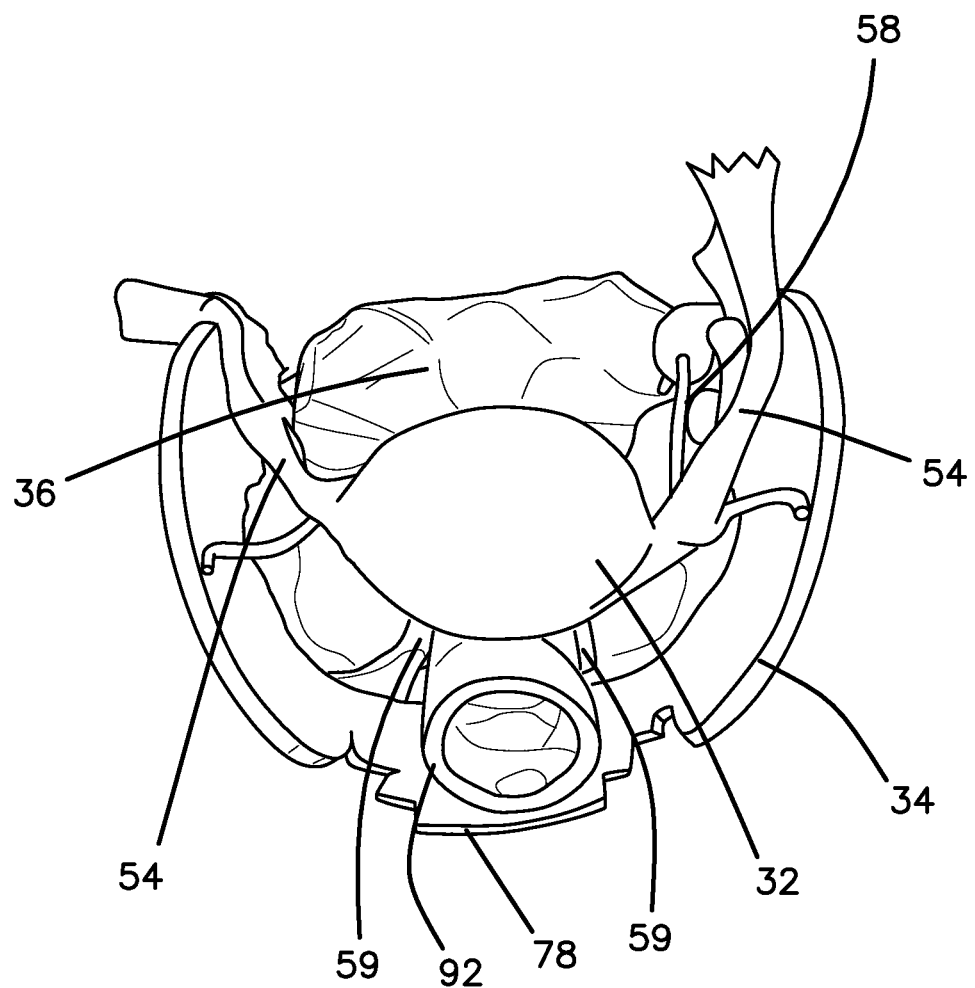
FIG. 4E is a cephalad end view of a model inside a surgical training device according to the present invention.
Figure 5A:
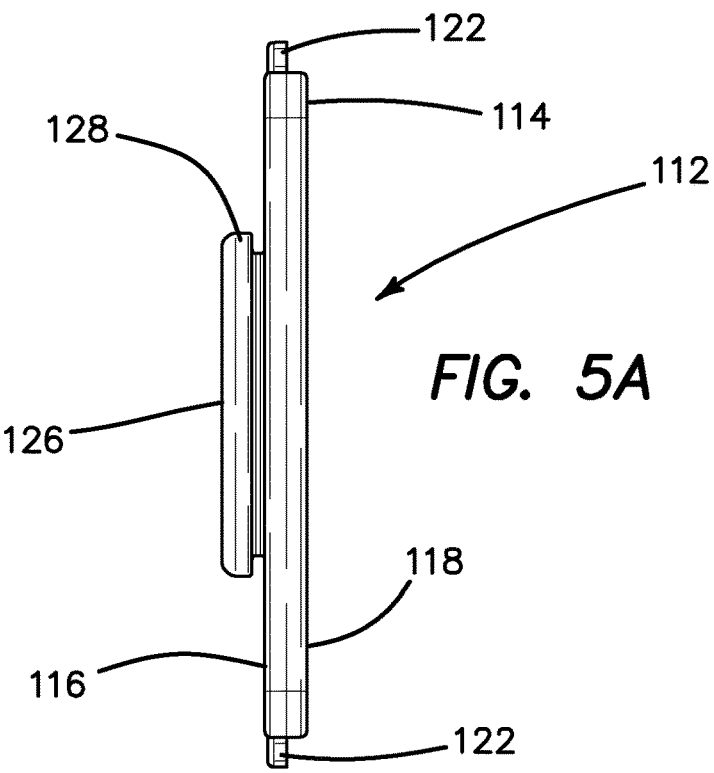
FIG. 5A is a side view of a transvaginal adapter according to the present invention.
Figure 5B:
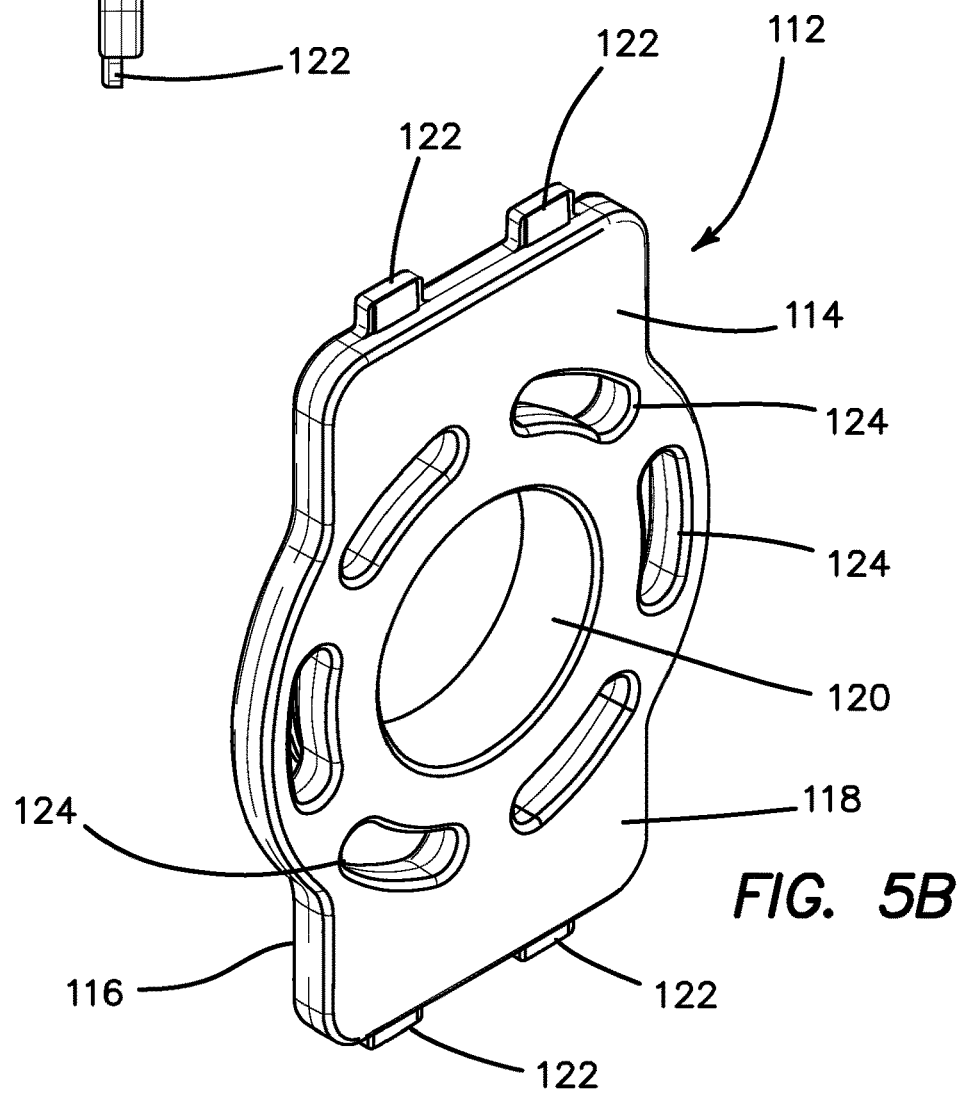
FIG. 5B is a top perspective view of a transvaginal adapter according to the present invention.

The simulated uterus 32 further includes simulated fallopian tubes 54 connected to ovaries 56. The simulated uterus 32, fallopian tubes 54 and ovaries 56 are made of silicone or other elastomeric material and may include other material such as foam material combined with the silicone. The simulated uterus 32 is made of silicone or lighter foam such as urethane or silicone foam or a combination of the two. The silicone construction imparts the simulated uterus 32 with a more realistic weight when the attached simulated cervix 50 is being pulled and manipulated. The simulated uterus 32 made of foam makes the simulated uterus 32 easier to suspend inside the simulated pelvic cavity. Also, when removing the simulated uterus 32 the lightweight foam flexes more easily than a simulated uterus 32 made of higher durometer silicone allowing a larger simulated uterus 32 to be placed into the model 30 and still be removed. The foam uterus 32 would compress and flex as it is being removed through the vaginal opening 48 similar to an actual surgery. The simulated uterus 32 is approximately 300-500 grams and the simulated uterus 32 is composed of a selected durometer foam to accurately represent the size and weight of a real uterus that could normally be removed vaginally without significant morcellation. The use of foam for the artificial uterus provides a realistic resistance during vaginal hysterectomy, proper bulk density and realistic morcellation properties along with an overall muscular-like feel without collapsing during removal. In another variation, the simulated uterus 32 is a combination of silicone and foam to give a more realistic look to the simulated uterus 32 while still having the flexibility of the foam. The foam can be cast and then the silicone can be applied over the foam such as, for example, on a rotational mold in an overmolding method. This variation advantageously results in not having to put mesh reinforcement along the entire length of the artificial uterus and allows the artificial uterus to be manipulated while having a smooth realistic finish that permits the color to be changed by using different colored silicone and/or foam. The simulated uterus 32 is generally pink in color and the fallopian tubes 54 and ovaries are clear or white in color. Furthermore, the simulated uterus 32 may include embedded tumors, cysts and/or ectopic pregnancies in the fallopian tubes 54. The model 30 may further include simulated vasculature 58 such as blood vessels. The simulated vasculature 58 is made of solid or hollow tubular silicone or other suitable elastomer. Liquid may be included inside the hollow tubing of the simulated vasculature 58. The simulated vasculature 58 that simulates blood vessels may be red in color. The model 30 may also include simulated ligaments 59 such as the uteralsacral ligament 59 and made of silicone material as seen in FIGS. 2 and 4E. The model 30 may further include the round and tubo ovarian ligaments 61 attached to the frame 34 shown in FIG. 2.

Figure 3A:
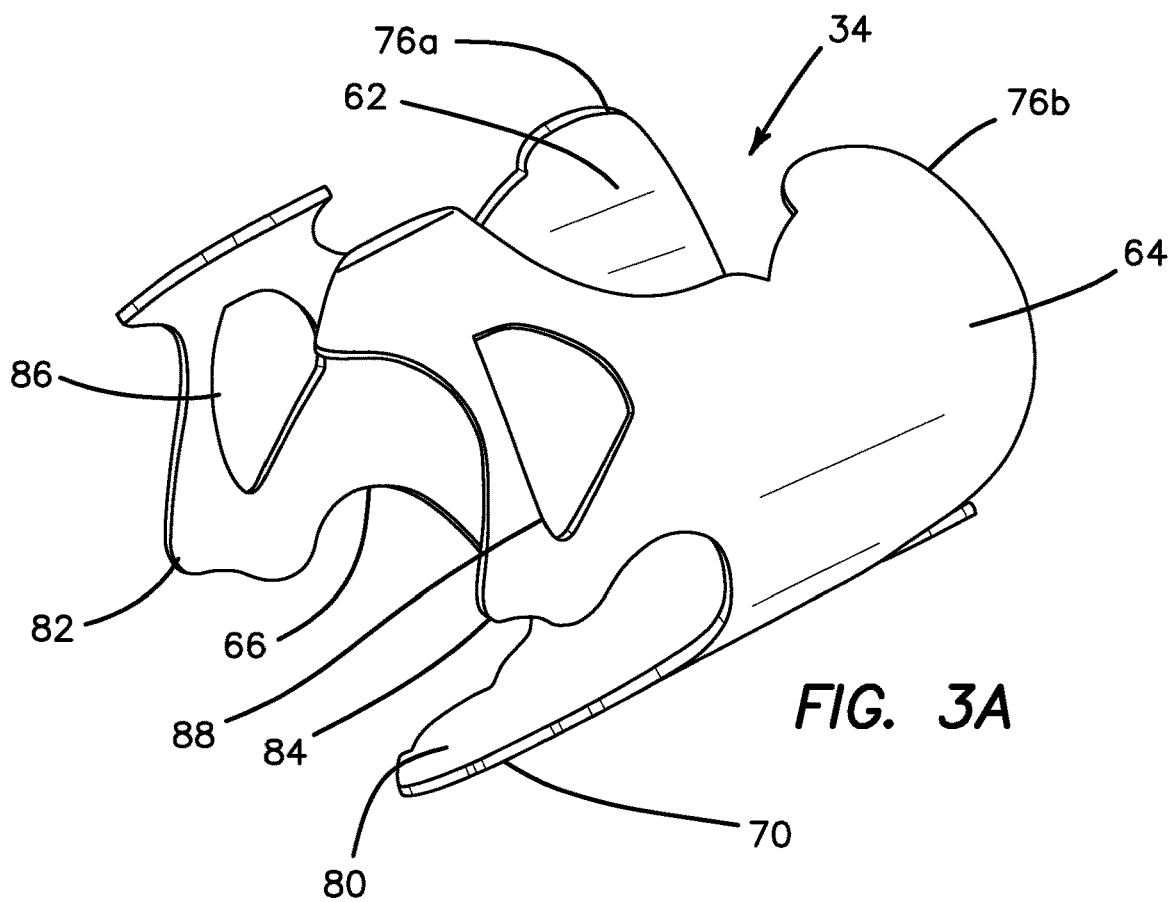
FIG. 3A is a top perspective view of a pelvic frame according to the present invention.
Figure 3B:
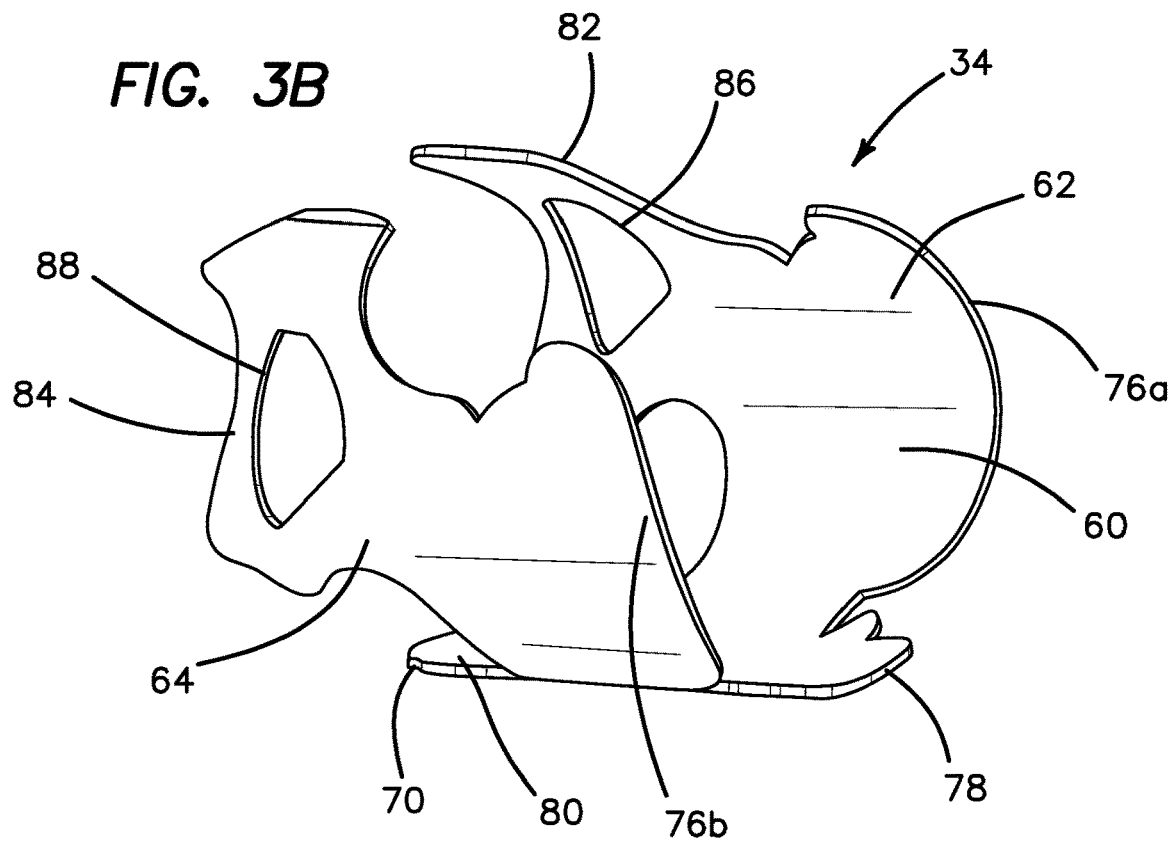
FIG. 3B is a top perspective view of a pelvic frame according to the present invention.
Figure 3C:
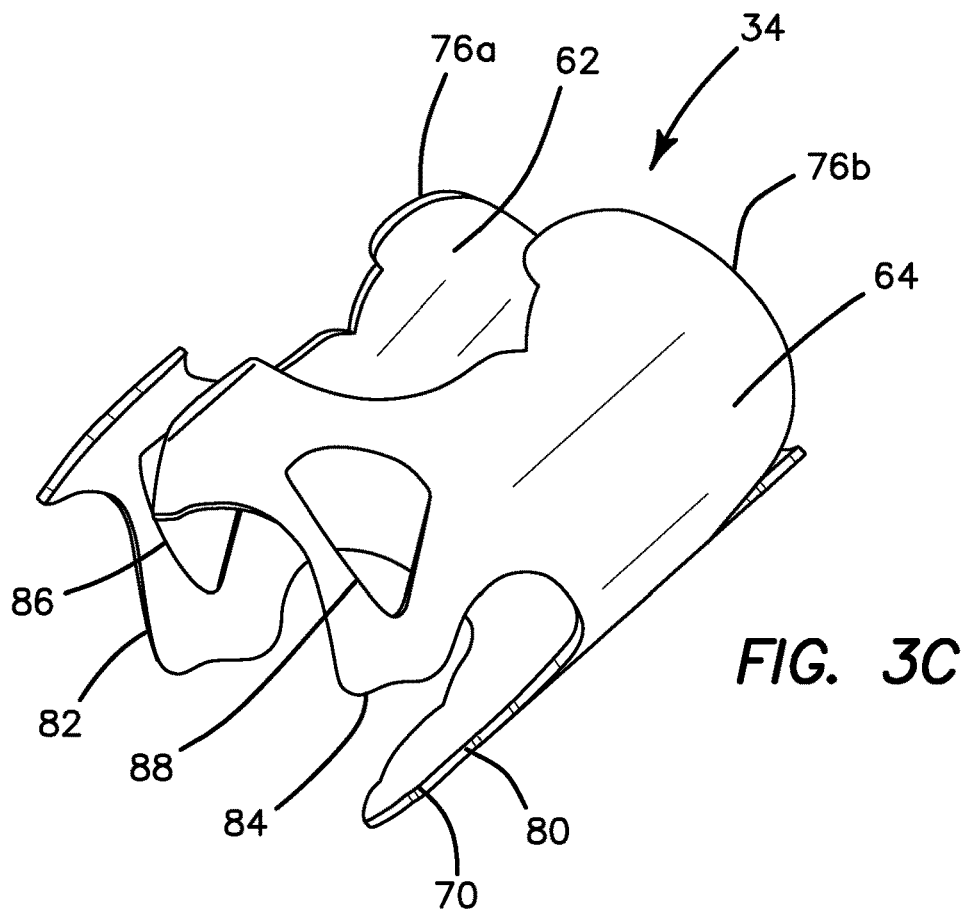
FIG. 3C is a top perspective view of a pelvic frame according to the present invention.
Figure 3D:
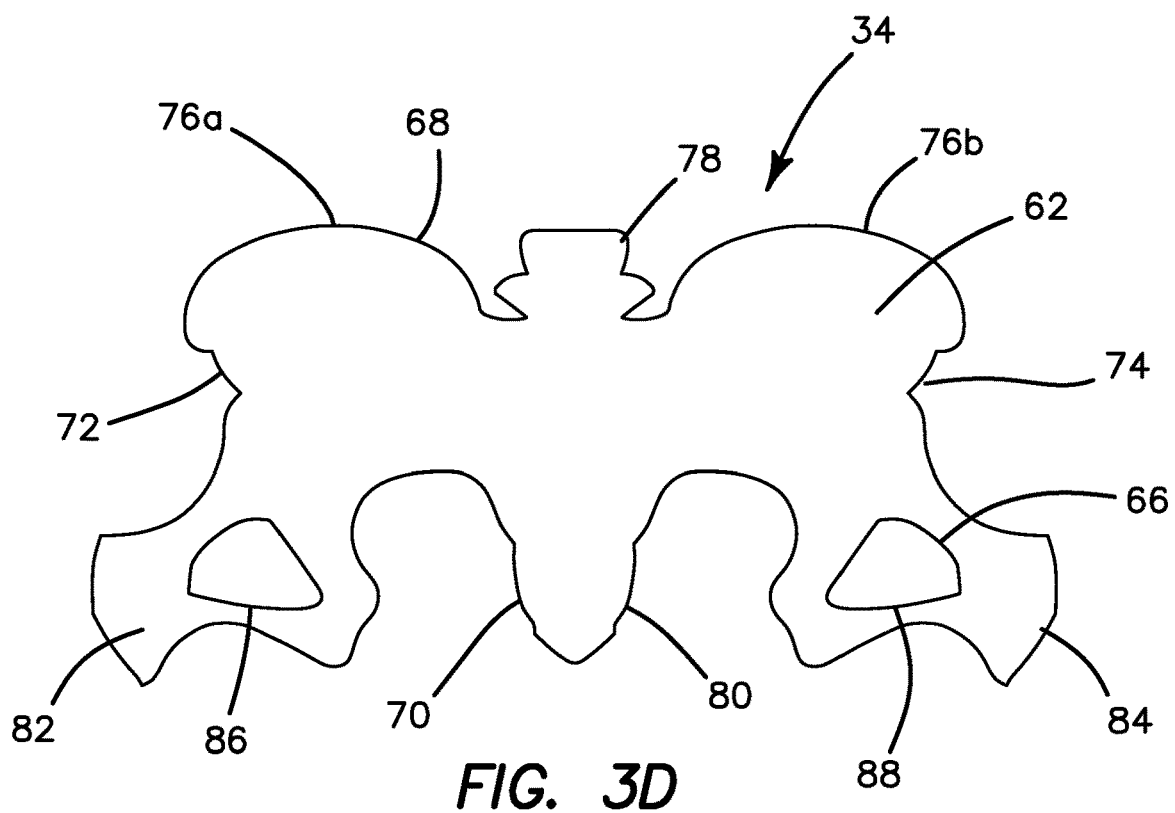
FIG. 3D is a top view of a pelvic frame in a flat orientation according to the present invention.
Figure 7:
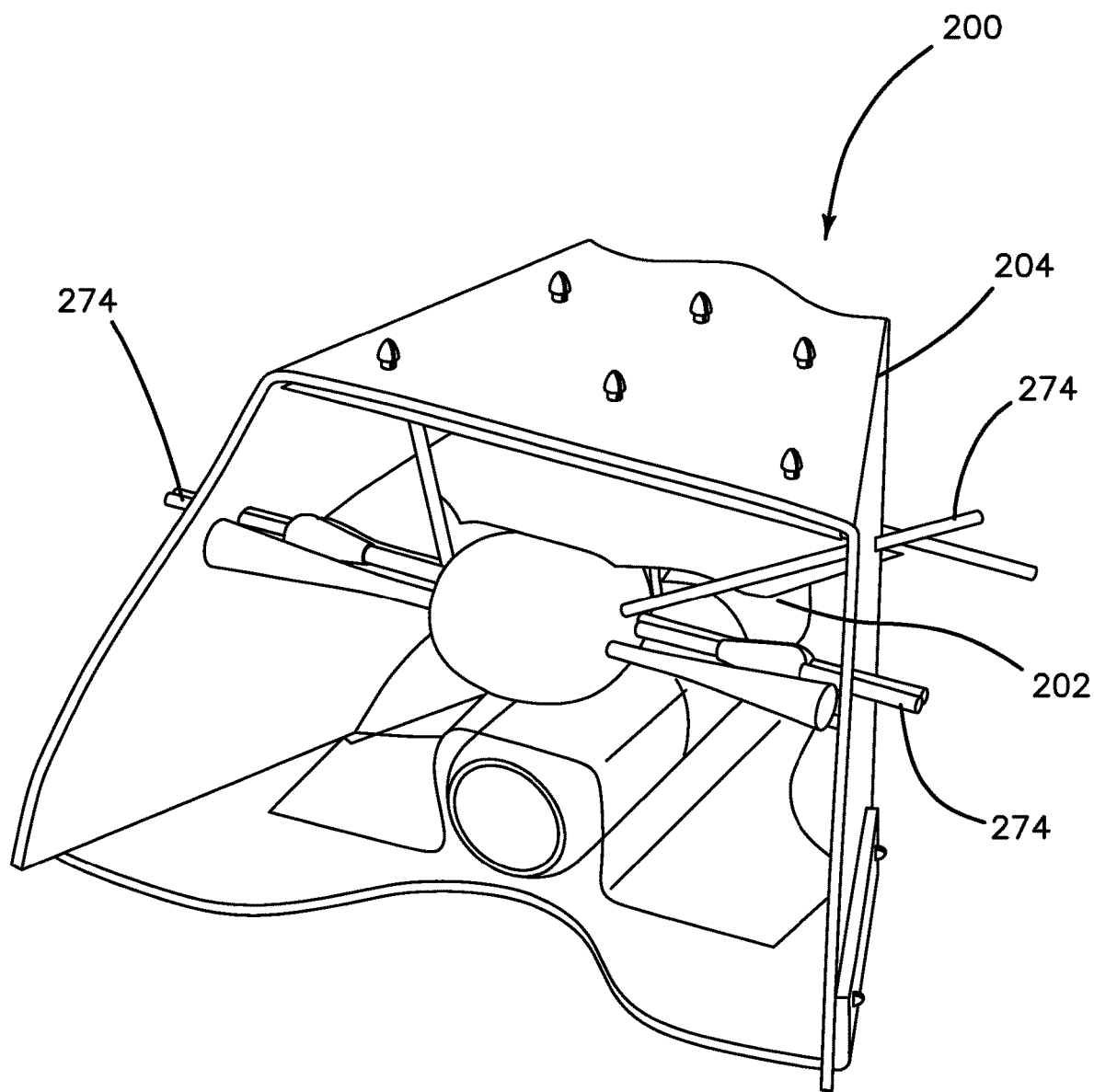
FIG. 7 is a top perspective view of a hysterectomy model according to the present invention.

With additional reference to FIGS. 3A-3D, the frame 34 comprises a cylindrical-like shape defining an interior/lumen 60. The frame 34 includes a first surface 62 interconnected to a second surface 64 defining a thickness therebetween. The first surface 62 defines the inner surface of the cylindrical-like shape of the frame 34 and the second surface 64 defines an outer surface of the cylindrical-like shape of the frame 34. The frame 34 is made of flexible foam material that is also slightly compressible. The frame 34 includes one or more cutouts 66 extending between the first surface 62 and the second surface 64 to define an outer perimeter and apertures. In one variation, the frame 34 is made of a sheet of foam material that is cut according to a pattern shown in FIG. 3D. FIG. 3D illustrates the outer perimeter having a top 68 and a bottom 70 interconnected by a first side and a second side 72, 74. The top 68 includes two curved portions 76a, 76b interconnected at a first protrusion 78 along a vertical axis. The two curved portions 76a, 76b represent the left and right illium/iliac crest. The bottom 70 includes a second protrusion 80 along the vertical axis. The first protrusion 78 represents the sacrum of a human pelvis and the second protrusion 80 represents the coccyx. The first side 72 includes a first lower lobe 82 having a first aperture 86 and the second side 74 includes a second lower lobe 84 having a second aperture 88. The first and second lower lobes 82, 84 represent the left and right ischium and the first aperture 86 and the second aperture 88 represent the obturator foramen of the human pelvis. A piece of foam having a thickness is cut to have the flat pattern shape shown in FIG. 3D. Then the piece of foam is curved such that the first lower lobe 82 and second lower lobe 84 join together in a cylinder-like configuration. Where the two lobes 82, 84 are joined, represent the pubic bone/pubis/pubis symphysis. The two lobes 82, 84 can be joined by adhesive or connected in another suitable manner. In another variation, the two lobes 82, 84 are not joined together but remain spaced apart in a semi-cylindrical-like or split cylinder configuration. The frame 34 is bendable and may be made of a material that retains its shape after bending such as aluminum. Also, the clips 26 and wire that are connected to the trainer 10 may be used to hold the two lobes 82, 84 in an upward orientation and in a cylindrical-like configuration while inside the trainer 10. The anatomy of the pelvis is shown in FIG. 7.

The frame 34 is made of soft, compressible, semi-rigid foam that can be die cut and then formed into the correct shape with adhesive. If the frame 34 is made of harder plastic, it could be a thin thermoform that is initially formed into the correct shape or a thicker plastic that is cut into the pelvis shape and then formed into a cylindrical shape with heat. The frame 34 may also be made of deformable metal that holds its shape. The frame 34 is not a perfect replica of the anatomy and need only include certain features selected to practice certain procedures that require those specific features as anatomical reference points or visual landmarks for the practitioner. For example, for practicing a vaginal hysterectomy, the important features of the pelvis are the restriction of the pelvic inlet and the attachments to the pelvic sidewall. For practicing a transanal total mesorectal excision (taTME), the L-shape of the sacrum is an important landmark. For hernia procedures, the pubic tubercle is an important landmark. The frame 34 can be made to have all anatomically correct features or only the ones needed for the specific procedure. As such, the frame 34 and model 30 can be used for the simulation of a vaginal hysterectomy, abdominal hysterectomy, colectomy, hernia, taTME, and other pelvic procedures. In another variation, the frame 34 forms a conical shape or frusto-conical shape having an open proximal and open distal ends.

With reference back to FIG. 2, the model 30 may further include a simulated bladder 90. The simulated bladder 90 is a hollow, air-filled component typically made of silicone or other elastomeric material. In another variation, the simulated bladder contains liquid. The simulated bladder 90 is connected to the frame 34 with adhesive or other means. It is connected to the first surface 62 or inner surface of the frame 34. The simulated bladder 90 is attached in alignment with the vertical axis in the location of where the two lobes 82, 84 are in juxtaposition in a location representative of the pubis. When connected the simulated bladder 90 extends into the lumen 60 of the frame 34. The simulated bladder 90 may further include a simulated ureter 94. In one variation, the simulated ureter 94 is connected to the simulated bladder 90. The simulated ureter is made of solid or hollow tubular silicone.

Still referencing FIG. 2, the model 30 may further include a simulated colon 92 or bowel portion. The simulated colon 92 is a tubular structure that includes a lumen. The simulated colon 92 is laid on the first surface 62 inside the interior 60 of the frame 34 and substantially along the vertical axis and against the second protrusion 80 of the frame 34. Adhesive may be used to attach the simulated colon 92 to the frame 34. The simulated colon 92 is made of silicone or other suitable elastomeric material and colored pink or other suitable color and may or may not include simulated tumors.

The first sheet 36 is a thin layer of clear silicone material having a top surface 96 and a bottom surface 98 and a first end 100 and a second end 102. The first sheet 36 is transparent and at least one of the top surface 96 and the bottom surface 98 is textured in one variation. The first sheet 36 is attached to the simulated uterus 32. In particular, the bottom surface 98 of the first sheet 36 near the first end 100 is attached along at least a portion of the length of simulated uterus 32 to one or more of the bulbous portion 40 and tubular portion 44 as shown in FIG. 2. The first sheet 36 is then folded back toward the top of the model 30 and toward the first end 100 of the first sheet 36 creating a fold near the tubular portion 44 of the simulated uterus 32. At least a portion of the first sheet 36 near the second end 102 of the first sheet 36 is attached to the frame 34 such that the bottom surface 98 of the first sheet 36 is adhered to the frame 34 in the general location of where the two lobes 82, 84 are in juxtaposition to create a cylinder-like configuration for the frame 34. The attachment of the first sheet 36 may also serve to hold the frame 34 in the cylindrical-like configuration. Adhesive is used to attach the bottom surface 98 of the first sheet 36 to the frame 34. The bottom surface 98 of the first sheet 36 is attached to the first surface 62 or inner surface of the frame 34 and then folded around a portion of the first side 72 and second side 74 of the frame 34. If a simulated bladder 90 is employed in the model 30, then the second end 102 of the first sheet 36 is also attached with adhesive to the outer surface of the simulated bladder 90 capturing the simulated bladder 90 between the frame 34 and the first sheet 36. A portion of the second end 102 of the first sheet 36 is folded around the edge of the frame 34 and attached to the second surface 64 of the frame 34 such that at least part of the second end 102 of the first sheet 36 is resident above the second or outer surface 64 of the frame 34 as visible in FIG. 4D. The first sheet 36 is sized and configured to suspend the simulated uterus 32 inside the interior 60 of the frame 34. Simulated vasculature 58 may be attached to the top surface 96 or bottom surface 98 of the first sheet 36. The configuration of the first sheet 36 forms a pocket-like structure wherein the top surface 96 of the first sheet 36 is folded and at least in part facing itself. The first sheet 36 creates a webbing of suspension that simulates the peritoneum layer.

The second sheet 38 is a thin layer of clear silicone material having a top surface 104 and a bottom surface 106 and a first end 108 and a second end 110. The second sheet 38 is transparent and at least one of the top surface 104 and the bottom surface 106 is textured in one variation. The second sheet 38 is attached to the simulated uterus 32. In particular, the bottom surface 106 of the second sheet 38 near the first end 108 is attached along at least a portion of the length of simulated uterus 32 to one or more of the bulbous portion 40 and tubular portion 44 on a side opposite from where the first sheet 36 is attached. The first sheet 36 is attached to the anterior side of the model 30 which is also the anterior side of the simulated uterus 32. The second sheet 38 is attached to the posterior side of the model 30 which is also the posterior side of the simulated uterus 32. After being attached to the posterior side of the simulated uterus 32, the second sheet 38 is then folded back toward the top of the model 30 and toward the first end 108 of the second sheet 38 creating a fold near the tubular portion 44 of the simulated uterus 32. At least a portion of the second sheet 38 near the second end 110 of the second sheet 38 is attached to the frame 34 such that the bottom surface 106 of the second sheet 38 is adhered to the frame 34 in the general location of the second protrusion 80. Adhesive is used to attach the bottom surface 106 of the second sheet 38 to the frame 34. The bottom surface 106 of the second sheet 38 is attached to the first surface 62 or inner surface of the frame 34 and may be folded around the edge of the frame 34 such that at least part of the second end 110 of the second sheet 38 is connected to second or outer surface 64 of the frame 34. If a simulated colon 92 is employed in the model 30, then the second end 110 of the second sheet 38 is also attached with adhesive to the outer surface of the simulated colon 92 or at least overlaying and not attached with adhesive such that at least a portion of the simulated colon 92 is captured or located between the frame 34 and the second sheet 38. The second sheet 38 is sized and configured to suspend the simulated uterus 32 inside the interior 60 of the frame 34 if the model 30 is turned over. Simulated vasculature 58 may be attached to the top surface 104 or bottom surface 106 of the second sheet 38. The configuration of the second sheet 38 forms a pocket-like structure wherein the top surface 104 of the second sheet 38 is folded and at least in part facing itself. The second sheet 38 creates a suspended webbing that simulates the peritoneum layer.

With reference now to FIGS. 4A-4E, the model 30 is shown placed inside a surgical training device 10 of the like described with respect to FIG. 1. The model 30 is shown inside the body cavity 12 and oriented such that the top 68 of the frame 34 is in the cephalad direction of the simulated training device 10 and the vaginal opening 48 of the simulated uterus 32 faces the caudal direction of the simulated training device 10. The model 30 can be connected to the surgical training device 10 with the clips 26 attached to the trainer 10. The retractable clips 26 can be pulled out and the clips 26 attached to any portion of the model 30 such as to the frame 34 of the model 30. Also, the second or outer surface 64 of the model 30 may include a hook-and-loop type fastener configured to attach to a complementary portion of hook-and-loop type fastener connected to the base 18 of the trainer 10. Together with one or more fasteners such as the clips 26 and/or hook-and-loop type fasteners, the model 30 is securely attached to the trainer 10 such that it can be manipulated in simulated surgery without dislodging the model 30 from the body cavity 12 of the trainer 10. The model 30 is further connected to the trainer 10 via a transvaginal adapter 112 that is sized and configured to connect between the top cover 16 and the base 18 as an additional leg 20 positioned at the caudal direction of the surgical training device 10.

Turning now to FIGS. 5A-5B and 6A-6B, there is shown a transvaginal adapter 112. With reference also back to FIG. 1, there is shown a top cover supported above the base by five legs 20. In one variation, a sixth leg 20 is provided as shown in FIGS. 4A-4D in the form of the transvaginal adapter 112. The trainer 10 may be assembled with an optional sixth support structure or leg which is configured for simulating transvaginal surgery including transvaginal hysterectomies.

The transvaginal adapter 112 includes a flat plate 114 having an inner surface 116 for facing toward the interior of the trainer and an outer surface 118 for facing outwardly towards the user. The plate 114 has a rectangular shape and includes an aperture 120 passing through the plate 108 from the inner surface 116 to the outer surface 118. In one variation, the aperture 120 is circular in shape. In another variation, the aperture 120 is elongate elliptical oval-like in shape and oriented vertically along the longitudinal axis of the adapter 112. In another variation, the aperture 120 is elongate elliptical oval-like in shape and oriented perpendicularly to the longitudinal axis of the adapter. As shown in FIGS. 5A-6B, the plate 114 also includes means such as tabs 122 or a U-shaped channel for inserting to connect the transvaginal adapter 112 to the top cover 16 and to the base 18 to help support and space apart the top cover 16. The transvaginal adapter 112 is located between the top cover 16 and the base 18 and provides a side access aperture 16 lateral to the trainer 10 or substantially perpendicular to the top cover 16 and the base 18. The plate 114 further includes a plurality of molding apertures 124 surrounding or encompassing the main aperture 120 configured for overmolding a soft simulated vaginal tissue interface made of silicone or the like. In another variation the interface is insertable into the aperture 120 of the transvaginal adapter 112. The tissue interface (not shown) includes an aperture that is substantially coaxial with the plate aperture 120. At the inner surface of the transvaginal adapter 112, a tubular extension 126 is integrally provided and extends into the simulated body cavity 12 of the trainer 10. The tubular extension 126 is longer in FIGS. 6A-6B in comparison to the tubular extension 126 of FIGS. 5A-5B. The tubular extension 126 is sized and configured such that the tubular portion 44 of the simulated uterus 32 can be stretched around the extension 126 and secured to the transvaginal adapter 112 such that the vaginal canal 46 is supported in an open configuration, coincident with and accessible through the aperture 120 of the adapter 112 as shown in FIGS. 4A-4D. The tubular extension 126 serves as a connector connecting the model 30 with the trainer 10 in a manner that permits the interior of the uterus to be accessed as in real surgery. In one variation, the tubular extension 126 is a cylindrically-shaped extension having a radially-extending distal flange 128 that extends around at least a portion of the extension 128 to help secure and retain the model 30 attached to the trainer 10. The tubular portion 44 of the model 20 is attached to the tubular extension 126 by pulling the tubular portion 44 over the distal flange 128, if one is provided, and over and around the tubular extension 126 the outer diameter of which is the same or slightly larger than the relaxed inner diameter of the tubular portion 126 to keep the tubular portion 44 secured to the transvaginal adapter 112. The transvaginal adapter 112 can be made of flexible or rigid material. If the adapter 112 is made of rigid material it will tend to simulate an already retracted vaginal canal 46. If the adapter 112 is made of flexible material or soft material, the adapter 112 is suited for practicing retraction. In another variation, the transvaginal adapter 112 has a tubular extension 126 that is made of soft flexible material and plate 114 made of rigid material or surrounded by rigid material to keep the top cover 16 of the trainer 10 supported which would still allow the practitioner to practice retraction at the opening of the vaginal canal 46 at the adapter 112.

In use, the model 30 is placed inside the surgical training device 10 and held in place with a hook-and-loop type fastener and/or retracting clips 26. The tubular portion 44 is attached to the transvaginal adapter 112 by stretching the vaginal opening 48 over the tubular extension 126 of the adapter 112. A curtain may be employed that is placed around the sides of the trainer 30 to further conceal the model 30 such that the only visualization is through the simulated vaginal canal 46. The vaginal canal 46 is then retracted using a surgical retractor. The vaginal canal 46 is made of a flexible thermoplastic elastomer (TPE). The TPE provides resistance as it is retracted and wants to spring back to its original shape which permits the user to practice realistic retraction. The transvaginal adapter 112 of FIGS. 6A-6B having a longer tubular extension 126 is used to simulate an already retracted vaginal canal. Hence, the transvaginal adapter 112 permits the practitioner to practice the hysterectomy procedure without needing extra-hands and assistance to perform the retraction. If the transvaginal adapter 112 of FIGS. 5A-5B having the shorter tubular extension 126 is used, the practitioner will practice retracting the vaginal canal 46 with retractors and the help of extra hands during the procedure. The transvaginal adapter 112 can be made of rigid or flexible material or rigid and flexible material as described above and selected for the purpose of practicing retraction of the vaginal canal 46 or not. Next, the simulated cervix 50 is grasped and pulled towards the opening 48 of the vaginal canal 46. The simulated cervix 50 is made of high durometer silicone relative to the surrounding tubular portion 44. The simulated cervix 50 is also made as a solid component which allows it to be grasped with real surgical tools and pulled on without fear of the silicone ripping or tearing. The simulated cervix 50 is incised circumferentially and the practitioner is able to practice carefully dissecting the vaginal mucosa off of the simulated cervix 50. A sheet of cotton or other webbing-like substance can be included in the model 30 between the vaginal canal 46 and the simulated bladder 90. As described above, the simulated bladder 90 is a hollow, air-filled component. If the practitioner cuts to high while dissecting the simulated vaginal mucosa and the simulated bladder 90 is accidentally incised, the simulated bladder 90 could pop and give immediate feedback to the practitioner especially if the simulated bladder 90 contains fluid.

The model 30 advantageously includes a second sheet 38 forming a fold between the simulated uterus 32 and the frame 34. Also, the suspension of the simulated uterus 32 within the frame 34 advantageously creates a realistic response when the simulated uterus 32 is being incised and manipulated. Also, in the variation in which the simulated uterus is made of lighter foam material, the simulated uterus will remain suspended, hang and swing in response to being manipulated with surgical instruments. At least portions of the simulated uterus and simulated vagina are held in suspension inside the enclosure defined by the pelvic frame and connected thereto or directly connected to the enclosure defined by the trainer. The suspension advantageously permits the fold of the second sheet to be accessed to practice posterior colpotomy into the posterior cul-de-sac incision by incising the peritoneum forming the recto-uterine fold. The suspended simulated uterus 32 allows for the existence of the recto-uterine peritoneum fold. As previously described, the simulated uterus 32 is pendent inside the frame 34 made of foam material that mimics a human pelvis. The simulated uterus 32 is suspended by a folded first sheet of silicone material on the anterior side of the simulated uterus 32 and a folded second sheet of silicone material on the posterior side of the simulated uterus 32. The frame 34 can be made of any material such as plastic or harder foam material. The frame 34 serves as an attachment area for the various simulated portions of the anatomy including the broad ligament, ovaries 56 and fallopian tubes 54. The elasticity of the silicone of these anatomical components allows the simulated uterus 32 to be pulled and manipulated and still remain attached to the frame 34. A frame 34 made of semi-rigid foam may also move as the simulated uterus is being manipulated. A more rigid frame 34 would move less. The practitioner then divides the uteralsacral ligaments 59. The practitioner then performs an anterior colpotomy into the anterior cul-de-sac by incising the first sheet 38 simulating the peritoneum forming the vesico-uterine fold. The practitioner divides the tubo ovarian and round ligaments 61 on each side of the simulated uterus 32. Due to the foam frame 34, the round and tubo ovarian ligaments 59 remain realistically attached to the frame 34 after they have been divided from the simulated uterus 32. The simulated uterus 32 is then freed and removed. The practitioner then practices to suture the vaginal cuff closed by passing a needle and suture through the tubular portion 44 of the model 32 to close the vaginal canal 46 opening. Suturing the vaginal cuff in real surgery is another difficult part of the vaginal hysterectomy due to the space limitations. The tubular portion 44 that is made of TPE holds the suture without tearing and limits the space allowed for instruments during the suturing process. The model 30 allows the practitioner to practice numerous difficult procedures on one model.

Figure 8:
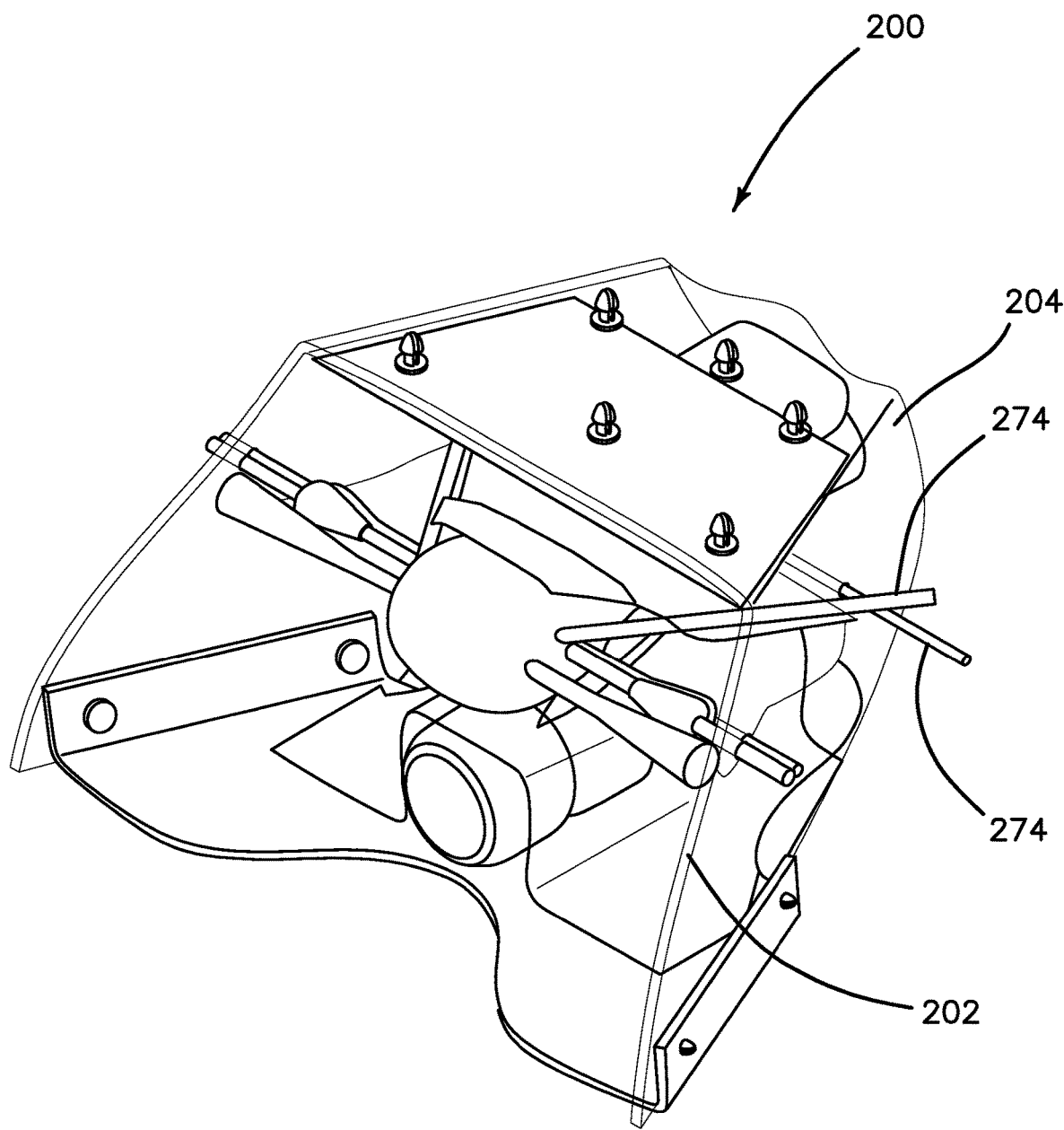
FIG. 8 is a top perspective, partially transparent view of a hysterectomy model according to the present invention.

Turning now to FIGS. 7-8, a hysterectomy model 200 will now be described. The model 200 includes a plurality of simulated organ structures 202 connected to and located inside a frame 204.

Figure 9:
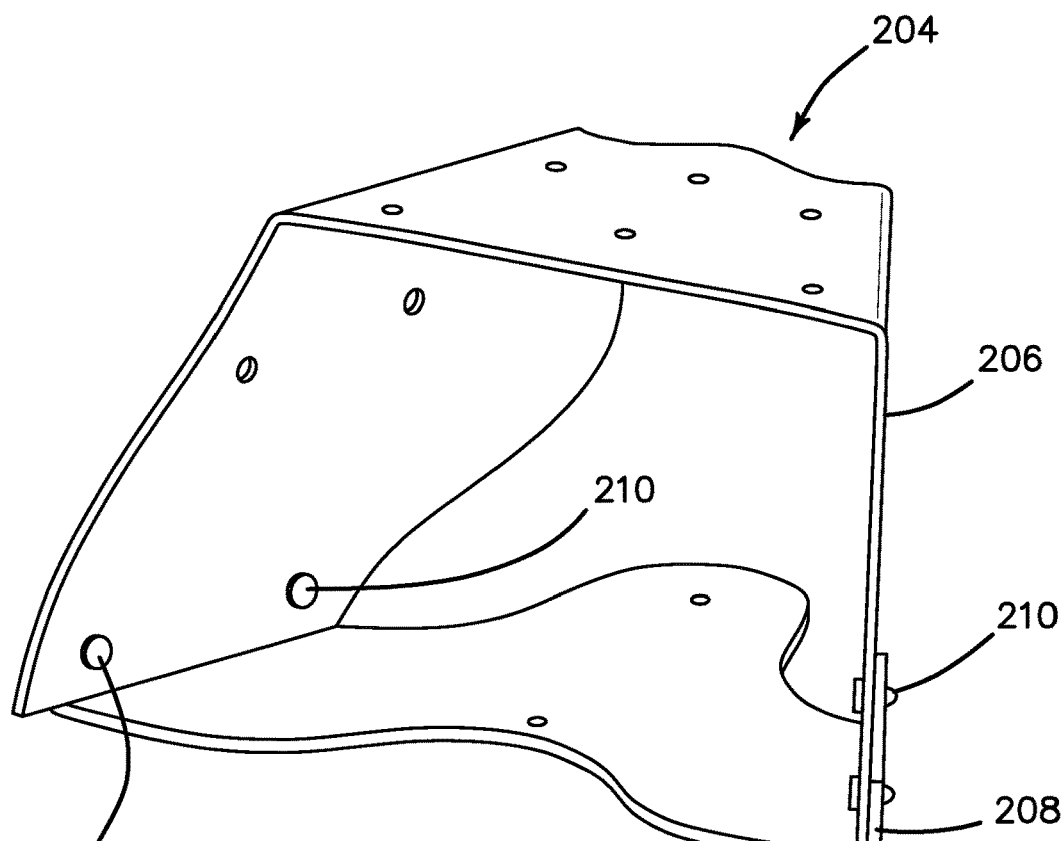
FIG. 9 is a top perspective view of a frame of a hysterectomy model according to the present invention.

Turning now to FIG. 9, there is shown a frame 204 according to the present invention. The frame 204 is configured to simulate a pelvis and serve as a box-like encasement for housing the plurality of simulated organ structures 202. The frame 204 includes a top frame portion 206 connected with fasteners 210 to a bottom frame portion 208. The assembled frame 204 forms a base and a top interconnected by two upstanding sidewalls and defines a central lumen with an open proximal end and an open distal end. The frame 204 has a flat base permitting it to be placed and stand on a flat surface.

Figure 10:
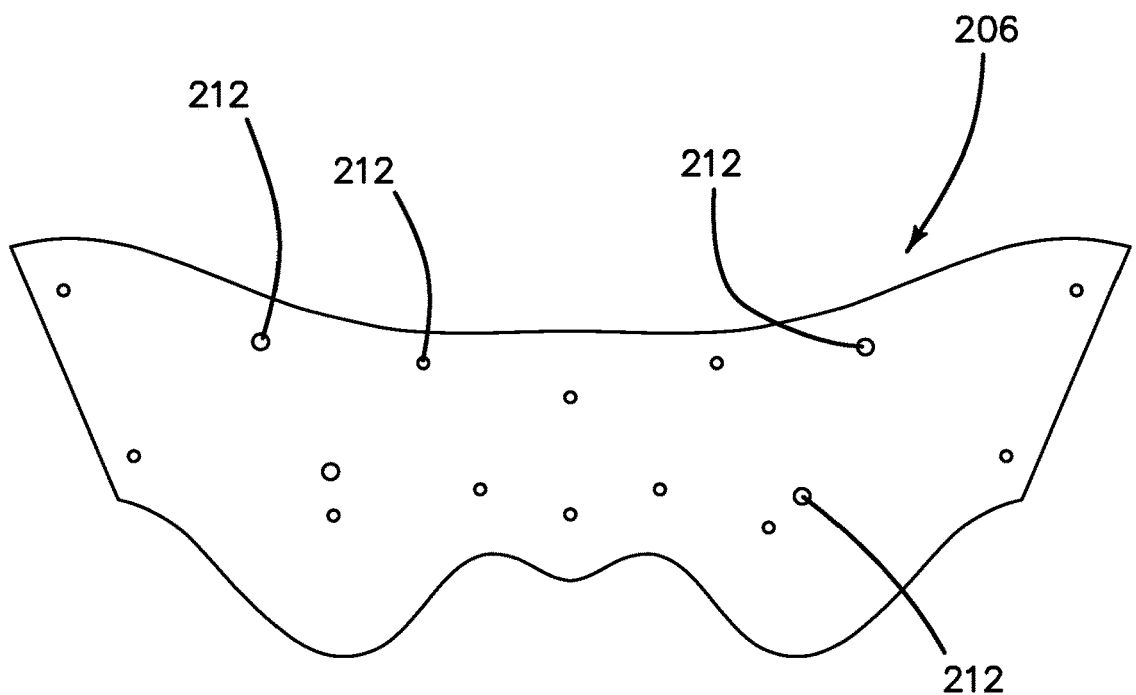
FIG. 10 is a top planar view of a top frame portion of a hysterectomy model according to the present invention.
Figure 11:
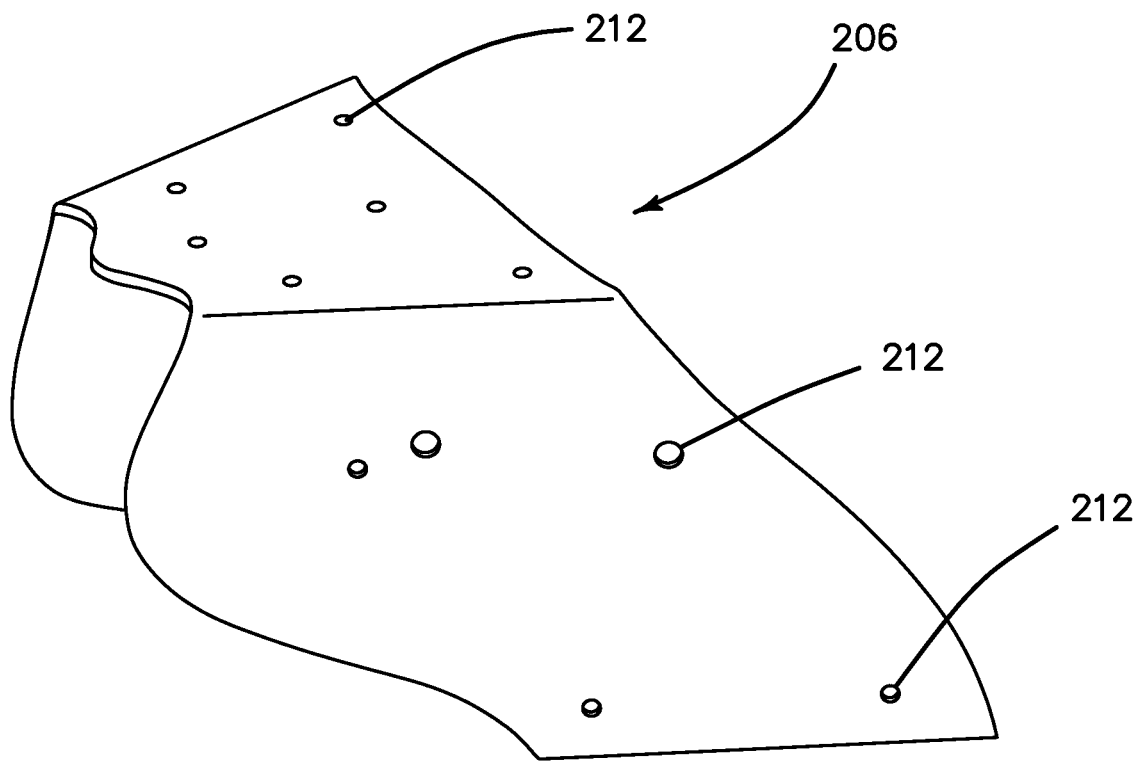
FIG. 11 is a top perspective view of a top frame portion in a folded configuration according to the present invention.

Turning now to FIGS. 10-11, there is shown the top frame portion 206. FIG. 10 illustrates the top frame portion 206 in a flat arrangement. The bottom side includes curvatures representative of the bony structure of the human pelvis and form the sidewalls and top of the frame 204. From the flat arrangement, the top frame portion 206 is folded to form the folded arrangement shown in FIG. 11. The top frame portion 206 includes a plurality of apertures 212 configured to receive fasteners for connecting the plurality of simulated organ structures 202 to the frame 204. Other apertures 212 are configured to pass the simulated organ structures through the apertures 212 and into the frame 204 for supporting the various simulated organ structures such as simulated vasculature with respect to the frame 204 as will be described in greater detail below.

Figure 12:
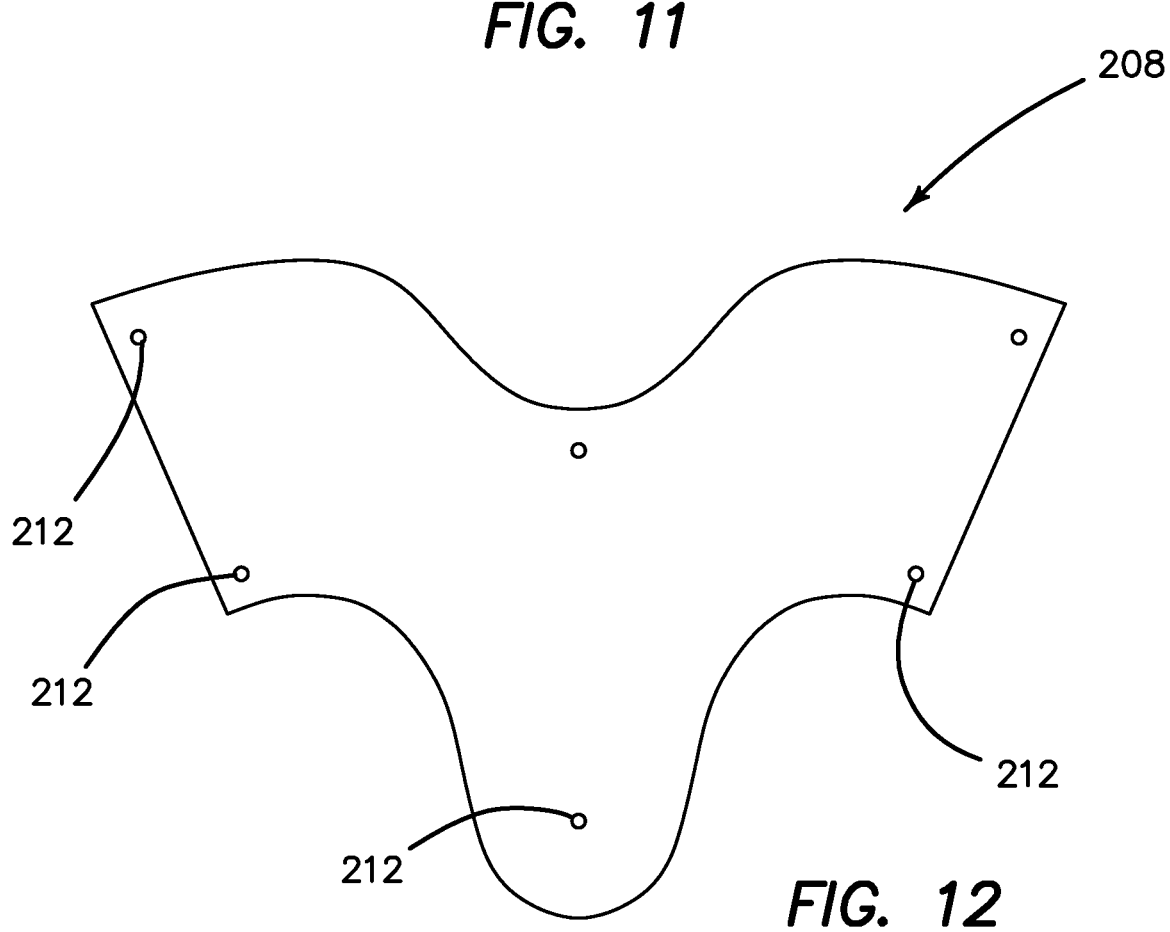
FIG. 12 is a top planar view of a bottom frame portion of a hysterectomy model according to the present invention.
Figure 13:
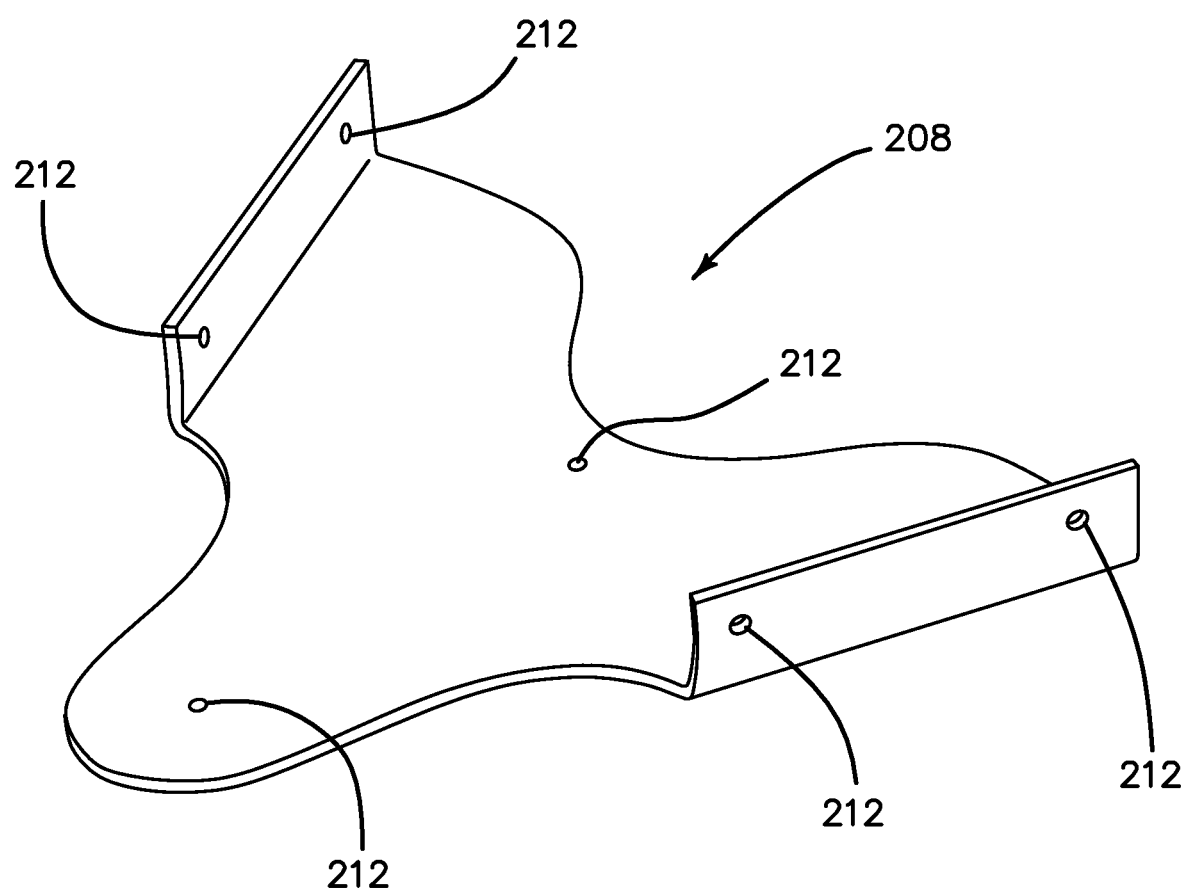
FIG. 13 is a top perspective view of a bottom frame portion in a folded configuration according to the present invention.

Turning now to FIGS. 12-13, there is shown a bottom frame portion 208. FIG. 12 illustrates the bottom frame portion 208 in a flat arrangement and FIG. 13 illustrates it in a folded arrangement. The bottom frame portion 208 defines the base of the frame 204 and includes curved ends that simulate the bony anatomy of the human pelvis. The bottom frame portion 208 also includes a plurality of apertures 212 configured to connect the plurality of simulated organ structures 202 to the frame 204 with fasteners passed through the apertures and/or by passing the simulated organ structures directly through the apertures 212 as will be described in greater detail below.

Figure 14:
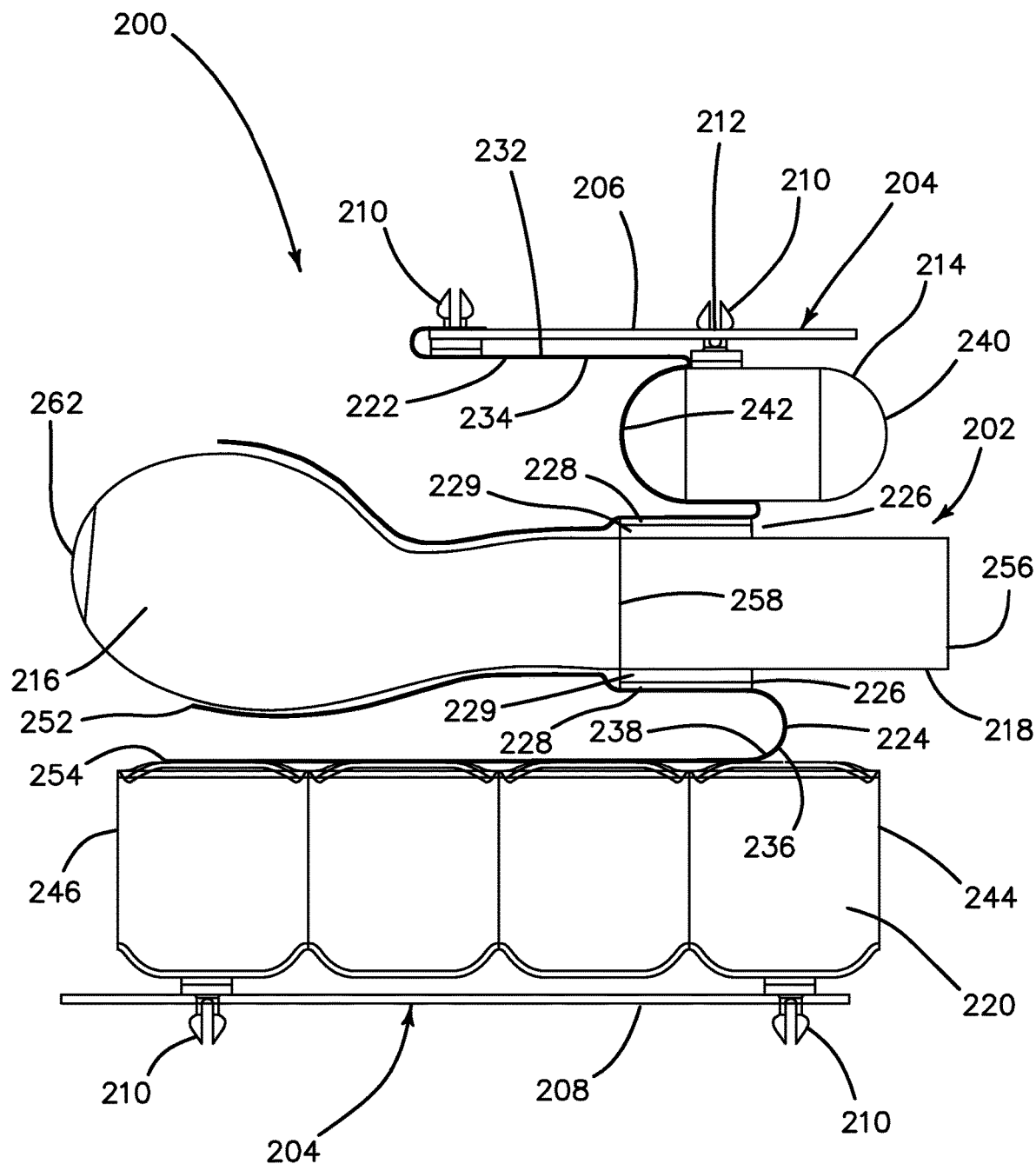
FIG. 14 is a side elevational, partial cross-sectional view of a hysterectomy model according to the present invention.
Figure 15:
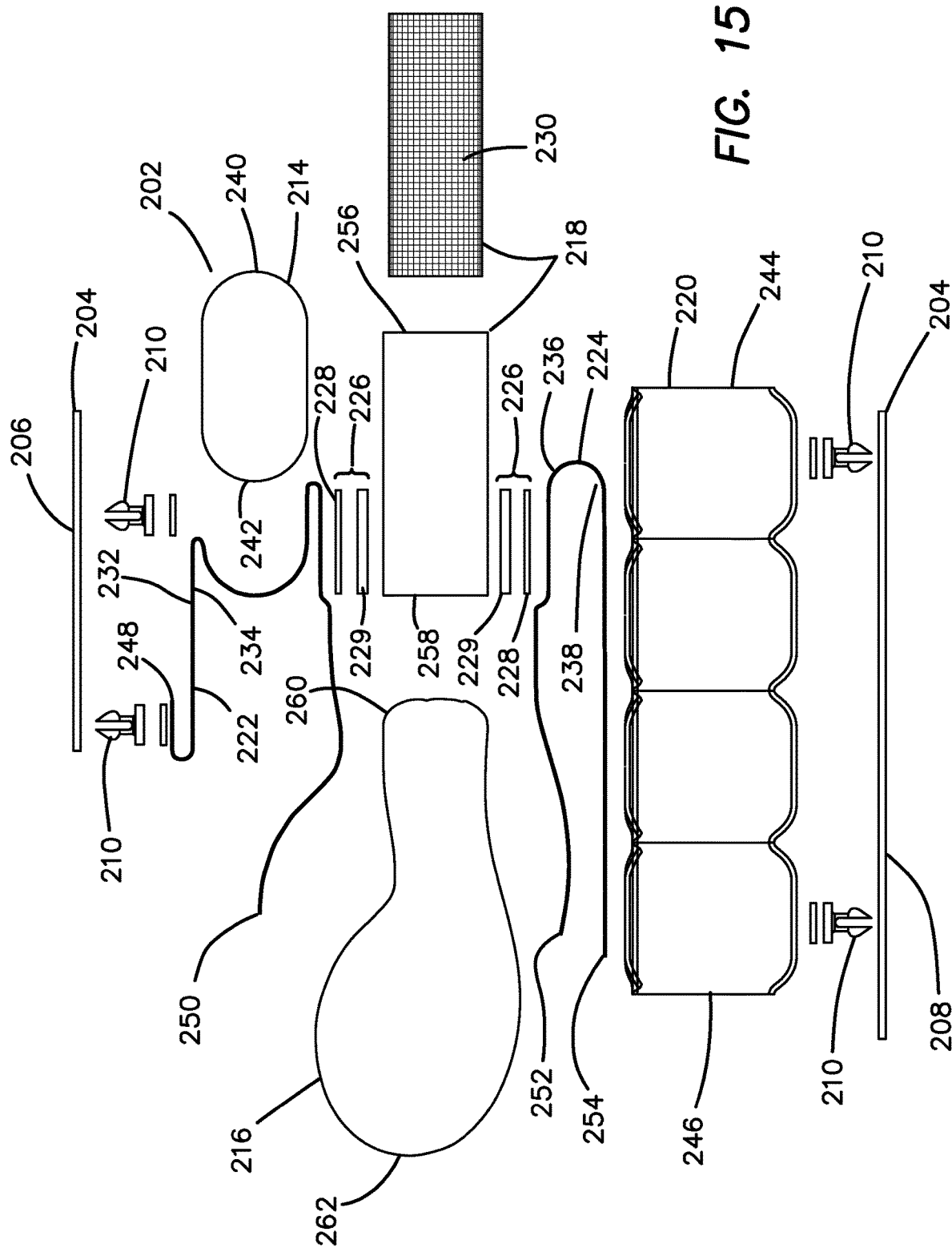
FIG. 15 is a side elevational, exploded view of a hysterectomy model according to the present invention.

Turning now to FIGS. 14-15, the plurality of simulated organ structures 202 and its connection to the frame 204 will now be described. The plurality of simulated organ structures 202 includes a simulated bladder 214, a simulated uterus 216, a simulated vaginal canal 218, a simulated rectum 220, a first sheet 222, a second sheet 224, a dissecting layer 226 and a plurality of fasteners 210. The plurality of organ structures 202 are interconnected as shown in FIG. 14 and in turn connected to the frame 204. Tubular shaped vasculature, ducts, arteries and the like in addition to other simulated organs structures not mentioned herein may be included in this model in an anatomically correct or anatomically similar arrangement for the same or different anatomical location of the body. Each simulated organ structure will now be described.

The simulated bladder 214 forms a closed receptacle with an outer membrane made of pink-colored silicone. The interior of the simulated bladder 214 may be stuffed with polyfil or other material to maintain its shape. The simulated bladder 214 has a proximal end 240 and a distal end 242. The simulated uterus 216 is also made of silicone. The simulated uterus 216 has a proximal end 260 and a distal end 262. The simulated vaginal canal 218 is a tubular structure made of silicone and may optionally contain an embedded mesh layer 230. The simulated vaginal canal 218 has a proximal end 256 and a distal end 258. The simulated rectum 220 is a tubular structure made of silicone with molded transverse folds. The simulated rectum 220 has a proximal end 244 and a distal end 246. Each of the first sheet 222 and the second sheet 224 comprises a large flat planar layer of silicone material. Both sheets 222, 224 represent the peritoneum. The first sheet 222 has a first surface 232 and a second surface 234 and a proximal end 248 and a distal end 250. The second sheet 224 has a first surface 236 and a second surface 238 and a proximal end 252 and a distal end 254.

With continued reference to FIGS. 14-15, the assembly, configuration and connection of the plurality of simulated organ structures 202 will now be described. The distal end of the bladder 242 is attached to the first surface 232 of the first sheet 222 with adhesive approximately midway between the proximal end 248 and the distal end 250 of the first sheet 222 such that the first sheet 222 wraps around the distal end 242 of the simulated bladder 214 from the top of the simulated bladder to the bottom of the simulated bladder 214. The first surface 232 is attached to a fastener 210 near the distal end 248 of the first sheet 222. The first sheet 222 is folded in an approximate U-shape such that the distal end 250 of the first sheet 222 and, in particular, the first surface 232 of the first sheet 222, is attached to the simulated uterus 216 and attached to the simulated vaginal canal 218 via the dissecting layer 226 using adhesive.

The dissecting layer 226 is a construct comprising a silicone layer 228 interconnected with a fiber layer 229. While the silicone layer 228 is uncured, a fiber layer 229 is embedded to form the dissecting layer 226. The dissecting layer 226 is attached to the simulated vaginal canal 218 in pieces or strips while the silicone of the simulated vaginal canal 218 is still wet and uncured on a mandrel. When the dissecting layer 226 is applied to the uncured simulated vaginal canal 218, the uncured silicone of the uncured simulated vaginal canal 218 is allowed to cure to attach the dissecting layer 226, in particular, to attach the fiber layer 229 of the dissecting layer 226 to the simulated vaginal canal 218 sandwiching the fiber layer 229 between two layers of silicone. The dissecting layer 226 may be sectional around the simulated vaginal canal 218 or completely tubular in shape to surround the circumference of the simulated vaginal canal 218. Although the dissecting layer 226 is shown with the same reference number, two dissecting layers 226 may be provided on either side of the simulated vaginal canal 218 as shown in the figures. Also, as shown in FIGS. 14-15, the dissecting layer 226 is attached to distal end 258 of the simulated vaginal canal 218. The dissecting layer 226 is described in detail in co-pending International Patent Application Serial No. PCT/US2016/041852 entitled "Simulated dissectible tissue" filed on Jul. 12, 2016 incorporated herein by reference in its entirety.

The second sheet 224 is attached between the simulated uterus 216 and the simulated rectum 220. In particular, the first surface 236 at the distal end 252 of the second sheet 224 is attached near the distal end 262 of the simulated uterus 216. The second sheet 224 is attached along the length of the simulated uterus 216 toward the proximal end 260 using adhesive. The second sheet 224 is attached to the dissecting layer 226. In particular, the first surface 236 of the second sheet 224 is attached to the silicone layer 228 of the dissecting layer 226 using adhesive. Then, the second sheet 224 is folded to extend back towards the distal end of the simulated rectum 220 and attached along the top side and outer surface of the simulated rectum 220 such that the distal end 254 of the second sheet 224 is near the distal end 246 of the simulated rectum 220. The top side of the simulated bladder 214 is connected to a fastener 210 and this fastener 210 is passed through an aperture 212 in the top frame 206 of the frame 204. The proximal end 248 of the first sheet 222 is also attached to a fastener 210 which is also passed through an aperture 212 in the top frame 206 of the frame 204 to attach the plurality of the simulated organ structures 202 to the frame 204 in a suspended manner. While suspended from the frame 204, the interconnected plurality of simulated organ structures 202 advantageously pendulate and move together in a realistic fashion wherein the point of contact with instruments and the like will move most and simulated organs distal to the point of contact with instruments move to a lesser degree. The bottom side of the simulated rectum 220 is attached to at least two fasteners 210 as shown in FIGS. 14-15. The two fasteners 210 are passed through apertures 212 in the bottom frame 208 to secure the plurality of simulated organ structures 202 to the frame 202. Hence, the plurality of simulated organs structures is spanned across the central opening of the frame 202 with the first sheet 222 and second sheet 224 forming an interconnecting webbing. The proximal end 260 of the simulated uterus 216 is inserted into the distal end 258 of the simulated vaginal canal 218 and joined together with adhesive. A simulated cervix is provided made of silicone and located inside the simulated uterus 216 at the proximal end 260.

Figure 16:
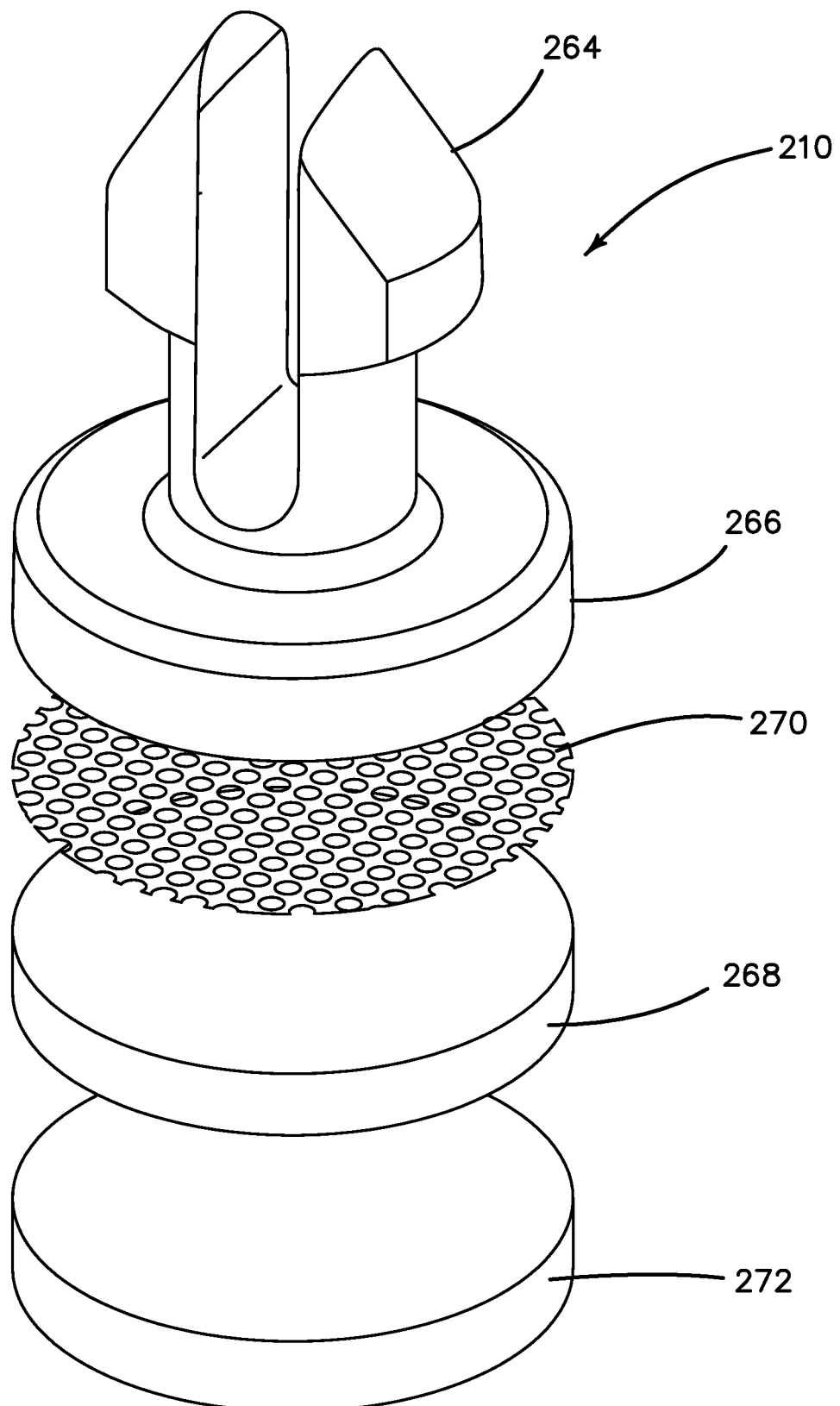
FIG. 16 is an exploded view of a fastener according to the present invention.

Turning now to FIG. 16, the fastener 210 will now be described in greater detail. The fastener 210 has a dual-pronged, hooked, deflectable end 264 connected to a planar surface end 266. The two prongs of the rivet-like fastener 210 extend from the planar surface 266. The two prongs are resiliently deflectable toward and away from each other such that when passed through a smaller aperture, the prongs flex inwardly when ramped against the aperture and then spring back outwardly when the widest portion of the prongs has passed through the aperture, thereby, snapping and hooking into the aperture wall. The fastener 210 is not limited to having a two-prong arrangement. Instead, a single prong may be employed having a bulbous portion for example that is configured to snap through an aperture. A looped layer 268 of looped-sided VELCRO hook-and-loop type fastener is attached to the planar end 266 with cyanoacrylate glue 270. After the layer of looped-side VELCRO hook-and-loop type fastener is attached, a silicone layer 272 is applied while uncured to the looped layer 268 making sure that the wet silicone is spread into the loops of the looped layer 268. Then, the silicone layer 272 is allowed to dry. Instead of a silicone layer 272, a layer of silicone adhesive may be used. The fastener 210 is easily attached to a silicone organ structure with adhesive or by putting a layer of wet silicone onto the organ structure at a location where the fastener 210 is desired to be located. The fastener 210 is then placed on the patch of wet uncured silicone and the patch is allowed to dry, adhering the silicone embedded in the looped layer 268 to the silicone organ structure. In another variation, the silicone layer 272 is part of the silicone organ structure as a patch of wet silicone or part of a cured silicone component of the organ structure and attached with silicone glue. The fasteners 210 are removable with respect to the frame 204 by pressing the prongs together and/or pushing the fastener 210 out of the apertures 212 making the plurality of simulated organ structures 202 removable and replaceable with a new plurality of simulated organ structures 202 for continued practice and training of surgical procedures. The apertures 212 and fasteners 210 may be color-coded to make attachment of the plurality of simulated organ structures 202 to the frame 204 quick and easy.

Upon attachment, simulated vasculature 274, ducts, fallopian tubes, ureters or other anatomical or non-anatomical structure having a tubular/cylindrical form and typically made of silicone are pulled through appropriately-sized apertures 212 as shown in FIGS. 7-8 to further support the connected simulated tissue structures. These tubular structures have a free end and another end that is attached to other simulated tissue structures. The free end is passed through an aperture in the frame and can be secured with adjustable length to adjust the tension on the simulated tissue structures to which it is connected. For example, a loose tension may be created by securing the tubular structure with more slack between the frame and other simulated tissue structure. Alternatively, tension on the simulated tissue may be increased by pulling the tubular structure taunt with respect to the frame to create a relatively less pendulating simulated tissue construct within the frame. The tubular rope-like structure can be tied into a knot along its length to adjust the tension. The knot diameter is made larger than the aperture in frame in order to secure the larger tissue structure to the frame. The knots may be untied to remove the simulated tissue structure or re-tied to provide a different tension level. In another variation, the tubular silicone simulated vasculature 274, ducts, fallopian tubes, ureters or other anatomical or non-anatomical structure having a tubular/cylindrical form are provided with rivets at their distal end. The rivets include a distal end for connection with the frame and a proximal portion embedded or swaged into the ends of the silicone tubular structure to make a mechanical connection. The rivet-like fastener 210 serves as an interface connection between the soft, pliable silicone of the simulated tissue structures and the rigid plastic frame. The simulated tissue structures are often made from room temperature vulcanized (RTV) silicone elastomers. As a result, the simulated tissue structures are delicate and may tear easily if not reinforced. This makes it difficult to connect such artificial tissue structures to the frame. The fastener has a rigid portion for connecting with the rigid frame and an interfacing layer located between the rigid portion of the fastener and the attaching simulated tissue structure. In one variation, the interfacing layer is a fiber layer that wet, uncured silicone may interpenetrate and when cured adhered securely thereto along the area of the interfacing layer. The uncured silicone layer may be a patch on the artificial tissue structure such that when cured, the patch becomes integrally connected to the artificial tissue structure and to the interfacing layer. This type of fastener advantageously minimizes stress concentrations that would result in the fastener tearing away from the simulated tissue structure permitting the simulated tissue structures to be manipulated aggressively. The fasteners also permit a quick assembly of the simulated tissue structure inside the frame by simply snapping the fasteners through a plurality of apertures in the frame. Disassembly is also facilitated and the frame is reusable after a simulated tissue structure is consumed with practiced and replaced with another simulated tissue model that is the same or different from the discarded model. Advantageously, no additional tools or adhesive is required for assembly. As an alternative to the fastener shown in FIG. 16, the first, second and/or third sheets 222, 224 and 225 may be attached to the frame directly with adhesive. Although rivets are described any suitable fastener adapted to secure the simulated tissue structure to the frame is within the scope of the present invention.

Figure 17:
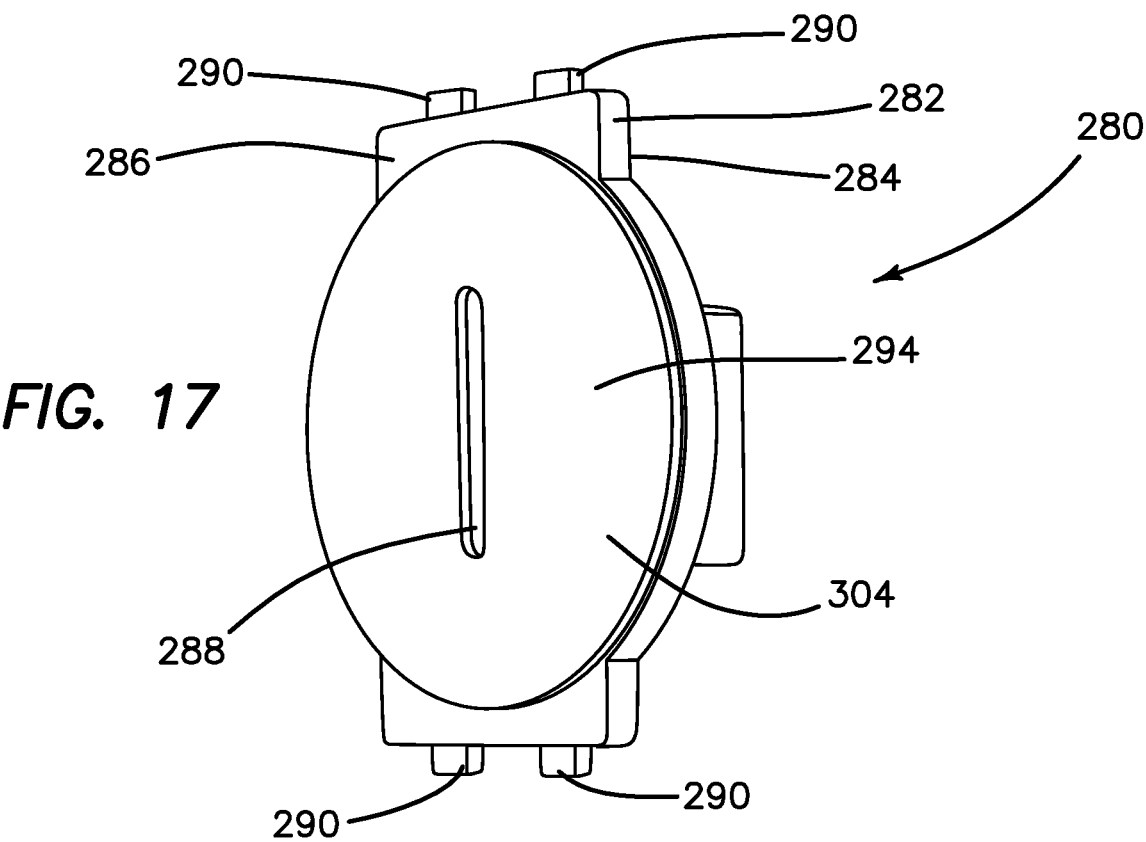
FIG. 17 is a front perspective view of a transvaginal adapter with an overmolded soft simulated vaginal tissue interface according to the present invention.
Figure 18:
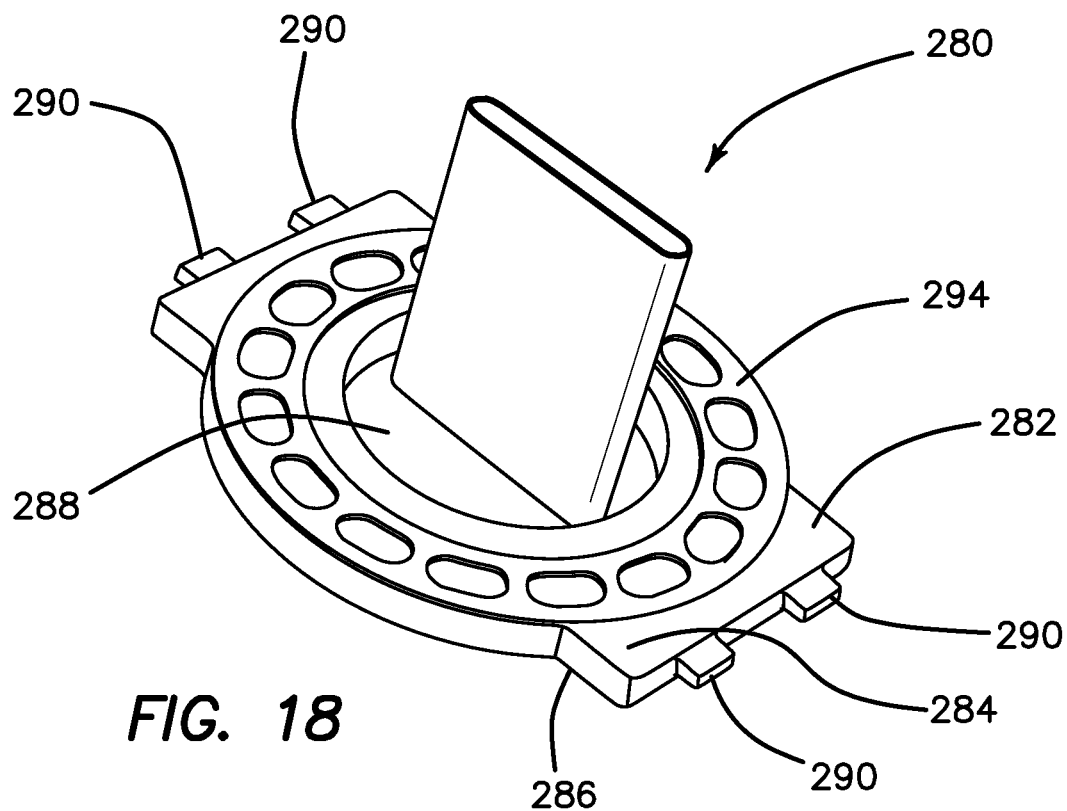
FIG. 18 is a back perspective view of a transvaginal adapter with an overmolded soft simulated vaginal tissue interface according to the present invention.

Turning now to FIGS. 17-18, a transvaginal adapter 280 will now be described. As described above, the transvaginal adapter 280 is formed as a leg 20 configured to support the top cover of the trainer 10. It is configured for simulating transvaginal surgery including transvaginal hysterectomies. The transvaginal adapter 280 includes a flat plate 282 having an inner surface 284 for facing toward the interior of the trainer and an outer surface 286 for facing outwardly towards the user. The plate 280 has a rectangular shape and includes an aperture 288 passing through the plate 280 from the inner surface 284 to the outer surface 286. In one variation, the aperture 288 is circular in shape. In another variation, the aperture 288 is elongate elliptical, oval-like in shape and oriented vertically along the longitudinal axis of the adapter 280. In another variation, the aperture 288 is elongate elliptical, oval-like in shape and oriented perpendicularly to the longitudinal axis of the adapter. The plate 280 also includes means such as tabs 290 or a U-shaped channel for inserting to connect the transvaginal adapter 280 to the top cover 16 and to the base 18 to help support and space apart the top cover 16. The transvaginal adapter 280 is located between the top cover 16 and the base 18 and provides a side access aperture 288 lateral to the trainer 10 or substantially perpendicular to the top cover 16 and the base 18. The plate 280 further includes a plurality of molding apertures 292, shown in FIGS. 23-28, surrounding or encompassing the main aperture 288 configured for overmolding a soft simulated vaginal tissue interface 294 made of silicone or the like. The method of forming the overmolded soft simulated vaginal tissue interface 294 will now be described.

Figure 19:
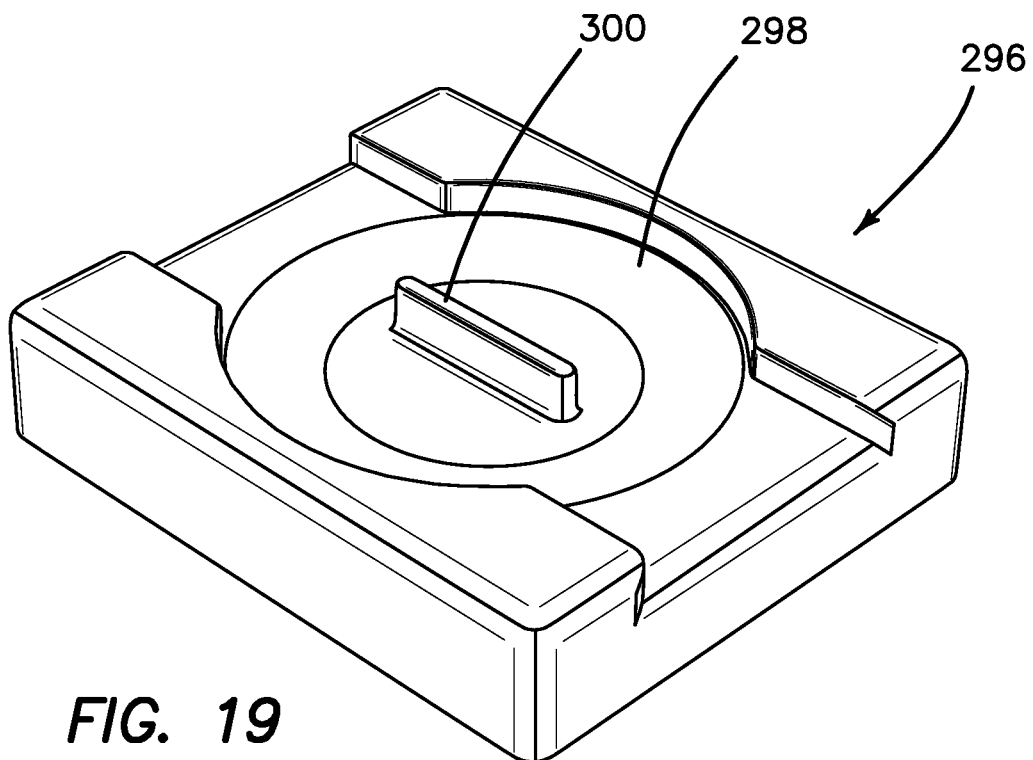
FIG. 19 is a top perspective view of a mold according to the present invention.
Figure 20:
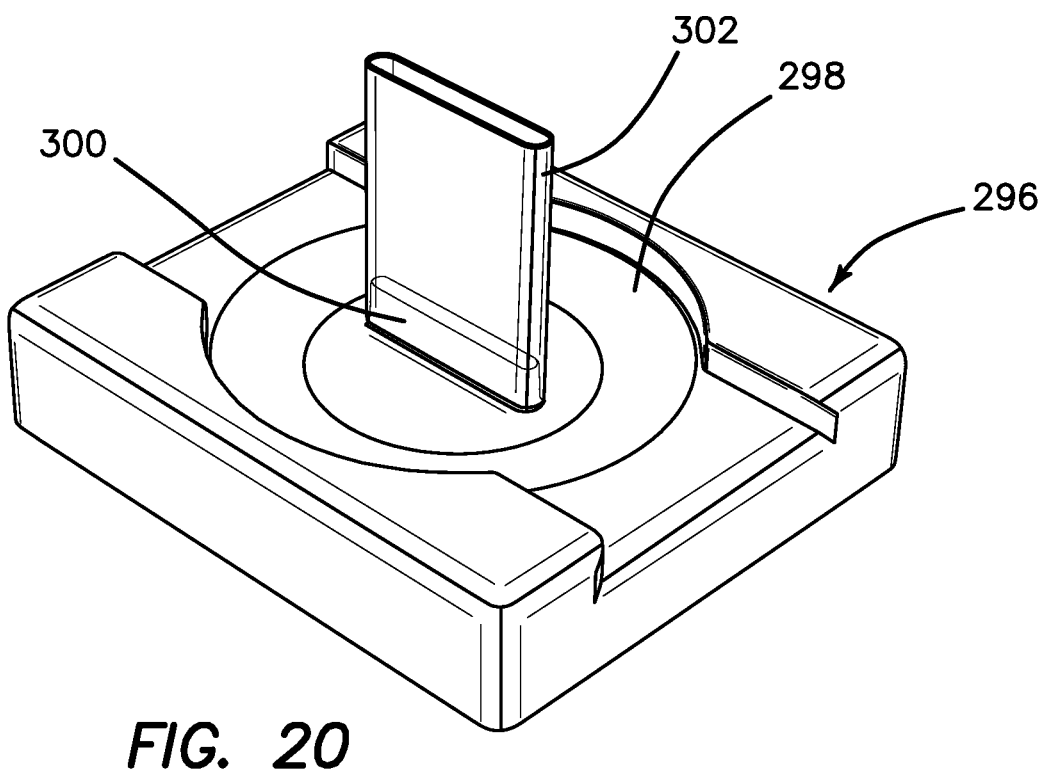
FIG. 20 is a top perspective view of a mold and a silicone tube placed over a center post of the mold according to the present invention.
Figure 21:
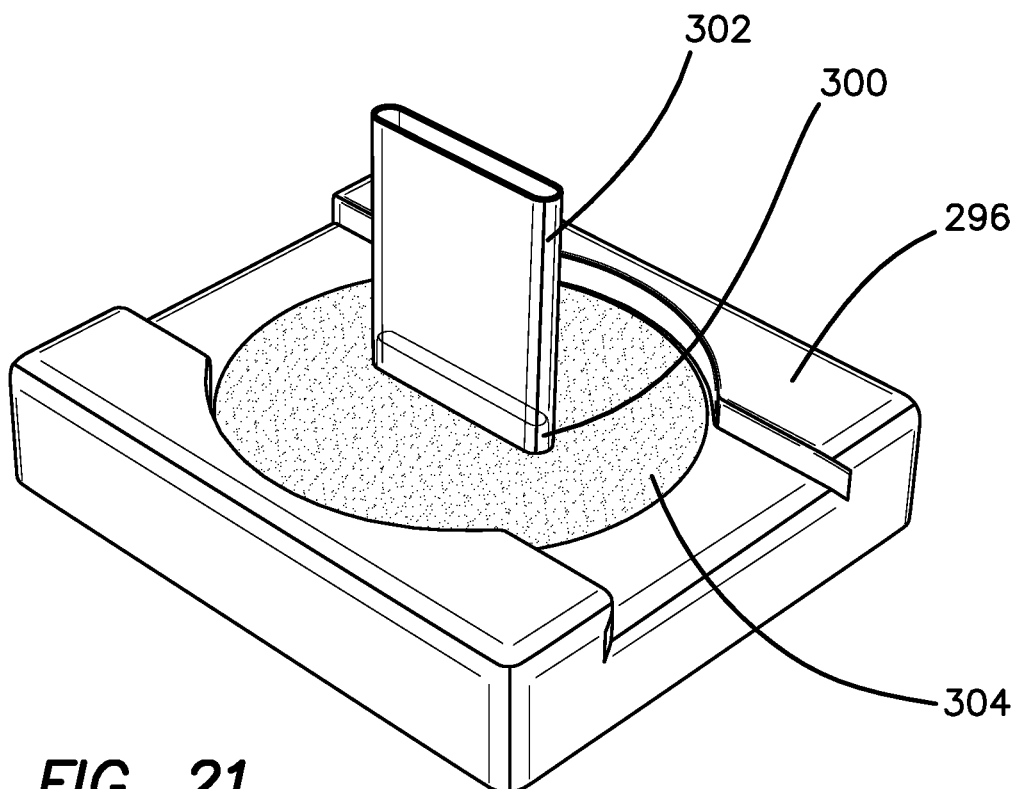
FIG. 21 is a top perspective view of a mold, a silicone tube placed over a center post and a silicone outer interface formed in the mold according to the present invention.
Figure 22:
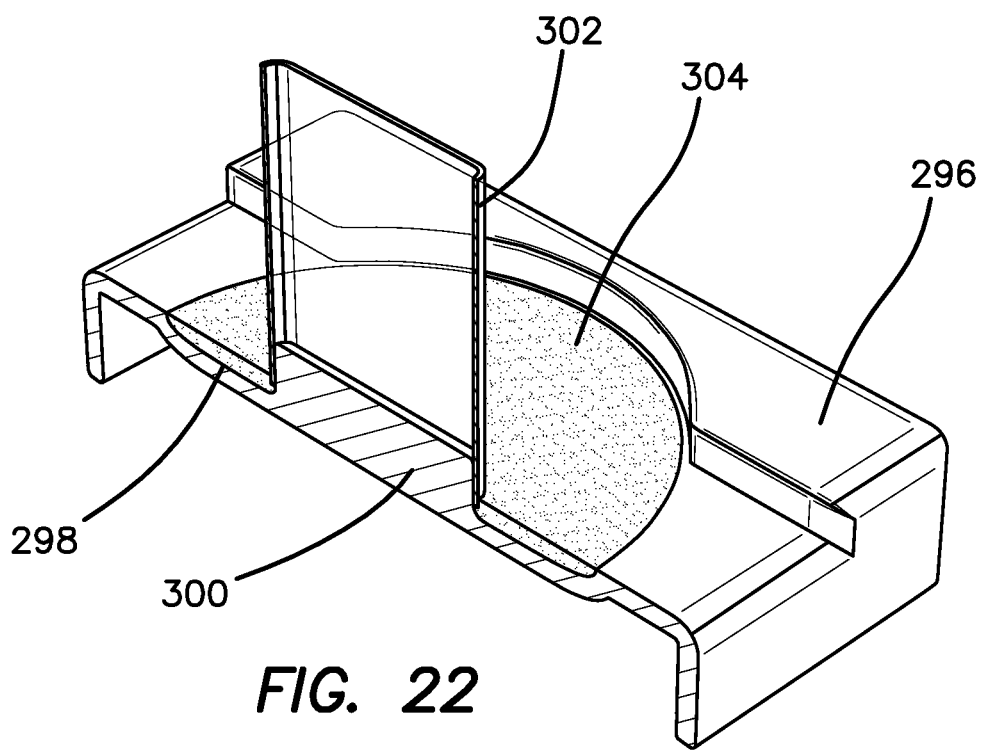
FIG. 22 is a cross-sectional view of a mold, a silicone tube placed over a center post and a silicone outer interface formed in the mold according to the present invention.
Figure 23:
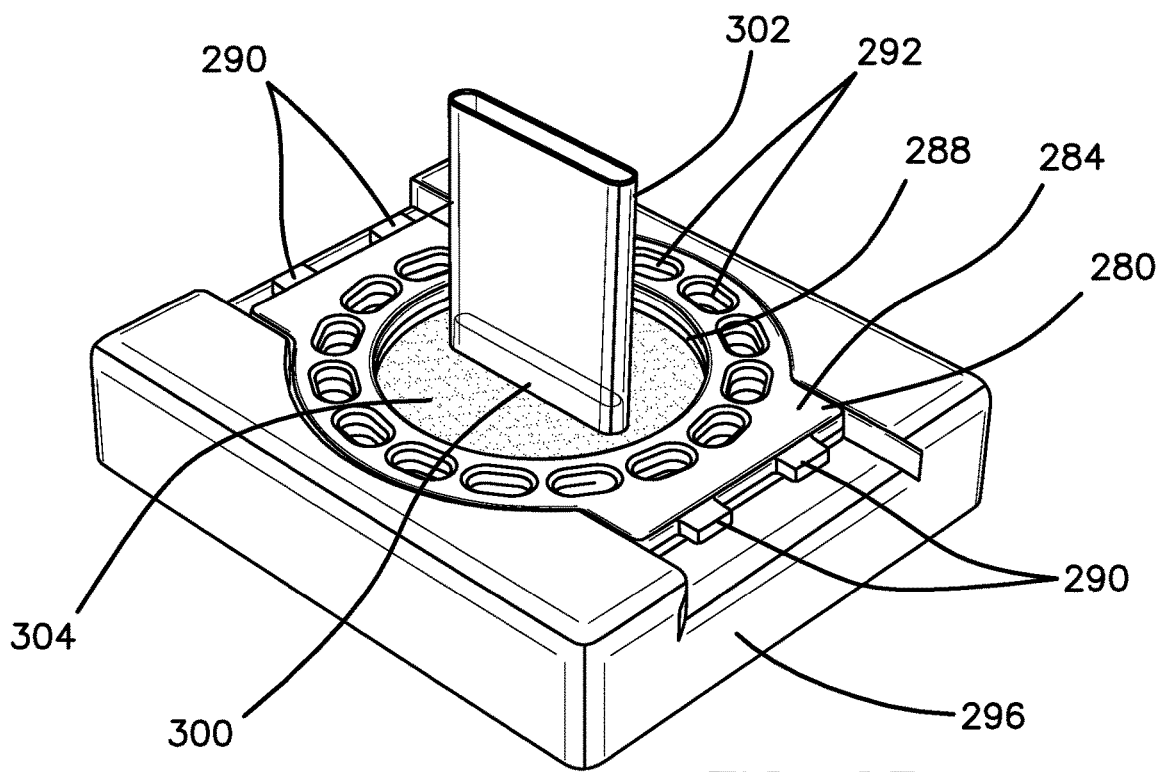
FIG. 23 is a top perspective view of a mold, a silicone tube placed over a center post, a silicone outer interface formed in the mold and a flat plate according to the present invention.
Figure 24:
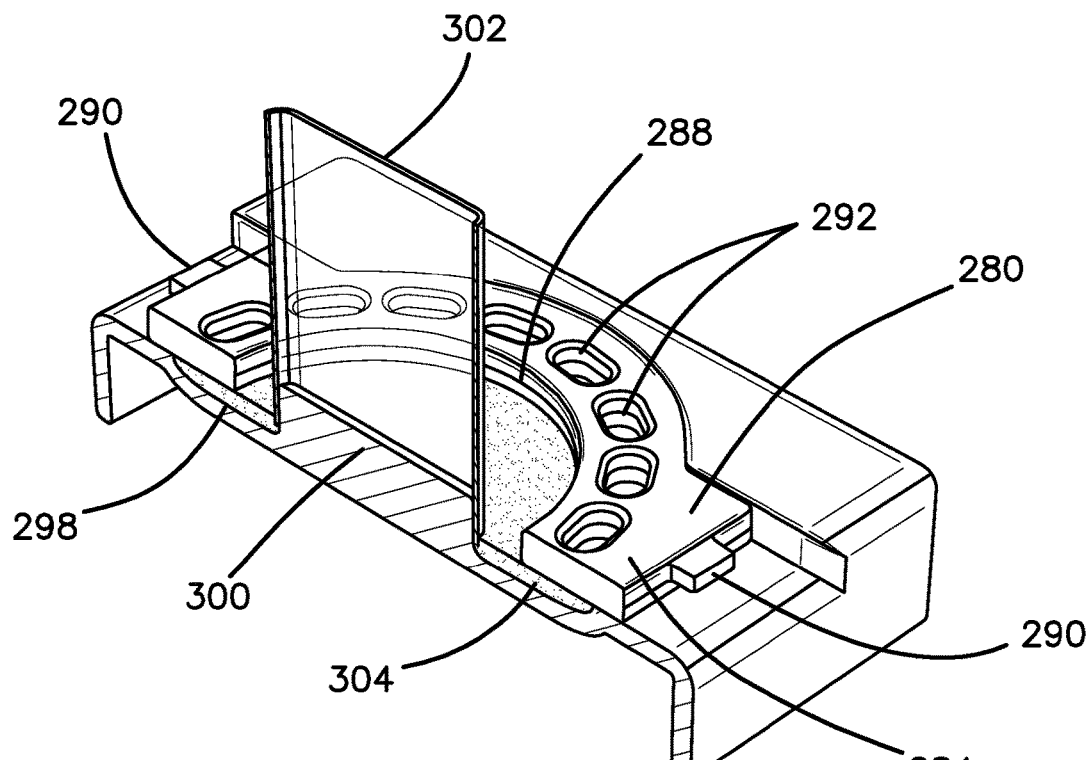
FIG. 24 is a cross-sectional view of a mold, a silicone tube placed over a center post, a silicone outer interface formed in the mold and a flat plate according to the present invention.
Figure 25:
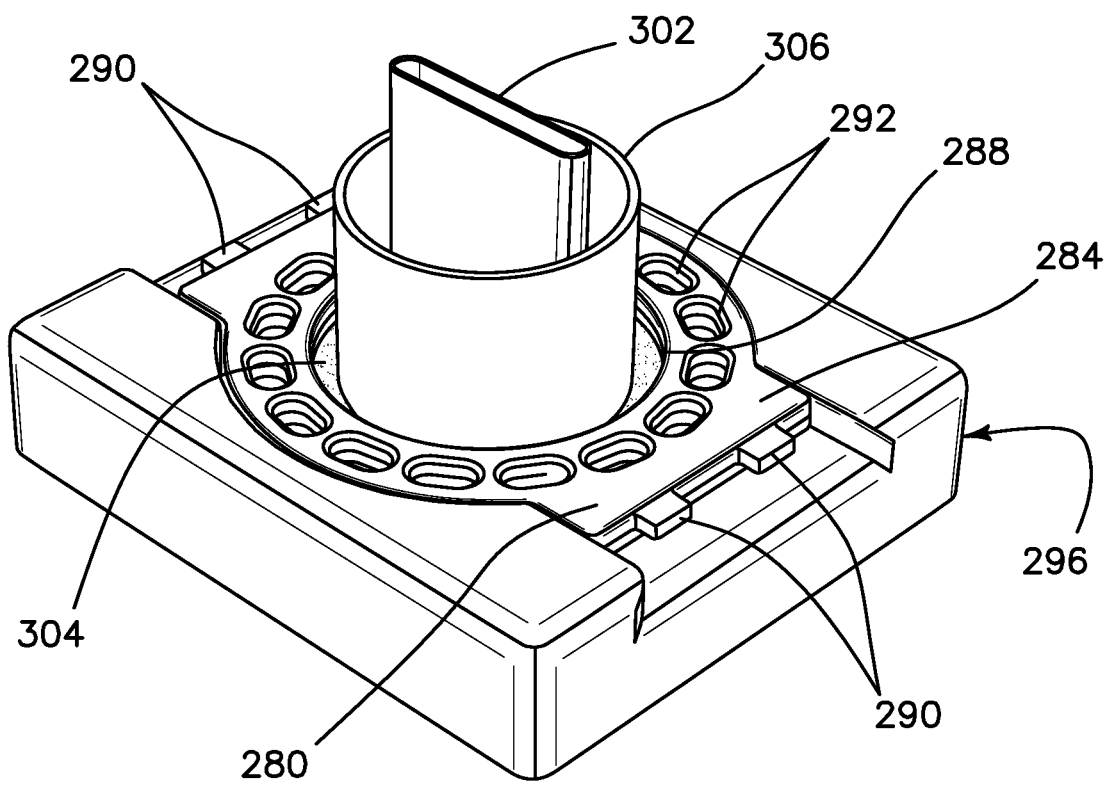
FIG. 25 is a top perspective view of a mold, a silicone tube placed over a center post, a silicone outer interface formed in the mold, a flat plate and a backing mold according to the present invention.
Figure 26:
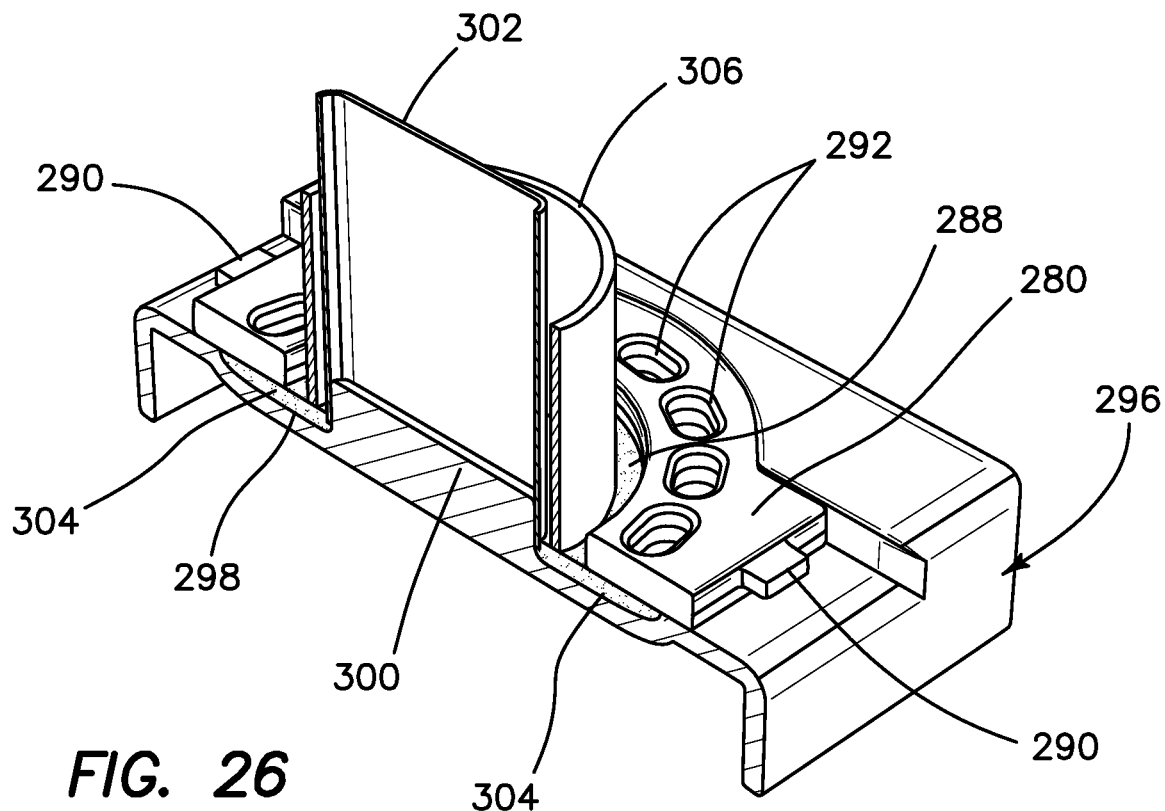
FIG. 26 is a cross-sectional view of a mold, a silicone tube placed over a center post, a silicone outer interface formed in the mold, a flat plate and a backing mold according to the present invention.
Figure 27:
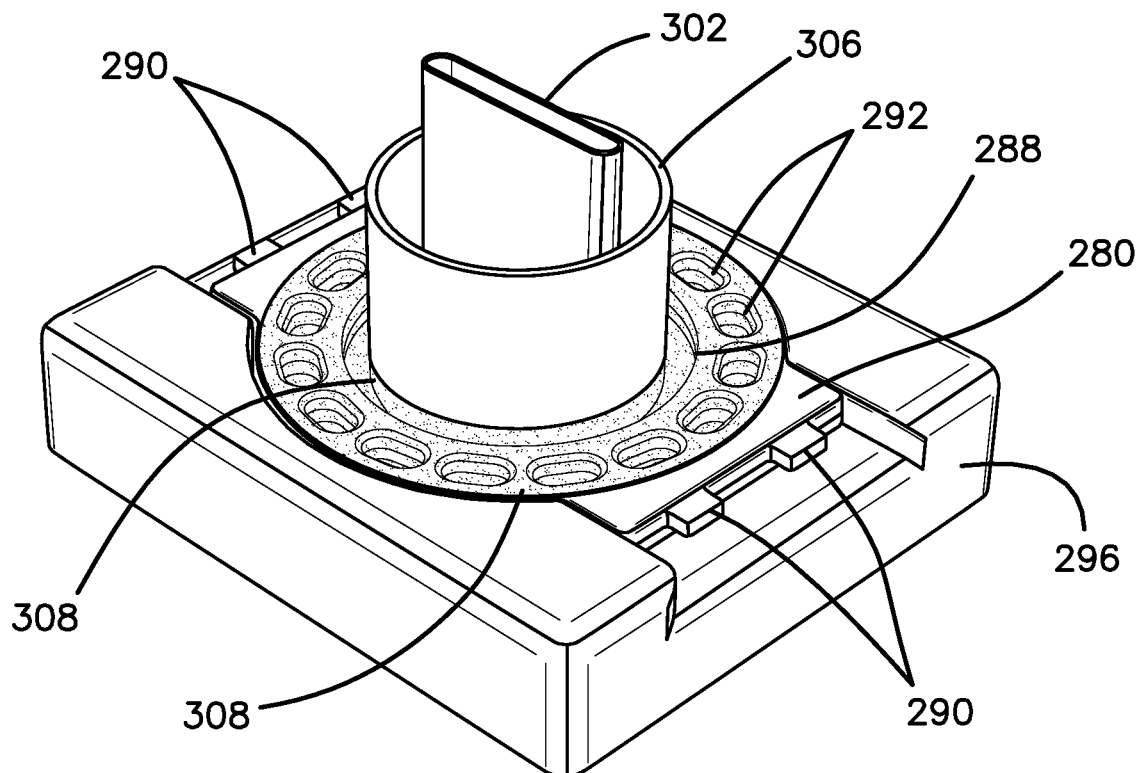
FIG. 27 is a top perspective view of a mold, a silicone tube placed over a center post, a silicone outer interface formed in the mold, a flat plate, a backing mold and a silicone inner interface according to the present invention.
Figure 28:
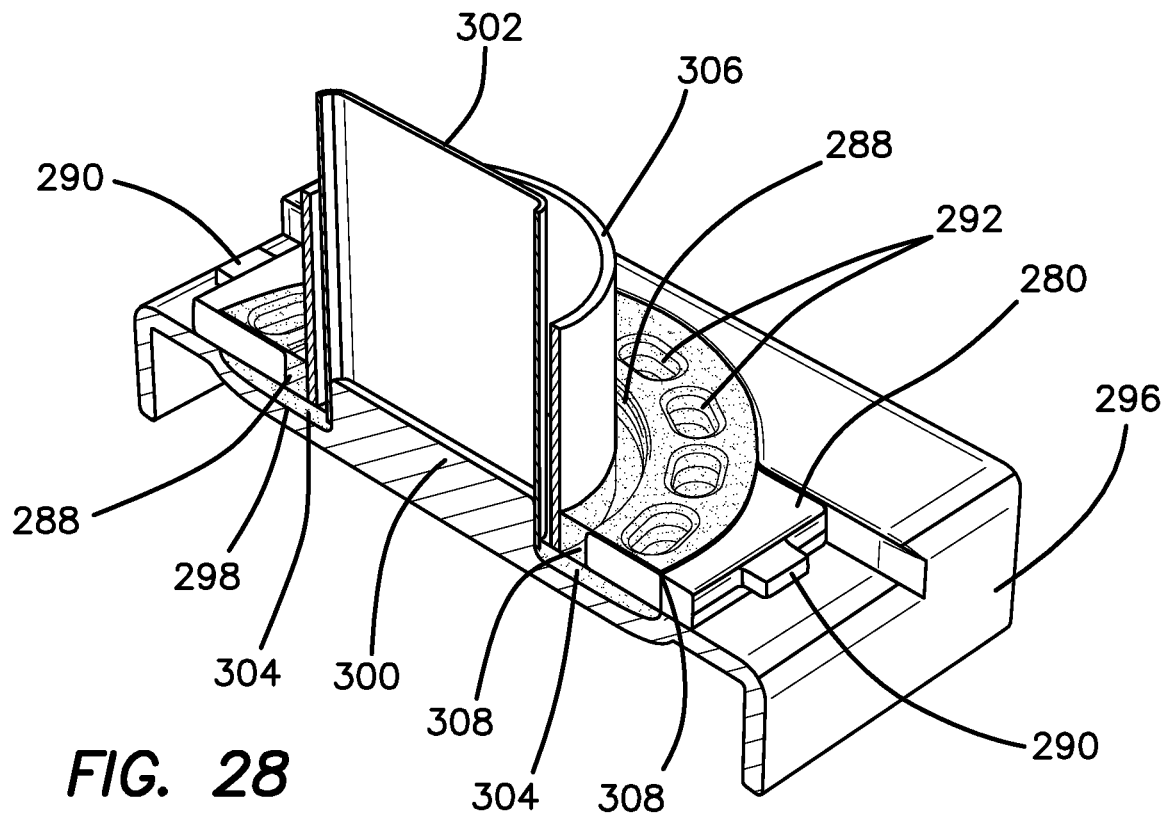
FIG. 28 is a cross-sectional view of a mold, a silicone tube placed over a center post, a silicone outer interface formed in the mold, a flat plate, a backing mold and a silicone inner interface according to the present invention.

Turning now to FIG. 19, a mold 298 is provided. The mold 298 includes a well 298 encompassing an elongated center post 300. In another variation, the center post 300 is oval or circular in shape. The circular or oval shape will result in an opening having the same shape and suitable for a TATME application in which the adapter is connectable to a simulated rectum and, thereby, serves as a transanal adapter instead of a transvaginal adapter. A pre-made silicone tube 302 is placed over the center post 300 as shown in FIG. 20. Next, turning to FIGS. 21-22, uncured silicone is poured into the well 298 to form the outer interface 304. Next, turning to FIGS. 23-24, the transvaginal adapter 280 is placed on top of the uncured silicone located inside the well 298. The uncured silicone of the outer interface 304 is allowed to cure. Turning now to FIGS. 25-26, a backing mold 306 is placed around the silicone tube 302 and inside the aperture 288. Uncured silicone is then poured between the backing mold 306 and the inside of the aperture 288 and into the molding apertures 292 and onto the inner surface 284 and allowed to cure to form the inner interface 308 as shown in FIGS. 27-28. The mold 296 and the backing mold 306 are removed. The resulting transvaginal adapter 280 is shown in FIGS. 17-18. At least part of the flat plate 282 of the transvaginal adapter 280 is sandwiched between the inner interface 308 and the outer interface 304 as the wet silicone of the inner interface 308 adheres to the cured silicone of the outer interface 304 through the aperture 288 and the molding apertures 292. The inner interface 308 and the outer interface 304 provide a soft and realistic tissue appearance and feel. The transvaginal adapter 280 is connected between the top cover 16 and base 18 of the trainer 10. The model 200 is placed inside the body cavity 12 of the trainer 10 and connected to the transvaginal adapter 280 such that the silicone tube 302 faces the interior of the cavity 12 and is inserted into the proximal end 256 of the simulated vaginal canal 218. The elongated center post 300 of the mold 296 creates an elongated entry way leading into the model 200.

In use, a practicing surgeon may approach the simulated uterus 216 with surgical instruments and retractors through the transvaginal adapter 280 to perform a transvaginal hysterectomy. Alternatively, the simulated uterus 216 may be approached through the simulated abdominal wall of the top cover 16 of the trainer 10. The user will practice laparoscopic surgical skills, employing a trocar and scope to examine the anatomy and perform the simulated surgical hysterectomy. The procedure involves making key incisions to detach the uterus and then remove it. In particular, the model 200 advantageously provides the one or more dissecting layer 226 that includes fibers embedded in silicone that make the incisions and separation of the simulated uterus 216 realistic. The user may further practice suturing the simulated vaginal canal 218 after removal of the simulated uterus 216. For this purpose, the simulated vaginal canal 218 is provided with an embedded mesh that makes it possible for the silicone to hold sutures without easily tearing. After use, the model 200 is removed from the trainer 10 and the plurality of simulated organ structures 202 is removed from the model 200 by releasing the fasteners 212 from the frame 204. A new plurality of simulated organ structures 202 is then connected to the frame 204 and inserted into the trainer 10 for continued practice.

Figure 29:
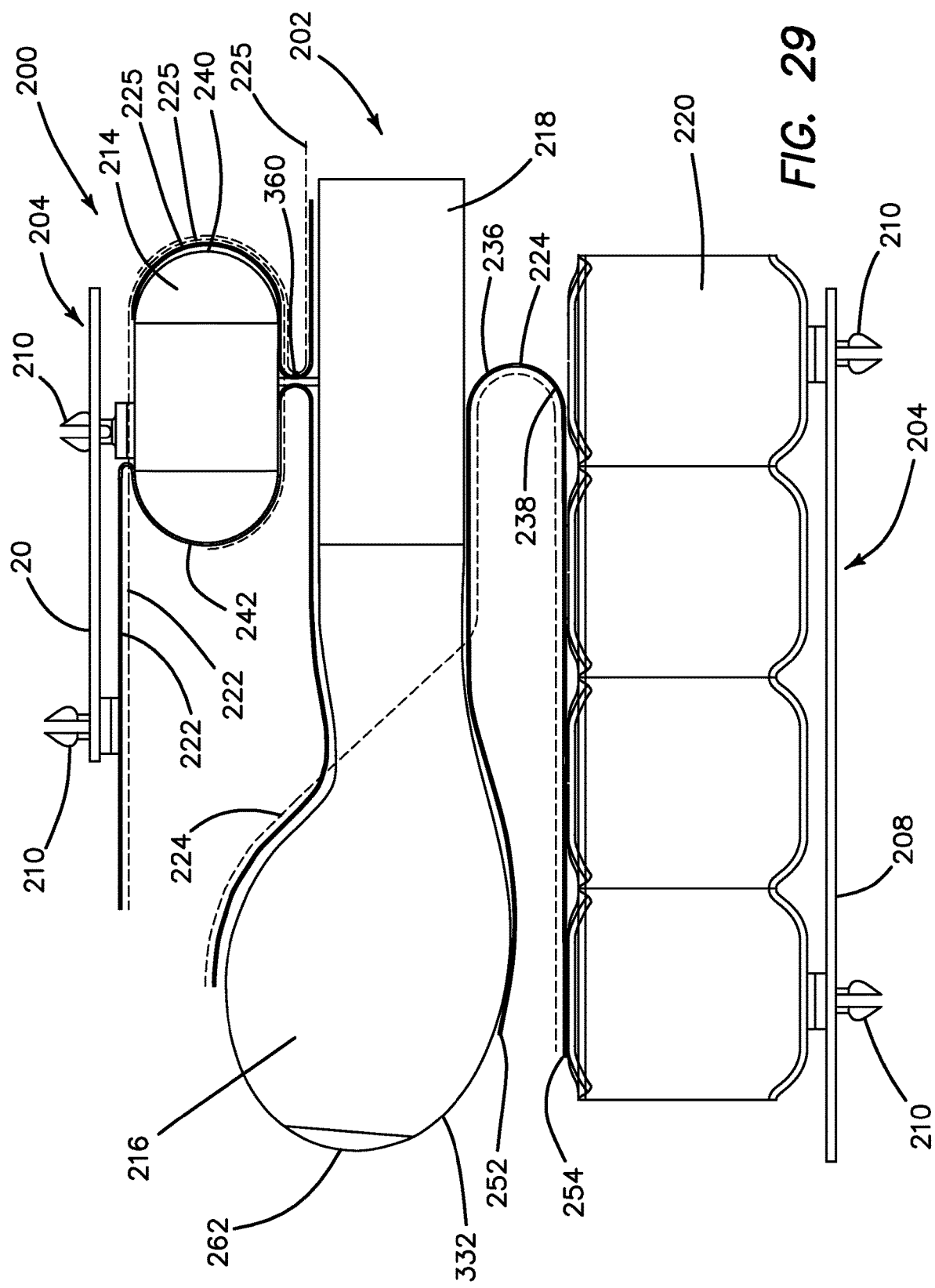
FIG. 29 is a side elevational, partial cross-sectional view of a hysterectomy model according to the present invention.
Figure 30:
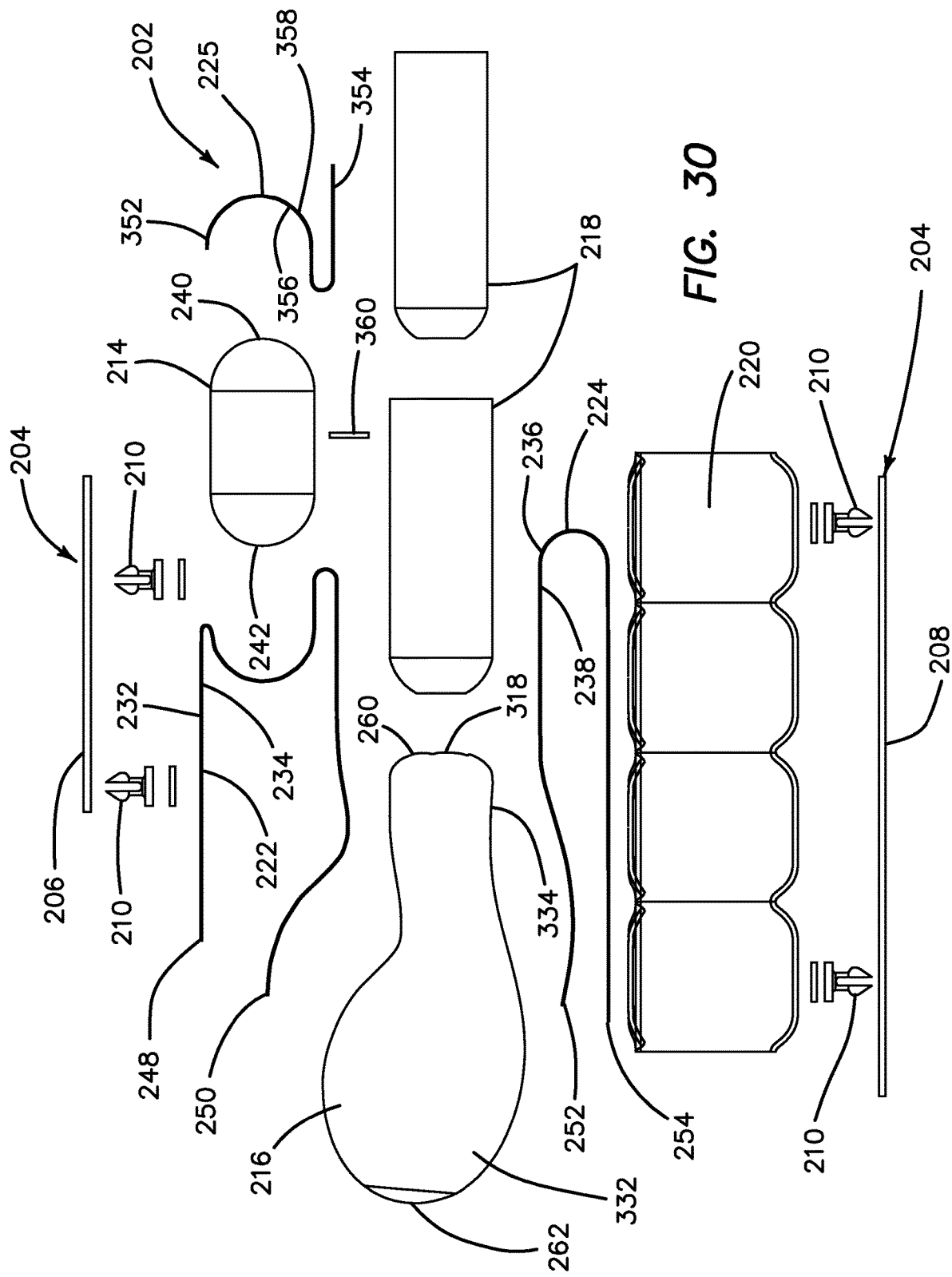
FIG. 30 is a side elevational, exploded view of a hysterectomy model according to the present invention.

Turning now to FIGS. 29-30, another variation of the hysterectomy model 200 will now be described. The model 200 is similar to the model 200 described with respect to FIGS. 7-28 and like numbers will be used to describe like parts. The model 200 includes a plurality of simulated organ structures 202 connected to and located inside a frame 204.

Figure 31:
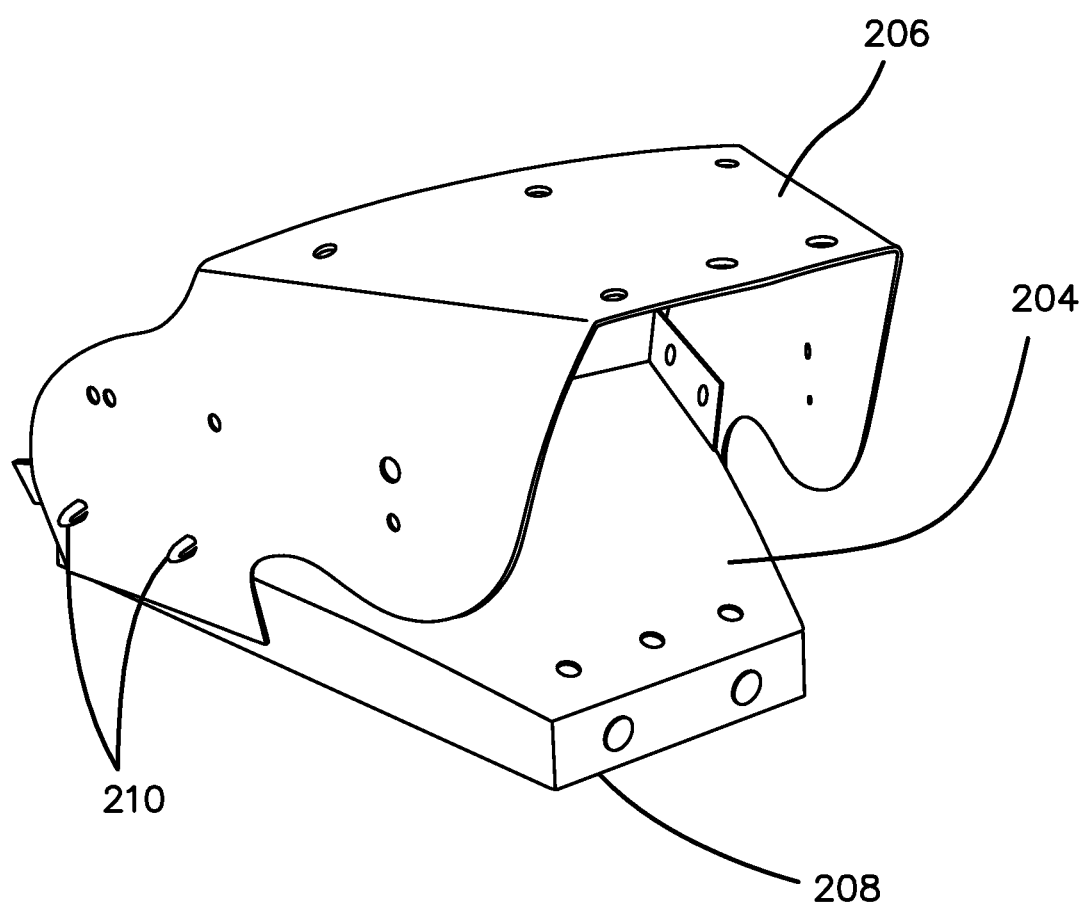
FIG. 31 is a top perspective view of a frame according to the present invention.

Turning briefly now to FIG. 31, there is shown a frame 204 according to the present invention. The frame 204 is configured to simulate a pelvis and serve as a box-like encasement for housing the plurality of simulated organ structures 202. The frame 204 includes a top frame portion 206 connected with fasteners 210 to a bottom frame portion 208 to form a top planar surface and a bottom planar surface interconnected by two upstanding sidewalls. The top planar surface and the bottom planar surface are parallel with each other and form corners with the sidewalls that are approximately 90 degrees. The sidewalls are angled towards each such that at the proximal end the distance between the sidewalls is close and increases progressively with increasing distance toward the distal end where the sidewalls are farther apart from each other. The assembled frame 204 having a base and a top interconnected by two upstanding sidewalls defines a central lumen with an open proximal end and an open distal end. The area of the central lumen in cross-section taken perpendicular to the longitudinal axis increases progressively with increasing distance from the proximal end toward the distal end. The outer shape of the frame 204 can be dissimilar from the shape of the central lumen. Another example of a tapered frame that has a central lumen with increasing area and that does not have corners is a frame that forms a frusto-conical shape. The central lumen of one such variation has a frusto-conical shape. The outer shape of the frame may also match the tapered shape of the central lumen. The frame 204 has a flat base permitting it to be placed and stand on a flat surface. In one variation, the bottom frame portion 208 includes a first level and a raised second floor 209 that raises the level of the model inside the frame 204 to be in line with the transvaginal adapter 280. The frame 204 may include apertures 212 for passing of fasteners 210 and/or connecting tissue structures, such as vasculature, by passing them through the apertures and suspending them in the frame 204. The frame 204 of FIG. 31 is similar to the frame 204 shown in FIGS. 7-13 in which the frame 204 is comprised of folded plastic that is transparent and/or translucent. The folding of the plastic components of the frame 204 results corners that are representative of a pelvis that is not anatomically correct yet provides advantages needed in simulating laparoscopic procedures in exchange for the realism of an anatomically correct pelvis. These advantages include the mechanical constriction of organs located in the tapered proximal end having the smallest luminal cross-sectional area. The physical constriction of organs at the proximal end creates a more rigid response in the organs when manipulated by surgical instruments relative to the distal end where organs located therein are less constricted and freer to pendulate and more fluidly respond to manipulations with surgical instruments. The frame 204 of the present invention is an intentional simplification of the pelvis that combines variable resistance in the organs along the length of the longitudinal axis of the central lumen. The smaller opening to the central lumen at the proximal end of the frame is where the opening to the vaginal canal would be positioned when the organs are placed inside the frame. The proximal end of the frame is also oriented toward the transvaginal or transanal adapted for connection therewith. The distal end of the frame 204 is the location of the artificial uterus 216. The central lumen of the frame expands, widens and angles outwardly towards the distal end. This taper of the box-like frame widens relaxing the organs located therein and the narrow proximal end constricts the organs, limiting the range of motion of the organs relatively more as a result of supporting the organs in closer confines.

With reference back to FIGS. 29-30, the plurality of simulated organ structures 202 and its connection to the frame 204 will now be described. The plurality of simulated organ structures 202 includes a simulated bladder 214, a simulated uterus 216, a simulated vaginal canal 218, a simulated rectum 220, a first sheet 222, a second sheet 224, a third sheet 225 and a plurality of fasteners 210. The plurality of organ structures 202 are interconnected as shown in FIG. 29 and in turn connected to the frame 204. Alternatively, the first sheet 222, second sheet 224 and third sheet 225 are connected as shown in dotted lines in FIG. 29. In this variation, the first sheet 22 extends proximally along the top of the simulated bladder 214 and around the proximal end of the simulated bladder 214 downwardly and toward the distal end of the simulated bladder 214. In this variation, the simulated bladder 214 is not suspended with a fastener 210 as shown in FIG. 29. The third sheet 225 commences at the proximal end of the simulated bladder 214 and extends downwardly and is connected to the first sheet 222 at a location 360 that in this variation comprises a location of adhesive connecting the first sheet 222 and the third sheet 225. The second sheet 224 in this alternative variation follows approximately the same path but includes slit to pass the simulated uterus 216 through such that the second sheet 224 extends upwardly as shown with the dotted line. Tubular shaped vasculature, ducts, arteries and the like in addition to other simulated organs structures not mentioned herein may be included in this model in an anatomically correct or anatomically similar arrangement for the same or different anatomical location of the body. Each simulated organ structure will now be described.

The simulated bladder 214 forms a closed receptacle with an outer membrane made of pink-colored silicone. The interior of the simulated bladder 214 may be stuffed with polyfil or other material to maintain its shape. The simulated bladder 214 has a proximal end 240 and a distal end 242.

Figure 32:
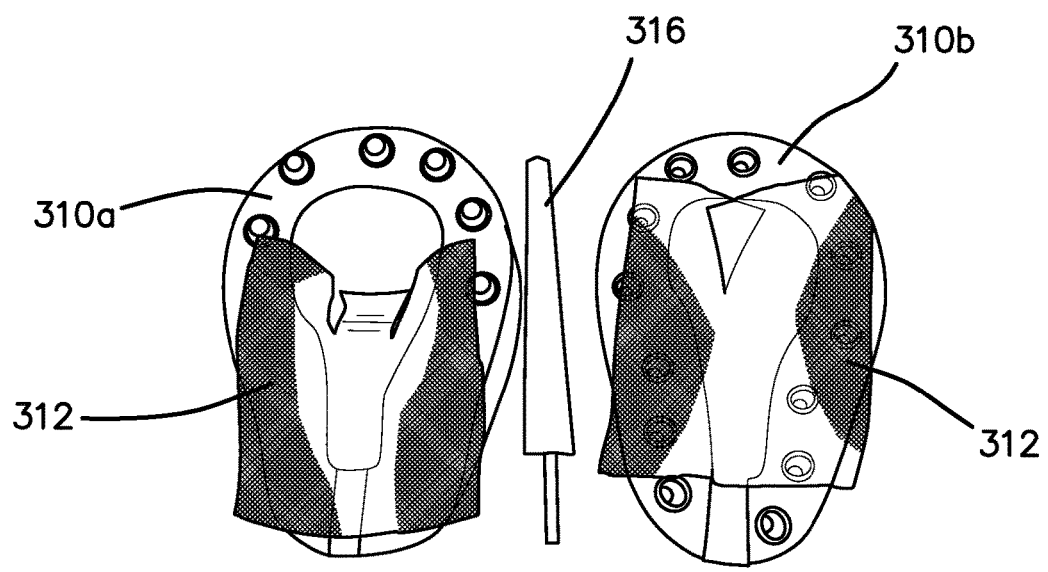
FIG. 32 is a top perspective view of a mesh inside an open uterine mold and a mandrel according to the present invention.
Figure 33:
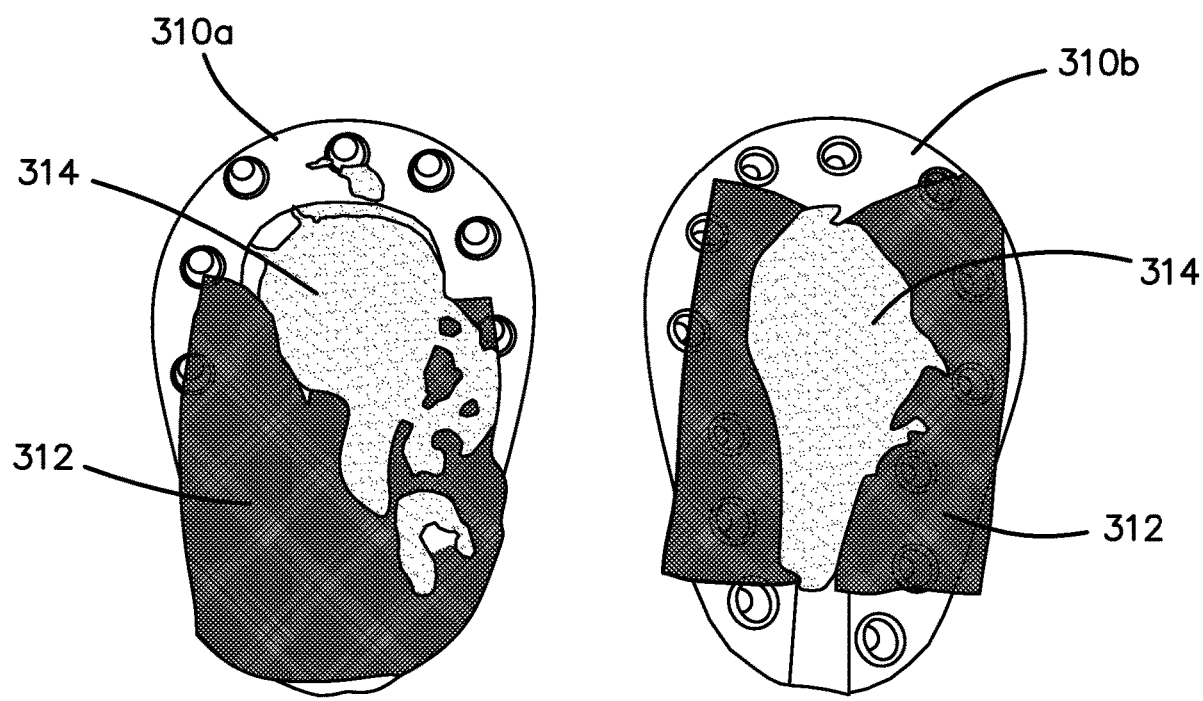
FIG. 33 is a top perspective view of mesh and silicone inside an open uterine mold according to the present invention.
Figure 34:
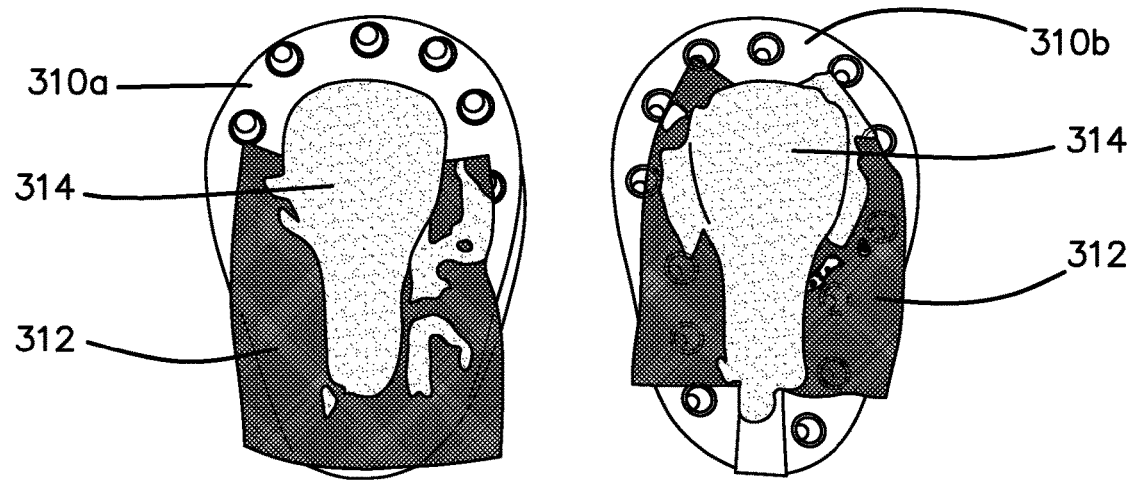
FIG. 34 is a top perspective view of mesh and silicone inside an open uterine mold according to the present invention.
Figure 35:
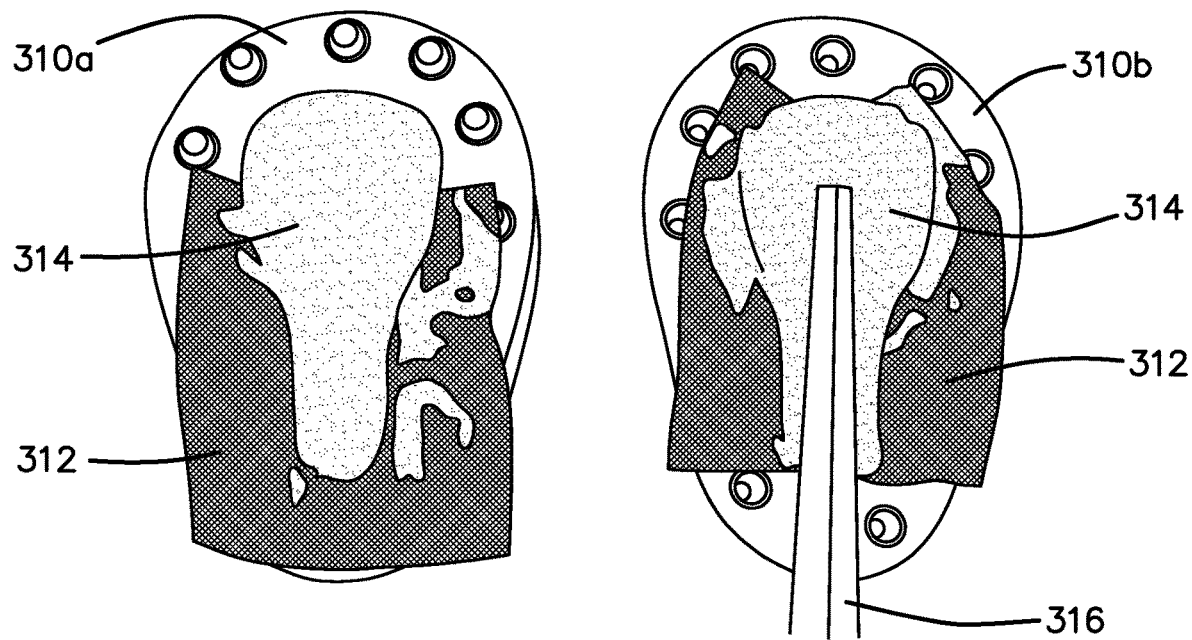
FIG. 35 is a top perspective view of a mesh, silicone and a mandrel inside an open uterine mold according to the present invention.
Figure 36A:
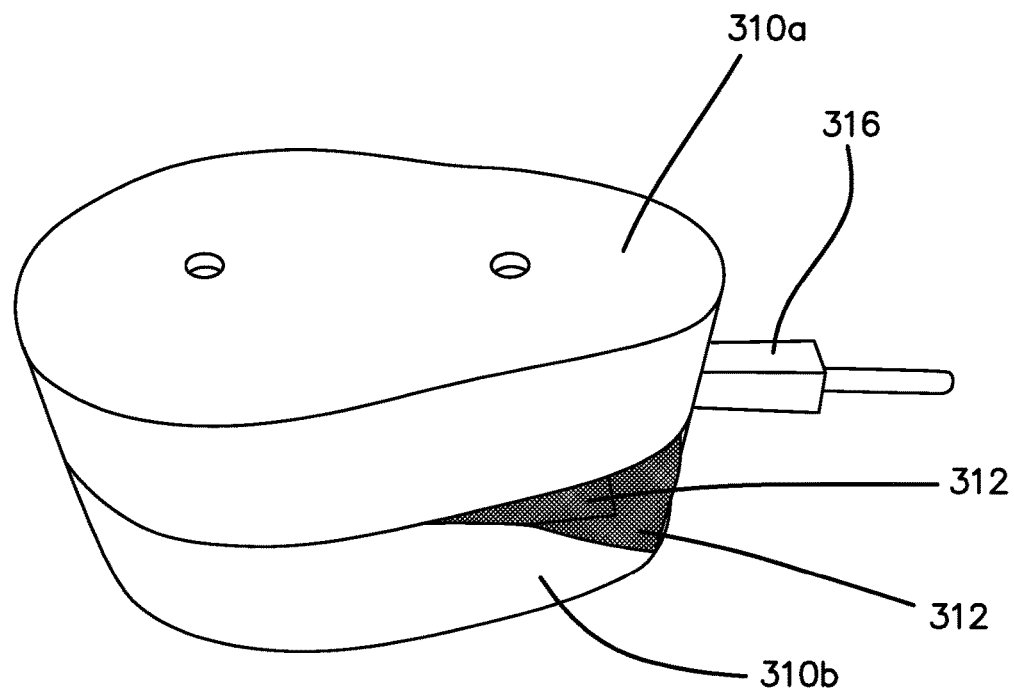
FIG. 36A is a top perspective view of mesh, silicone and a mandrel inside a closed uterine mold according to the present invention.
Figure 36B:
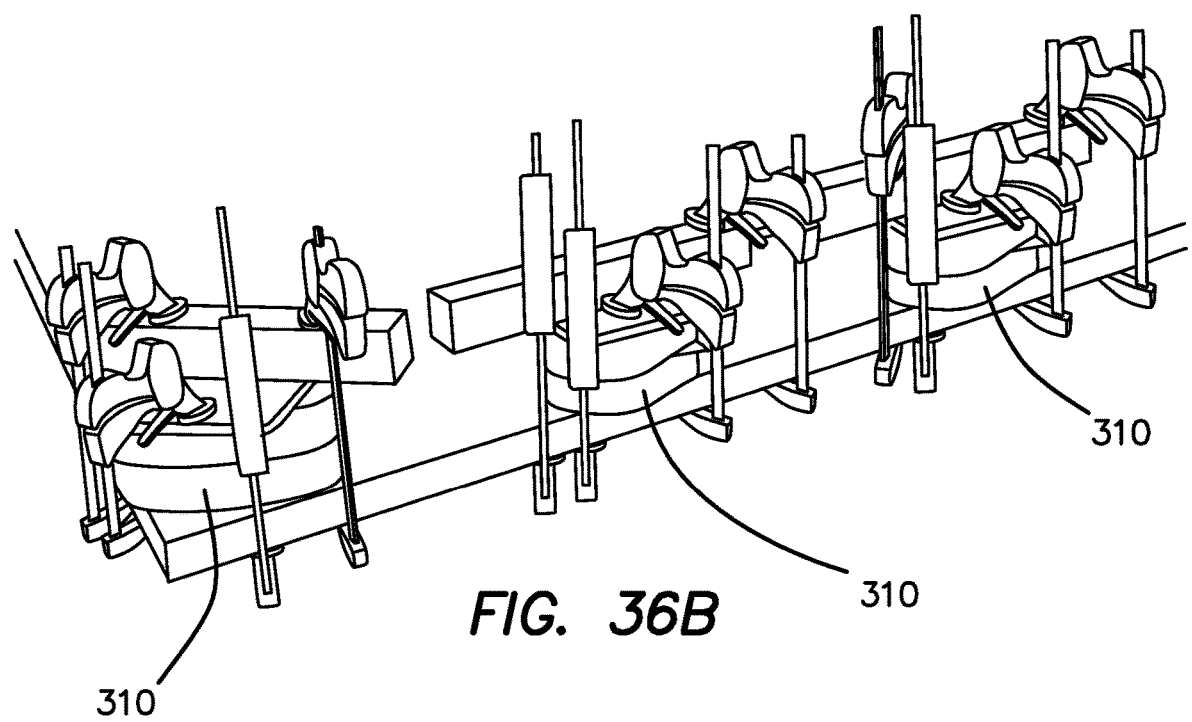
FIG. 36B is a top perspective view of a plurality of closed and clamped uterine molds according to the present invention.
Figure 37:
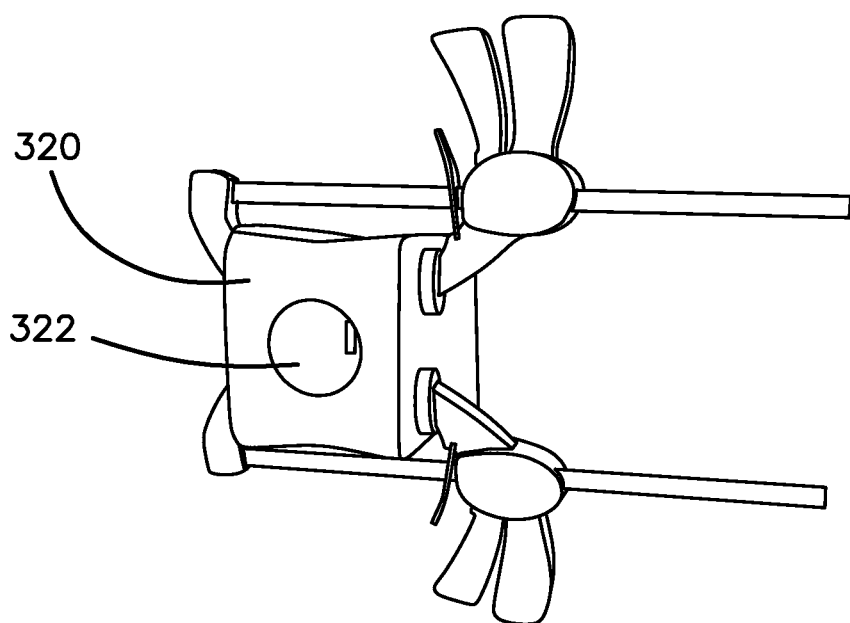
FIG. 37 is a top perspective view of a cervix mold according to the present invention.
Figure 38A:
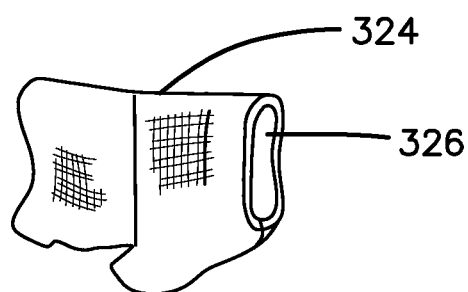
FIG. 38A is a top perspective view of a folded fabric sleeve according to the present invention.
Figure 38B:
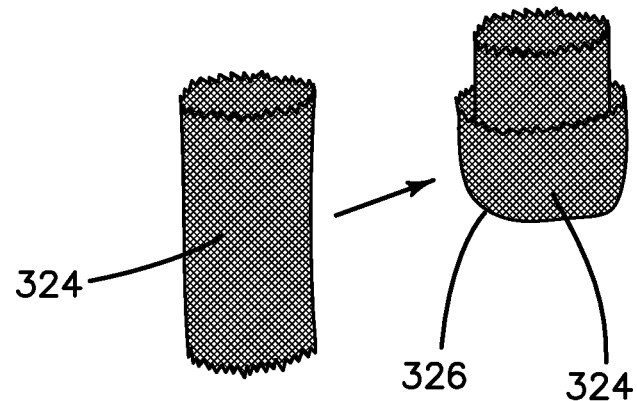
FIG. 38B is a top perspective view of a tubular sleeve being folded unto itself to create a folded sleeve having two layers of fabric according to the present invention.
Figure 39:
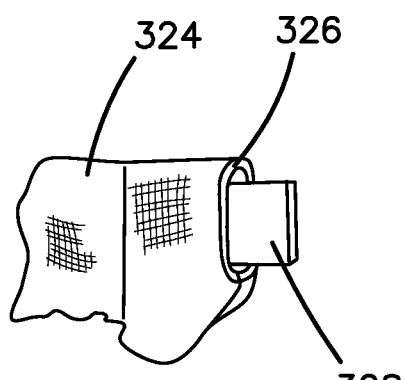
FIG. 39 is a top perspective view of a post inside a fabric sleeve according to the present invention.
Figure 40:
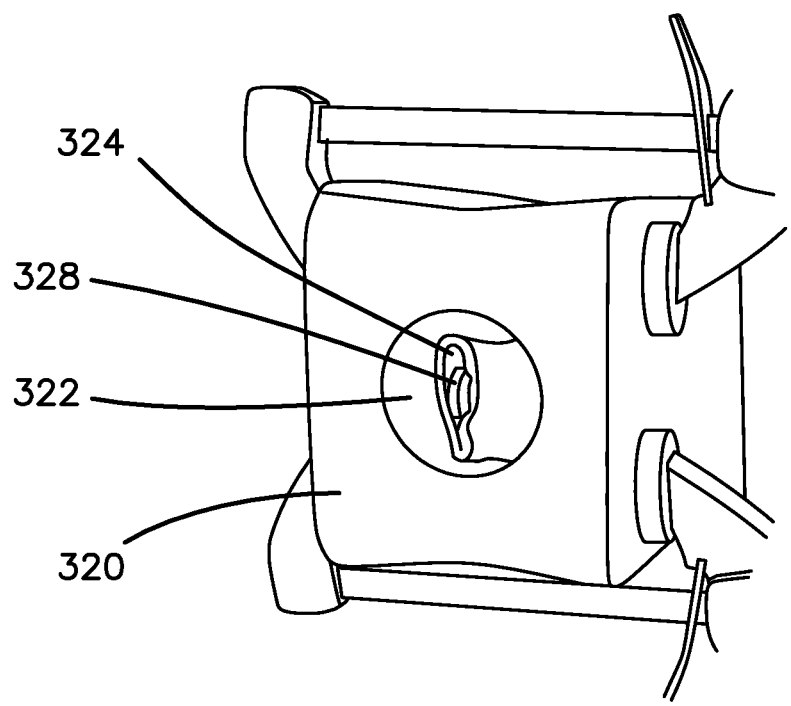
FIG. 40 is a top perspective view of a post inside a fabric sleeve inside a well of a cervix mold according to the present invention.
Figure 41A:
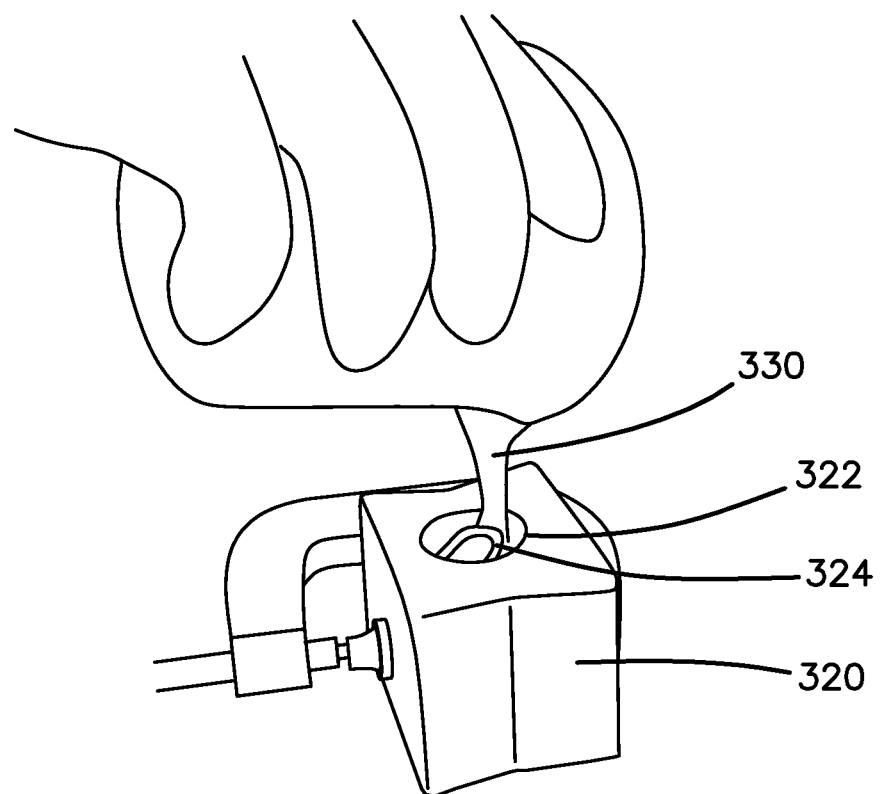
FIG. 41A is a top perspective view of uncured silicone being poured into a cervix mold according to the present invention.
Figure 41B:
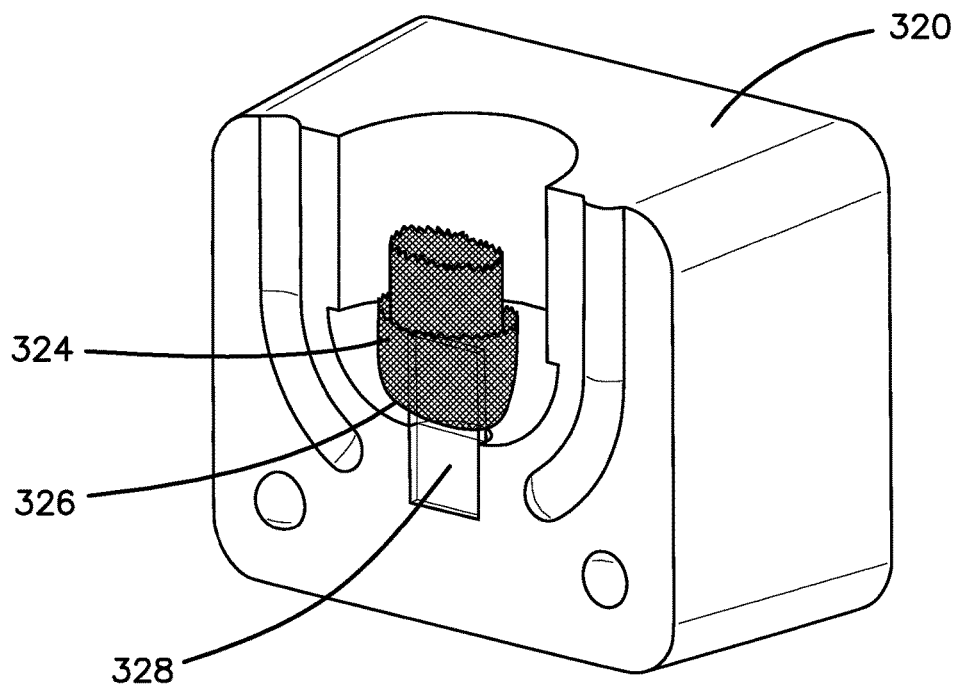
FIG. 41B is a cross-sectional view of a folded sleeve with a post inside a well of a cervix mold according to the present invention.
Figure 42:
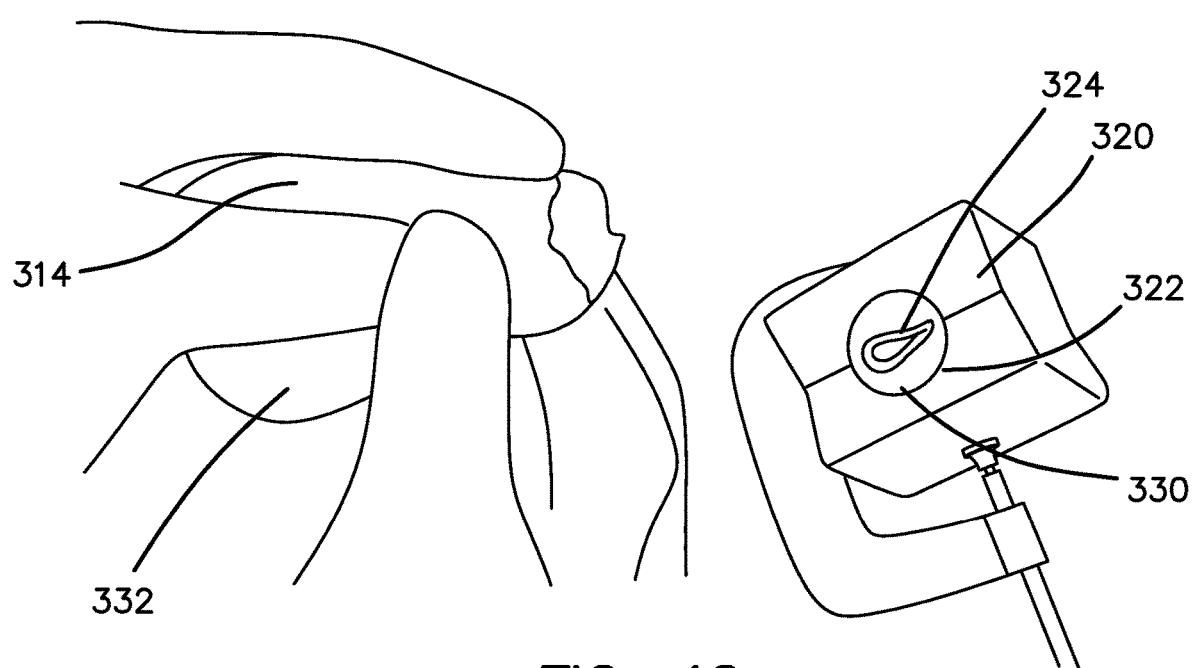
FIG. 42 is a top perspective view of a post inside a fabric sleeve inside a well of a cervix mold partially filled with uncured silicone and a uterine form being squeezed according to the present invention.

The simulated uterus 216 is also made of silicone. The simulated uterus 216 has a proximal end 260 and a distal end 262. The simulated uterus 216 is made by providing a uterine mold 310 comprising two halves 310a, 310b as shown in FIG. 32. A mesh fabric layer 312 is placed inside both halves the mold 310a, 310b. In one half of the mold 310a, the mesh fabric layer 312 is placed only in the proximal end of the mold 310 to reinforce that portion that will be subjected to the most force during practice of a surgical technique. The mesh fabric layer 312 may cover the entire mold in one variation. The mesh fabric layer 312 includes darts or cutouts to allow the fabric to lay as smoothly as possible in the mold. Uncured silicone foam 314 is poured over the mesh fabric layer 312 and into each half 310a, 310b of the mold 310 as shown in FIGS. 33-34. The wet silicone foam 314 is spread evenly to contact all of the surfaces to ensure that the silicone foam 314 will expand uniformly. As shown in FIG. 35, a mandrel 316 is placed onto half 310b the mold 310. The two halves 310a, 310b are placed together and the mold 310 is clamped as shown in FIGS. 36A and 36B and the silicone foam 314 is allowed to expand and cure. Upon curing, the mold 310 is removed from the cured silicone foam 314 and the mandrel 316 is mounted on a motor and the cured silicone foam is rotated and uncured silicone gel is applied evenly onto the silicone foam 314 to create an outer layer of silicone that encompasses the silicone foam 314. The outer layer of silicone is allowed to cure and the mandrel 316 is removed leaving behind a uterine-like form 332 shown in FIGS. 29-30 and 43-45. Next, a simulated cervix 318 is formed and inserted into the proximal end 260 of the cured foam and cured outer layer of silicone. The simulated cervix 318 is formed by first providing a cervix mold 320 having a well 322 as shown in FIG. 37. The cervix mold 320 is generally made of two pieces that are clamped together to define the well 322. A sleeve 324 of fabric such as KEVLAR synthetic fiber fabric is provided and inverted to create a fold 326 wherein the thickness of one end of the sleeve 324 is doubled as shown in FIGS. 38A, 38B and 39. The KEVLAR synthetic fiber reinforcement of the simulated cervix makes the portion of the cervix that is pulled by the surgeon strong and allows the surgeon to use a tenaculum with an ability to puncture and pull the simulated cervix as in real surgery without the model tearing. Also, at the same time, the fabric sleeve is compatible with silicone in that it does not inhibit the curing of room temperature vulcanizing (RTV) silicone elastomers that form the rest of the artificial cervix, uterus and vaginal canal. Because KEVLAR synthetic fiber is porous, it allows for a strong mechanical connection without additional adhesive and can be used with materials other than silicone. Any suitable fiber having a high tensile strength-to-weight ratio may be employed. A post 328 is inserted into the lumen of the fabric sleeve 324 such that it protrudes outwardly from the proximal end having the fold 326 as shown in FIG. 39. The cross-section of the post 328 is elongate and narrow such that a wooden popsicle stick can serve as the post 328. The sleeve 324 with the post 328 is placed into the well 322 of the cervix mold 320 with the fold 326 and protruding post 328 being placed into the bottom of the well 322 as shown in FIGS. 40 and 41B. Wet silicone 330 is poured into the well 322 of the mold 320 such that approximately three quarters of the well 322 is filled with uncured silicone 330 full as shown in FIGS. 41A and 42. The proximal end of the form 332 comprising the cured silicone foam with a coating of silicone is squeezed to substantially close the hole left by the mandrel 316. The form 332 is squeezed to remove as much air as possible from out of the inside of the form 332 as shown in FIG. 42 and while still squeezing the form 332, the proximal end of the form 332 is inserted into the wet silicone 330 inside the well 322 of the cervix mold 320 as shown in FIG. 43 and released. When the form 332 is released, a negative pressure is equalized moving wet silicone 330 into the opening left by the removed mandrel 316 drawing wet silicone up into the mandrel hole and into and around the fabric sleeve 324. The wet silicone 330 inside the cervix mold 320 is allowed to cure and adhere to the form 332 as shown in FIG. 44. The cervix mold 320 is removed leaving behind the simulated uterus 216 that includes the form 332 comprising the silicone foam 314 and overcoat of silicone and the attached simulated cervix 334 at the proximal end as shown in FIG. 45. The post 328 is removed to define a narrow opening 338 at the proximal end 260 of the simulated uterus 216 that is reinforced with the fabric sleeve 324 as clearly seen in FIGS. 46A and 46B. The fabric sleeve 324 advantageously reinforces that portion of the simulated uterus 216 that is grasped strongly by the surgeon in practicing a hysterectomy. The fabric sleeve 324 remains inside the simulated cervix 334. The fold 326 in the sleeve 324 creates a smooth distal end such that individual threads of the fabric sleeve 324 do not protrude from the cured silicone at the proximal end 260 that would increase the chance of the sleeve 324 ripping when pulled during surgical practice. Any flash is trimmed from the simulated cervix 334. In one variation, the well 322 of the cervix mold 320 is provided with a circumferential ledge that forms a ridge 336 on the resulting simulated cervix 334. The ridge 336 is visible in FIG. 45 and is useful for connection to the vaginal canal 218 which will be described next.

Figure 47:
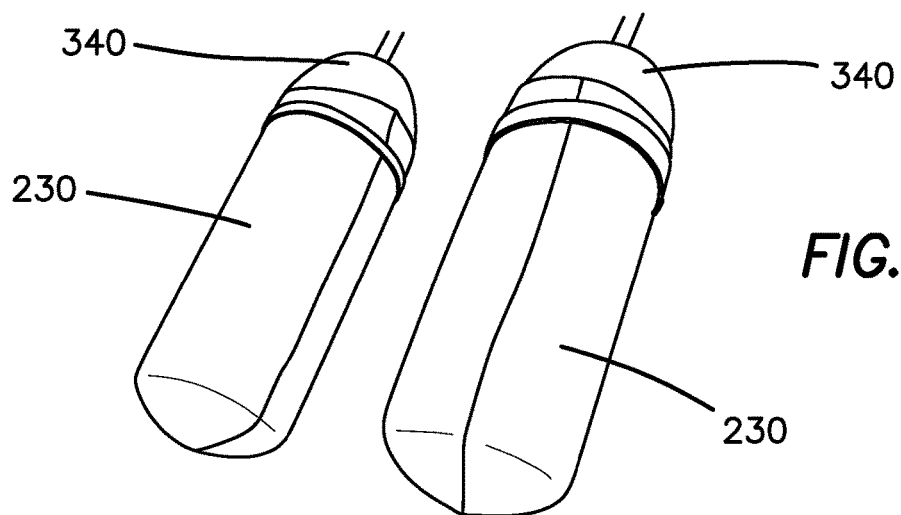
FIG. 47 is a top perspective view of a pair of mesh socks attached to a pair of mandrels according to the present invention.
Figure 48:
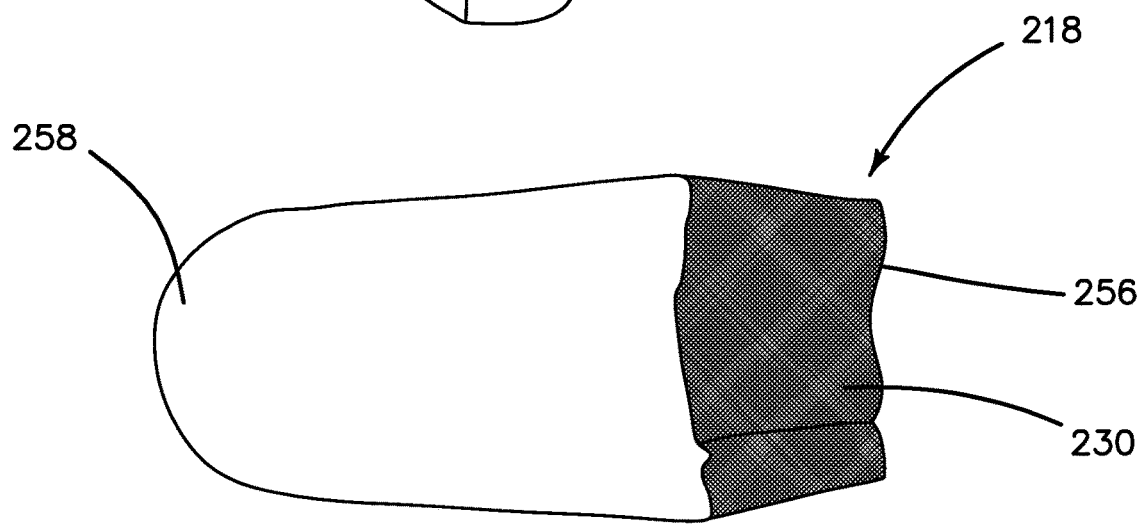
FIG. 48 is a top perspective view of simulated vaginal canal with an embedded mesh layer according to the present invention.
Figure 49:
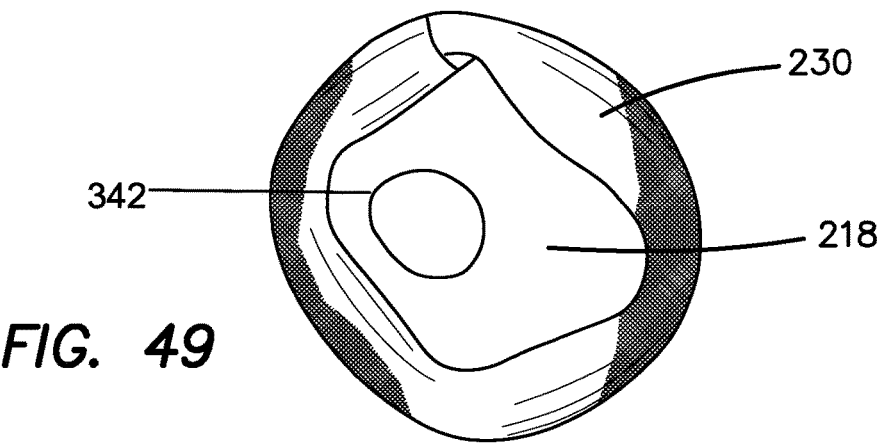
FIG. 49 is a top perspective view of a distal end of a simulated vaginal canal according to the present invention.
Figure 50:
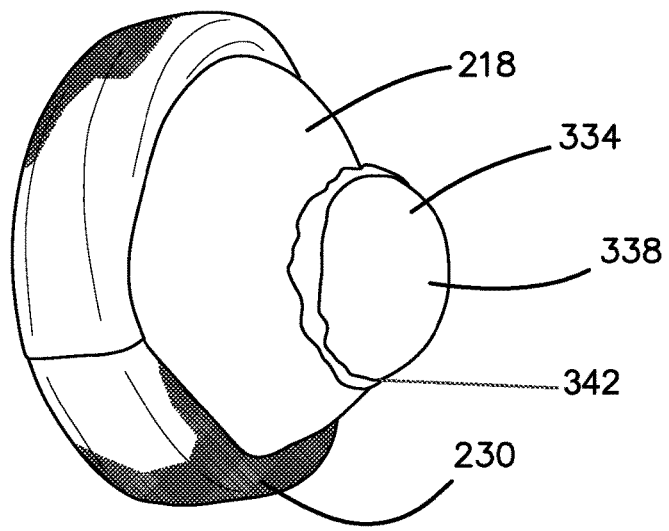
FIG. 50 is a top perspective view of a distal end of a simulated vaginal canal according to the present invention.
Figure 51:
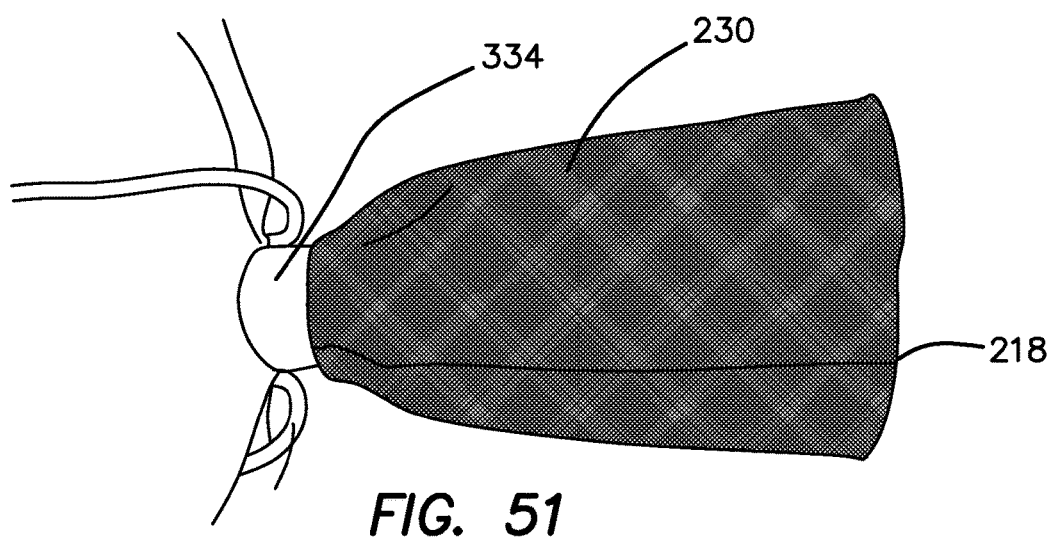
FIG. 51 is a top perspective view of an inverted simulated vaginal canal according to the present invention.
Figure 52:
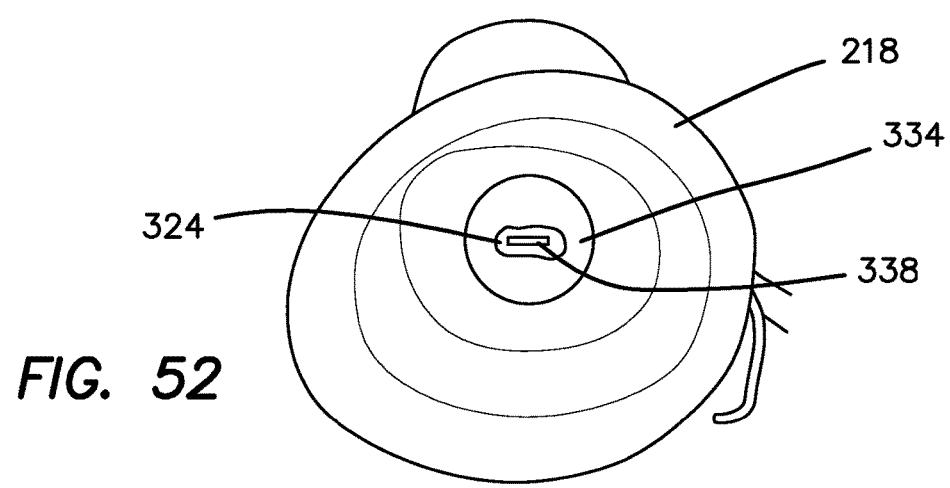
FIG. 52 is a proximal end view of simulated vaginal canal according to the present invention.

Turning now to FIGS. 47-52, the simulated vaginal canal 218 will be described. The simulated vaginal canal 218 is a tubular structure made of silicone and may optionally contain an embedded mesh layer 230. The simulated vaginal canal 218 has a proximal end 256 and a distal end 258. The mesh layer 230 is formed into a tubular shape having an open proximal end. The mesh layer 230 in the form of a sock is placed onto a mandrel 340 and attached with an elastic as shown in FIG. 47. Uncured silicone is applied onto the sock-like mesh layer 230 as the mandrel 240 is rotated to form a thin layer of silicone that embeds the mesh layer 230. The mesh layer 230 reinforcement advantageously prevents the propagation of a tear in the silicone/and/or foam and makes the artificial uterus pliable and strong and not cut resistant. In one variation, the mesh layer 230 can be made of KEVLAR para-aramid synthetic fiber or poly-paraphenylene terephthalamide or other substantial equivalent known to a person skilled in the art. The uncured silicone is allowed to cure and the simulated vaginal canal 218 is removed from the mandrel 240 as shown in FIG. 48. A hole 342 is punched through the domed distal end 258 of the simulated vaginal canal 218 such that the hole 342 is substantially coaxial with the longitudinal axis of the simulated vaginal canal 218. The hole 342 is visible in FIG. 49. The simulated vaginal canal 218 is attached to the simulated uterus 216. In particular, the simulated cervix 334 is pushed through the hole 342 of the distal end 258 of the simulated vaginal canal 218 as shown in FIG. 50. In particular, some adhesive is applied circumferentially around the simulated cervix 334 in the location of the ridge 336 and the simulated cervix 334 is pushed through the hole 342 until the ridge 336 just passes through the hole 342. The ridge 336 facilitates holding the simulated cervix 334 attached preventing it from easily backing out of the hole 342. The simulated vaginal canal 218 is inverted inside out and more adhesive is applied at the interface of the simulated vaginal canal 218 and simulated cervix 334 as shown in FIG. 51. FIG. 52 illustrates the resulting attached simulated vaginal canal 218 and proximal end of the simulated cervix 334 with the opening 338. The simulated vaginal canal 218 is enlarged to simulate a pre-retracted vaginal canal, allowing the user to practice with additional hands to aid in maintaining the retraction. Furthermore, the domed distal end of the simulated vaginal canal 218 that includes the hole 342 will invert as the simulated cervix 334 is pulled proximally through the lumen of the simulated vaginal canal 218 due to the dome effect and the adhesive. This feature advantageously closely represents what actually happens anatomically with real tissue.

Figure 53:
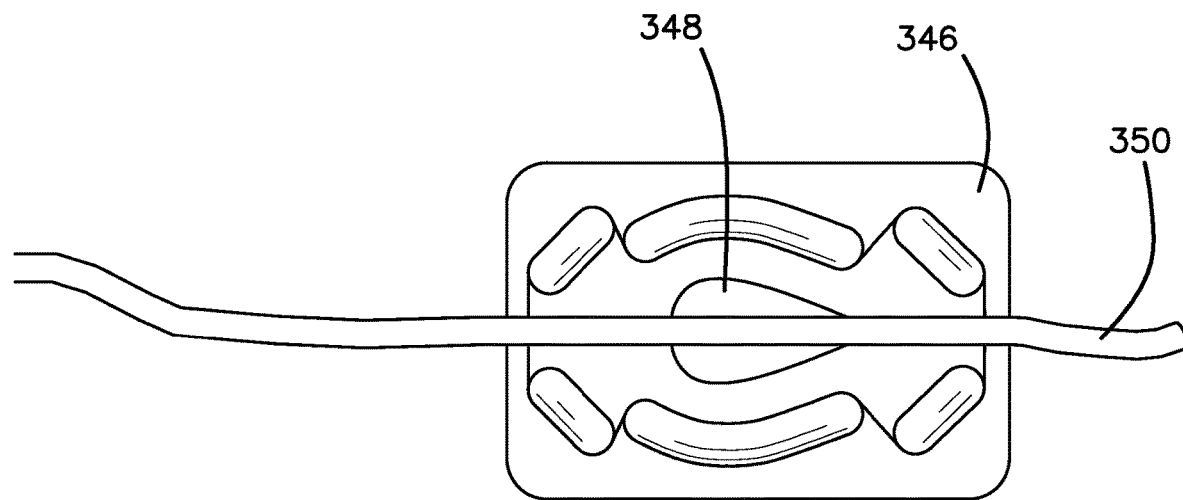
FIG. 53 is a top view of silicone vessel located across an ovary mold according to the present invention.
Figure 54:
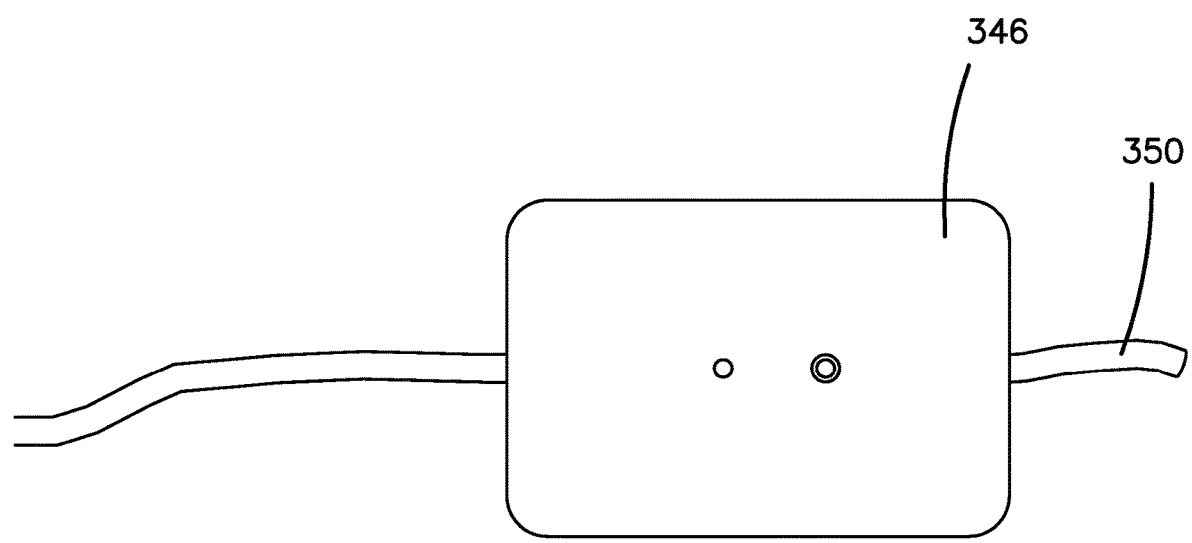
FIG. 54 is a top view of a silicone vessel located across an ovary mold according to the present invention.
Figure 55:
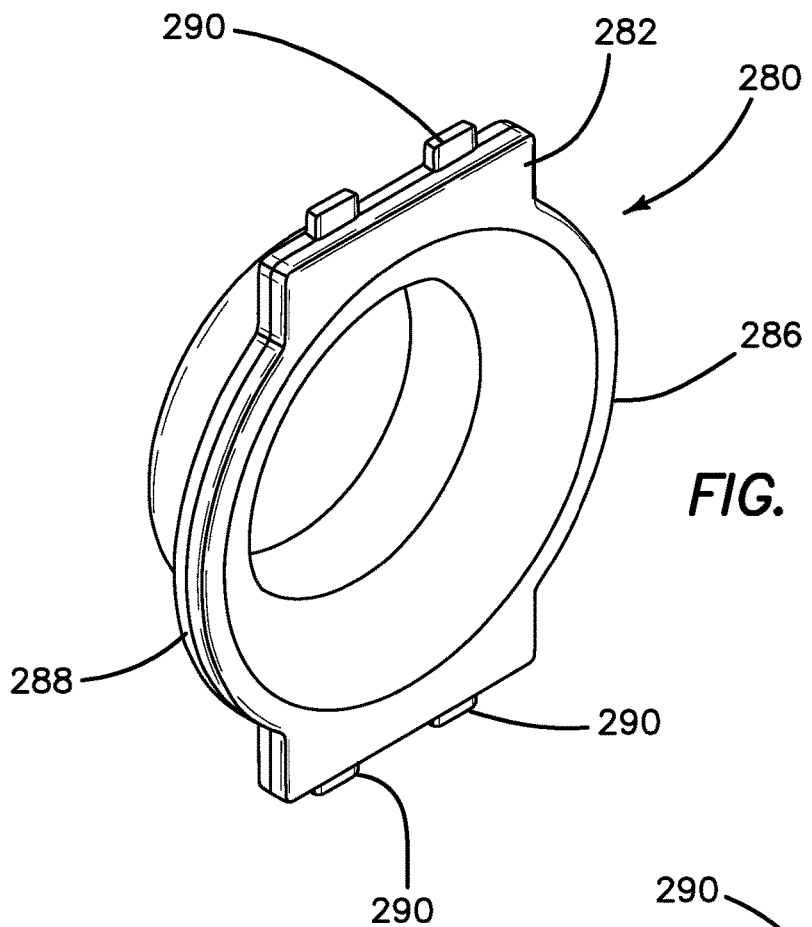
FIG. 55 is a top perspective view of a transvaginal adapter according to the present invention.
Figure 56:
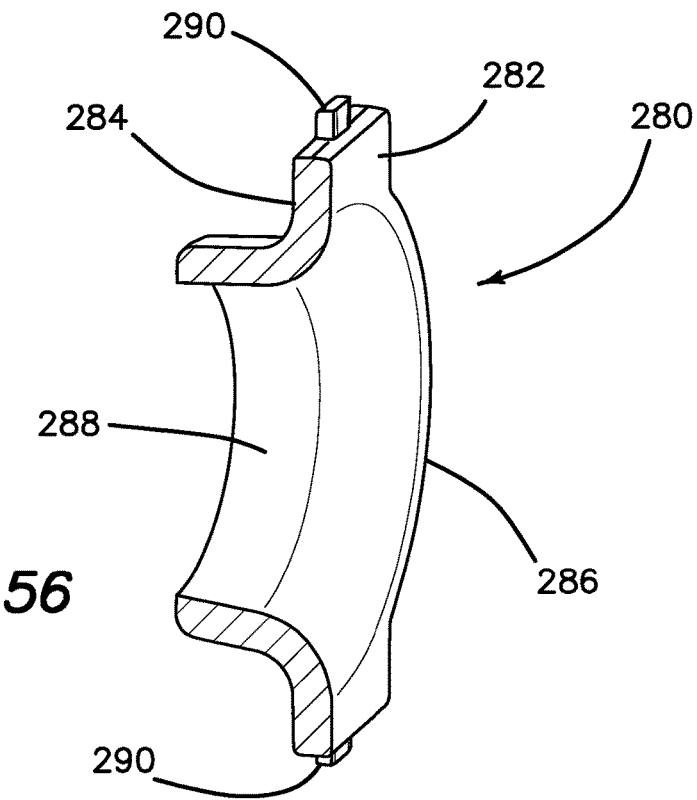
FIG. 56 is a top perspective sectional view of a transvaginal adapter according to the present invention.
Figures 57, 58:
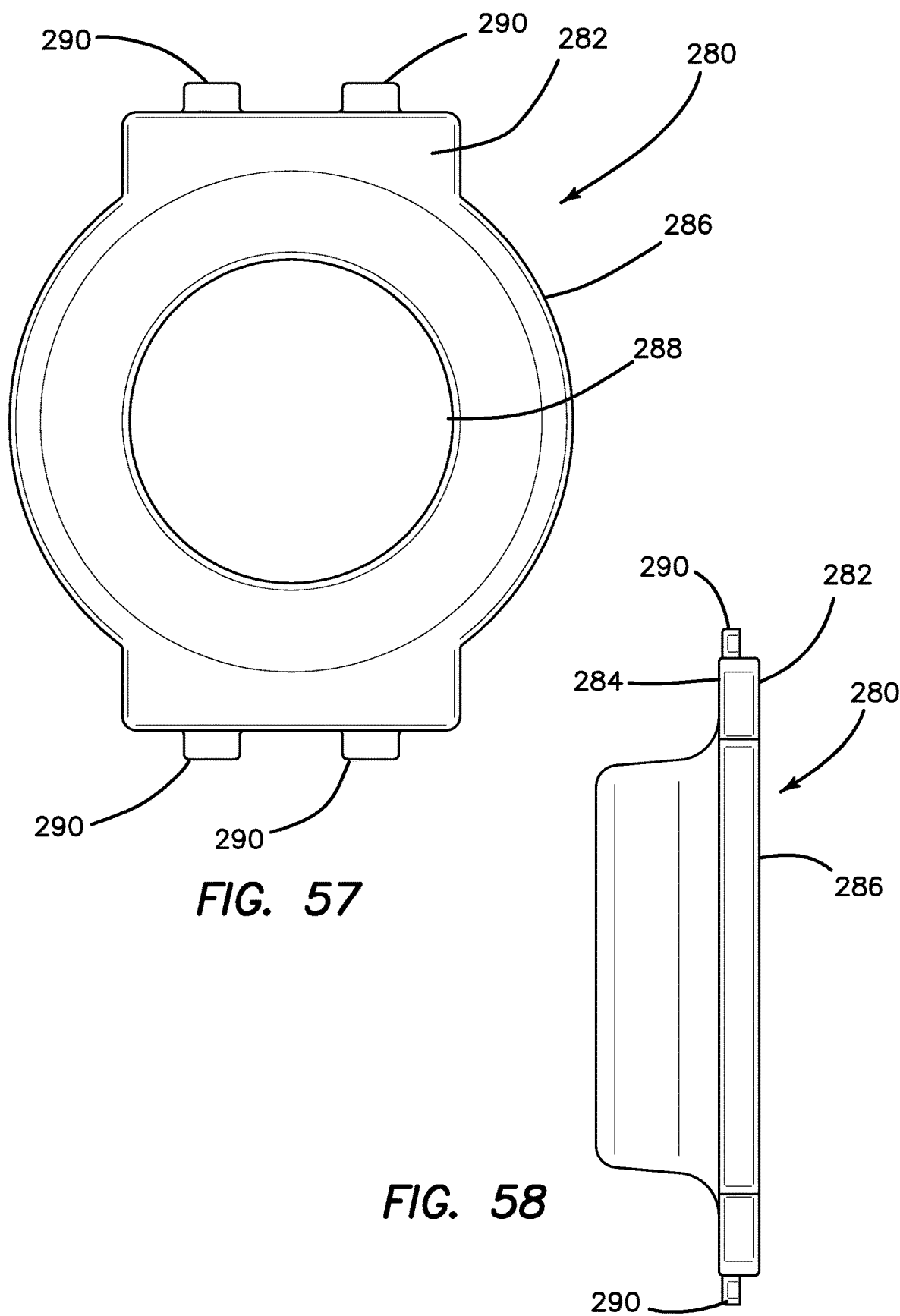
FIG. 57 is an end view of a transvaginal adapter according to the present invention.
FIG. 58 is a side view of a transvaginal adapter according to the present invention.
Figure 59:
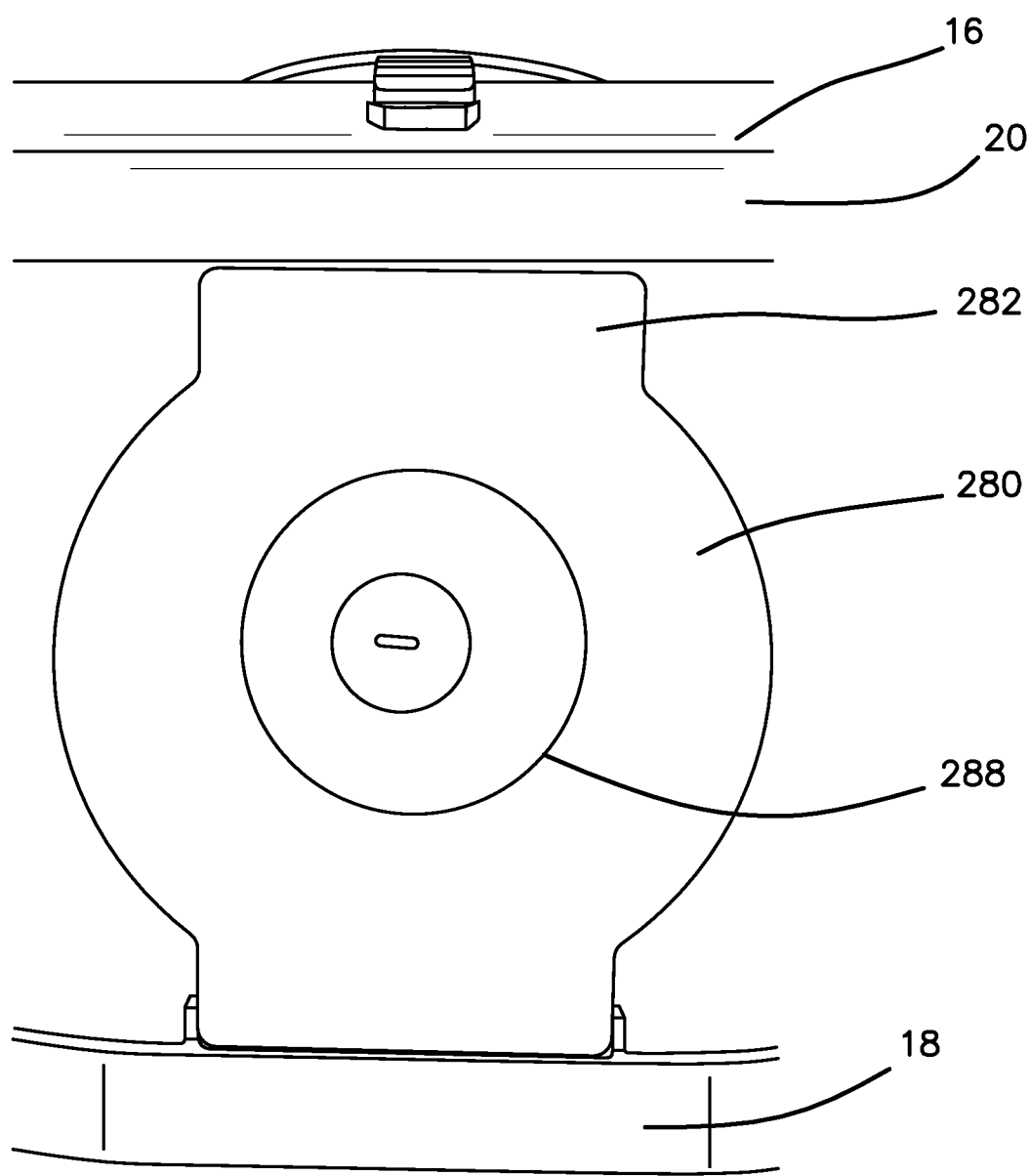
FIG. 59 is an end view of a simulated uterus connected to a transvaginal adapter that is connected between a top cover and a base of surgical trainer is a top perspective view of a transvaginal adapter according to the present invention.

The distal end 262 of the simulated uterus 216 may be provided with simulated ovaries 344. The method of manufacturing simulated ovaries 344 includes the step of providing an ovary mold 346 which is typically a two-piece mold comprising two halves as shown in FIGS. 53 and 54. The mold 346 includes a well 348 that is shaped like an ovary. A cylindrical silicone vessel 350 is provided inside the well 348 and inside channels spanning across the mold 346. The silicone vessel 350 may be tied into a knot and the knot placed in the location of the ovary well 348 to provide more structure to the resulting simulated ovary. The mold 346 is closed and uncured silicone is then injected into the mold 346. The silicone is allowed to cure in the mold and around the silicone vessel 350 become attached thereto. The mold 346 is opened and the simulated ovary 344 is removed and one end of the silicone vessel 350 is attached with adhesive to the simulated uterus 216 and other end of the silicone vessel is attached to the frame 204 by pulling the silicone vessel through one of the apertures 212 provided in the frame 204.

With reference back to FIGS. 29-30, the simulated rectum 220 is a tubular structure made of silicone with molded transverse folds. The simulated rectum 220 has a proximal end 244 and a distal end 246. Each of the first sheet 222, second sheet 224 and third sheet 225 comprises a flat planar layer of silicone material. Both sheets 222, 224 represent the peritoneum and the third sheet 225 represents a bladder flap or peritoneal reflection. The first sheet 222 has a first surface 232 and a second surface 234 and a proximal end 248 and a distal end 250. A cutout (not shown) may be provided in from the distal end 250 such that the first sheet 222 does not overlap a portion of the simulated uterus 216. The second sheet 224 has a first surface 236 and a second surface 238 and a proximal end 252 and a distal end 254. A cutout (not shown) may be provided at the proximal end 252 of the second sheet 224 such that a portion of the simulated uterus 216 is not overlapped. The third sheet 225 has a proximal end 352 and a distal end 354 and a first surface 356 and a second surface 358.

With continued reference to FIGS. 29-30, the assembly, configuration and connection of the plurality of simulated organ structures 202 will now be described. The distal end of the bladder 242 is attached to the first surface 232 of the first sheet 222 with adhesive approximately midway between the proximal end 248 and the distal end 250 of the first sheet 222 such that the first sheet 222 wraps around the distal end 242 of the simulated bladder 214 from the top of the simulated bladder to the bottom of the simulated bladder 214. The proximal end of the bladder 240 is attached to the first surface 356 of the third sheet 225 with adhesive such that the third sheet 225 wraps around the proximal end 240 of the simulated bladder 214 from the top of the simulated bladder to the bottom of the simulated bladder 214. The first sheet 222 and the third sheet 225 come together at the bottom of the simulated bladder 214 to contact a silicone webbing 360. In lieu of a silicone webbing 360, silicone glue is used to connect the two sheets 222, 225. The first surface 232 of the first sheet 222 is attached to a fastener 210 near the distal end 248 of the first sheet 222. The first sheet 222 is folded in an approximate U-shape such that the distal end 250 of the first sheet 222 and, in particular, the first surface 232 of the first sheet 222, is attached to the simulated uterus 216 and attached to the simulated vaginal canal 218 using adhesive. The third sheet 225 turns around at point 360 and backs over itself towards the proximal end creating an overlap. In this location where the third sheet overlaps itself, the sticky silicone of the third sheet 225 will easily stick onto itself. Advantageously, this overlapping portion is what a surgeon will practice separating when the surgeon approaches point 360 from the proximal end. In use laparoscopically, the surgeon will practice delicately separating the overlap until point 360 is approached where a silicone membrane is formed by adhesive or other means. When point 360 is reached, the surgeon will dissect the silicone membrane 360 to detach the uterus. In use transvaginally, the surgeon will approach via the lumen of vaginal canal 218 and make a circumferential incision through the vaginal canal 218 and then detach the membrane 360. In doing so, the surgeon will advantageously not notice the third sheet 225 which, in essence, is not anatomically correct, because the third sheet 225 is very thin and is well-adhered to the vaginal canal and bladder. In one variation, the third sheet 225 does not include surface texturing in order to create a closer adherence to the vaginal canal and bladder. In another variation, the third sheet 225 is omitted. In such a variation, the bladder 240 is adhered to the vaginal canal 218 directly or indirectly via a fiber layer as shown in FIGS. 14-15.

The second sheet 224 is attached between the simulated uterus 216 and the simulated rectum 220. In particular, the first surface 236 at the distal end 252 of the second sheet 224 is attached near the distal end 262 of the simulated uterus 216. The second sheet 224 is attached along the length of the simulated uterus 216 toward the proximal end 260 using adhesive. The second sheet 224 is folded to extend back towards the distal end of the simulated rectum 220 and attached along the top side and outer surface of the simulated rectum 220 such that the distal end 254 of the second sheet 224 is near the distal end 246 of the simulated rectum 220. The top side of the simulated bladder 214 is connected to a fastener 210 and this fastener 210 is passed through an aperture 212 in the top frame 206 of the frame 204. The proximal end 248 of the first sheet 222 is also attached to a fastener 210 which is also passed through an aperture 212 in the top frame 206 of the frame 204 to attach the plurality of the simulated organ structures 202 to the frame 204 in a suspended manner. While suspended from the top frame 204, the interconnected plurality of simulated organ structures 202 advantageously pendulate and move together in a realistic fashion wherein the point of contact with instruments and the like will move most and simulated organs distal to the point of contact with instruments move to a lesser degree. The bottom side of the simulated rectum 220 is attached to at least two fasteners 210 as shown in FIGS. 29-30. The two fasteners 210 are passed through apertures 212 in the bottom frame 208 to secure the plurality of simulated organ structures 202 to the frame 202. Hence, the plurality of simulated organs structures is spanned across the central opening of the frame 202 with the first sheet 222 and second sheet 224 forming an interconnecting webbing. The proximal end 260 of the simulated uterus 216 is inserted into the distal end 258 of the simulated vaginal canal 218 and joined together with adhesive. The simulated cervix 334 is provided made of silicone and located inside the simulated uterus 216 at the proximal end 260 as described above.

The fastener 210 is the same fastener 210 as described above with respect to FIG. 16. Turning now to FIGS. 55-59, a transvaginal adapter 280 will now be described. As described above, the transvaginal adapter 280 is formed as a leg 20 configured to support the top cover 16 of the trainer 10. It is configured for simulating transvaginal surgery including transvaginal hysterectomies. The transvaginal adapter 280 includes a flat plate 282 having an inner surface 284 for facing toward the interior of the trainer and an outer surface 286 for facing outwardly towards the user. The plate 280 has a rectangular shape and includes an aperture 288 passing through the plate 280 from the inner surface 284 to the outer surface 286. In one variation, the aperture 288 is circular in shape. In another variation, the aperture 288 is elongate elliptical, oval-like in shape and oriented vertically along the longitudinal axis of the adapter 280. In another variation, the aperture 288 is elongate elliptical, oval-like in shape and oriented perpendicularly to the longitudinal axis of the adapter. The plate 280 also includes means such as tabs 290 or a U-shaped channel for inserting to connect the transvaginal adapter 280 to the top cover 16 and to the base 18 to help support and space apart the top cover 16. The transvaginal adapter 280 is located between the top cover 16 and the base 18 and provides a side access aperture 288 lateral to the trainer 10 or substantially perpendicular to the top cover 16 and the base 18. The access aperture 288 is extra-large to simulate a pre-retracted vaginal canal as described above. The proximal end 256 of the simulated vaginal canal 218 is stretched over the access aperture 288 at the inner surface 284 to connect the simulated vaginal canal 218 to the adapter 280. The adapter advantageously secures the model in every axial direction and serves as an interface for the surgeon. The adapter is also not anatomically correct but advantageously permits use of real instrumentation.

In use, a practicing surgeon may approach the simulated uterus 216 with surgical instruments and retractors through the transvaginal adapter 280 to perform a transvaginal hysterectomy. Alternatively, the simulated uterus 216 may be approached through the simulated abdominal wall of the top cover 16 of the trainer 10. The user will practice laparoscopic surgical skills, employing a trocar and scope to examine the anatomy and perform the simulated surgical hysterectomy. The procedure involves making key incisions to detach the uterus and then remove it. In particular, the model 200 advantageously provides the first sheet 222 and third sheet 225 and silicone webbing 360 that make the incisions and separation of the simulated uterus 216 realistic. Also, the KEVLAR synthetic fiber mesh reinforced simulated cervix 334 prevents tearing of the silicone when being pulled. The user may further practice suturing the simulated vaginal canal 218 after removal of the simulated uterus 216. For this purpose, the simulated vaginal canal 218 is provided with an embedded mesh that makes it possible for the silicone to hold sutures without easily tearing. After use, the model 200 is removed from the trainer 10 and the plurality of simulated organ structures 202 is removed from the model 200 by releasing the fasteners 212 from the frame 204. A new plurality of simulated organ structures 202 is then connected to the frame 204 and inserted into the trainer 10 for continued practice.

Any portion of the model can be made of one or more organic base polymer including but not limited to hydrogel, single-polymer hydrogel, multi-polymer hydrogel, rubber, latex, nitrile, protein, gelatin, collagen, soy, non-organic base polymer such as thermo plastic elastomer, Kraton, silicone, foam, silicone-based foam, urethane-based foam and ethylene vinyl acetate foam and the like. Into any base polymer one or more filler may be employed such as a fabric, woven or non-woven fiber, polyester, nylon, cotton and silk, conductive filler material such as graphite, platinum, silver, gold, copper, miscellaneous additives, gels, oil, cornstarch, glass, dolomite, carbonate mineral, alcohol, deadener, silicone oil, pigment, foam, poloxamer, collagen, gelatin and the like. The adhesives employed may include but are not limited to cyanoacrylate, silicone, epoxy, spray adhesive, rubber adhesive and the like.

It is understood that various modifications may be made to the embodiments and variations disclosed herein. Therefore, the above description should not be construed as limiting, but merely as exemplifications of preferred embodiments. Those skilled in the art will envision other modifications within the scope and spirit of the present disclosure.

We claim:

1. A surgical simulator for surgical training comprising:
a frame having an inner surface and an outer surface defining a frame wall therebetween, wherein the inner surface defines a central lumen that extends along a longitudinal axis of the frame, and wherein the central lumen has a proximal opening and a distal opening,
wherein the frame is configured to removably receive at least one artificial tissue structure within the lumen such that the at least one artificial tissue structure is at least partially suspended within the central lumen and at least partially encompassed by the frame wall along the central lumen,
wherein the at least one artificial tissue structure being suspended with fasteners that connect the at least one artificial tissue structure to the frame wall,
wherein the central lumen has a cross-sectional area taken perpendicular to the longitudinal axis, and
wherein the cross-sectional area of the central lumen progressively increases from the proximal opening of the frame to the distal opening of the frame such that the frame has a frusto-conical shape.

2. The surgical simulator of claim 1 wherein the at least one artificial tissue structure has an organ lumen having an opening at a proximal end of the at least one artificial tissue structure, and wherein the organ lumen is positioned such that the opening of the at least one artificial tissue structure is facing in the same direction as the proximal opening of the frame.

3. The surgical simulator of claim 1, wherein the at least one artificial tissue structure is selected from a group consisting of at least one of a simulated uterus, a vaginal canal, a cervix, fallopian tubes, a bladder, a rectum, and a peritoneum.

4. The surgical simulator of claim 1 further comprising a laparoscopic trainer, wherein the laparoscopic trainer comprises a top cover and a base that define a cavity therebetween, wherein the laparoscopic trainer further comprises at least one aperture within the top cover, and wherein the aperture provides access to the organ lumen of the at least one artificial tissue structure associated with the surgical simulator within the laparoscopic trainer.

5. The surgical simulator of claim 1, wherein the at least one artificial tissue structure is located inside the frame, and wherein the frame is increasingly laterally constricted along the longitudinal axis of the frame from the distal opening of the frame to the proximal opening of the frame.

6. The surgical simulator of claim 1, wherein the fasteners comprise:
a proximal end connected to the at least one simulated tissue structure, and
a distal end that attaches to the frame.

7. The surgical simulator of claim 6, wherein the distal ends of the fasteners are sized and configured for a friction fit engagement with a plurality of apertures formed in the frame wall of the frame.

8. The surgical simulator of claim 7, wherein the fastener and the apertures formed in the frame wall of the frame are color coded.

9. The surgical simulator of claim 6, wherein the proximal end of the fasteners uses adhesives to connect the fastener to the at least one simulated tissue structure.

10. The surgical simulator of claim 6, wherein the distal end of the fastener has two prongs that are resiliently deflectable, wherein the two prongs snap and hook with an aperture of the frame wall in order to secure the fastener to the frame wall.

11. The surgical simulator of claim 6, wherein the distal end of the fastener has one prong with a bulbous portion, and wherein the one prong snaps through an aperture of the frame wall in order to secure the fastener to the frame wall.

12. The surgical simulator of claim 6, wherein the proximal end of the fasteners uses wet silicone to connect the fastener to the at least one simulated tissue structure.

13. A surgical simulator for surgical training comprising, a frame having an inner surface and an outer surface defining a frame wall therebetween, wherein the inner surface defines a central lumen that extends along a longitudinal axis of the frame, and wherein the central lumen has at least one of a proximal opening and a distal opening,
wherein the frame is configured to removably receive at least one artificial tissue structure within the lumen such that the at least one artificial tissue structure is at least partially suspended within the central lumen and at least partially encompassed by the frame wall along the central lumen,
wherein the at least one artificial tissue structure being suspended with fasteners that connect the at least one artificial tissue structure to the frame wall,
wherein the central lumen has a cross-sectional area taken perpendicular to the longitudinal axis,
wherein the cross-sectional area of the central lumen progressively increases from the at least one proximal opening of the frame to the distal opening of the frame, and
wherein the at least one artificial tissue structure is suspended within the frame along the longitudinal axis such that the at least one artificial tissue structure is permitted to pendulate more at the distal opening of the frame relative to the proximal opening of the frame.

14. A surgical simulator for surgical training comprising, a frame having an inner surface and an outer surface defining a frame wall therebetween, wherein the inner surface defines a central lumen that extends along a longitudinal axis of the frame, and wherein the central lumen has at least one of a proximal opening and a distal opening,
wherein the frame is configured to removably receive at least one artificial tissue structure within the lumen such that the at least one artificial tissue structure is at least partially suspended within the central lumen and at least partially encompassed by the frame wall along the central lumen,
wherein the at least one artificial tissue structure being suspended with fasteners that connect the at least one artificial tissue structure to the frame wall,
wherein the central lumen has a cross-sectional area taken perpendicular to the longitudinal axis, wherein the cross-sectional area of the central lumen progressively increases from the at least one proximal opening of the frame to the distal opening of the frame, and wherein the frame wall has a planar top wall that is substantially parallel to a planar bottom wall, and wherein the planar top wall and the planar bottom wall are interconnected by two planar sidewalls convergently angled toward the proximal opening of the frame.

15. The surgical simulator of claim 14, wherein the two planar sidewalls are substantially perpendicular to the planar top wall and the planar bottom wall.

16. A surgical simulator for surgical training comprising, a frame having an inner surface and an outer surface defining a frame wall therebetween, wherein the inner surface defines a central lumen that extends along a longitudinal axis of the frame, and wherein the central lumen has at least one of a proximal opening and a distal opening, wherein the frame is configured to removably receive at least one artificial tissue structure within the lumen such that the at least one artificial tissue structure is at least partially suspended within the central lumen and at least partially encompassed by the frame wall along the central lumen, wherein the at least one artificial tissue structure being suspended with fasteners that connect the at least one artificial tissue structure to the frame wall, wherein the central lumen has a cross-sectional area taken perpendicular to the longitudinal axis, wherein the cross-sectional area of the central lumen progressively increases from the at least one proximal opening of the frame to the distal opening of the frame, and wherein the at least one artificial tissue structure is also supported using tubular structures, wherein the tubular structures have a first free end and a second end connected to the at least one artificial tissue structure, and wherein the first free end is passed through an aperture of the frame.

17. The surgical simulator of claim 16, wherein one of more of the tubular structures are secured to provide a custom amount of tension.

18. A surgical simulator for surgical training comprising:
a frame having an inner surface and an outer surface defining a frame wall therebetween, wherein the inner surface defines a central lumen that extends along a longitudinal axis of the frame, and wherein the central lumen has at least one of a proximal opening and a distal opening, wherein the frame is configured to removably receive at least one artificial tissue structure within the lumen such that the at least one artificial tissue structure is at least partially suspended within the central lumen and at least partially encompassed by the frame wall along the central lumen, wherein the at least one artificial tissue structure being suspended with fasteners that connect the at least one artificial tissue structure to the frame wall, wherein the central lumen has a cross-sectional area taken perpendicular to the longitudinal axis, wherein the cross-sectional area of the central lumen progressively increases from the at least one proximal opening of the frame to the distal opening of the frame; and one or more sheets that are attached to the at least one artificial tissue structure at a first end and attached to the frame wall of the frame at a second end, wherein the attachment of the one or more sheets is performed using adhesives, and wherein the one or more sheets also suspends the at least one artificial tissue structure within the central lumen of the frame.

\* \* \* \* \*